(12) United States Patent
Lackey et al.

(10) Patent No.: US 7,030,150 B2
(45) Date of Patent: Apr. 18, 2006

(54) BENZIMIDAZOLE COMPOUNDS AND ANTIVIRAL USES THEREOF

(75) Inventors: John William Lackey, Hillsborough, NC (US); Daniel S Kinder, Apex, NC (US); Nicolai A Tvermoes, Durham, NC (US)

(73) Assignee: Trimeris, Inc., Morrisville ( * ) Notice: Subject to any disclaimer, the term of this patent is extended or adjusted under 35 U.S.C. 154(b) by 0 days.

(21) Appl. No.: 10/141,839

(22) Filed: May 9, 2002

(65) Prior Publication Data

US 2003/0119754 A1 Jun. 26, 2003

Related U.S. Application Data

(60) Provisional application No. 60/290,038, filed on May 11, 2001.

(51) Int. Cl.
*A61K 31/4184* (2006.01)
*C07D 403/14* (2006.01)

(52) U.S. Cl. .............. 514/394; 514/394; 514/316; 514/322; 514/338; 514/307; 514/310; 514/211.08; 514/211.15; 514/219.09; 514/234.5; 514/254.06; 540/575; 540/603; 544/139; 544/360; 544/370; 546/199; 546/273.4; 546/145; 546/148; 546/187; 548/305.7

(58) Field of Classification Search ............. 548/305.7; 544/139, 360, 370; 546/199, 273.4, 145, 546/148, 187; 540/575, 603; 514/394, 316, 514/322, 338, 307, 310, 211.08, 211.15, 217.09, 514/234.5, 254.06
See application file for complete search history.

(56) References Cited

U.S. PATENT DOCUMENTS

| | | | |
|---|---|---|---|
| 3,394,141 A | | 7/1968 | Sparatore |
| 4,839,374 A | * | 6/1989 | Janssens et al. .............. 514/394 |
| 5,280,030 A | * | 1/1994 | Jegham et al. .............. 514/322 |
| 5,399,580 A | | 3/1995 | Daluge |
| 5,545,653 A | | 8/1996 | Miller et al. |
| 5,559,256 A | | 9/1996 | Gordon et al. |
| 5,576,322 A | * | 11/1996 | Takase et al. .......... 514/266.22 |
| 5,852,011 A | | 12/1998 | Matsunaga et al. |
| 5,891,874 A | | 4/1999 | Colacino |
| 5,932,571 A | * | 8/1999 | Maynard et al. .............. 514/218 |
| 6,194,406 B1 | * | 2/2001 | Kane et al. .................. 514/218 |
| 6,423,704 B1 | * | 7/2002 | Maynard et al. .............. 514/218 |
| 6,448,281 B1 | * | 9/2002 | Beaulieu et al. .............. 514/394 |

FOREIGN PATENT DOCUMENTS

| | | |
|---|---|---|
| DE | 11 78 070 | 9/1964 |
| EP | 0 151 826 | 8/1985 |
| EP | 0 161 049 | 2/1990 |
| EP | 0 747 363 | 12/1996 |
| JP | 9-3065 | 7/1997 |
| WO | WO 93/14088 | 7/1993 |
| WO | WO 96/00730 | 1/1996 |
| WO | WO 96/40125 | 12/1996 |
| WO | WO 97/24119 | 7/1997 |
| WO | WO-97/30991 * | 8/1997 |
| WO | WO 98/37072 | 8/1998 |
| WO | WO 99/44596 | 9/1999 |
| WO | WO 00/04900 | 2/2000 |
| WO | WO 01/00611 | 1/2001 |
| WO | WO 01/00612 | 1/2001 |
| WO | WO 01/00615 | 1/2001 |
| WO | WO 01/27090 | 4/2001 |

OTHER PUBLICATIONS

CA Registry No. 152072-73-6, entry date into the Registry file Jan. 4, 1994.*
CA Registry No. 152072-57-6, entry date into the Registy file Jan. 4, 1994.*
Bobosik et al., Heterocycles (1993), 35(2), pp. 1067-1074.*
Sturm et al., Journal of Chromatography (1988), 430(1), pp. 43-51.*
Kuzmierkiewicz, CA 106:50163, 1987.*
Layton et al., Journal of the Chemical Society [Section] C: Organic (1968), (5), pp. 611-614.*
U.S. Appl. No. 60/216,084, filed Jul. 6, 2000.*
Abman et al., 1988, "Role of respiratory syncytial virus in early hospitalizations for respiratory distress of young infants with cystic fibrosis", J Pediatr. 113(5):826-30.

(Continued)

Primary Examiner—Laura L. Stockton
(74) Attorney, Agent, or Firm—Jones Day

(57) ABSTRACT

The present invention relates to novel benzimidazole compounds that have useful antiviral activity. More specifically, the invention encompasses benzimidazole compounds that inhibit membrane fusion associated events such as viral transmission, reduce viral load or otherwise treat viral infections. The invention also encompasses the use of benzimidazole compounds as inhibitors of membrane fusion associated events, such as viral transmission. In another embodiment, the invention encompasses processes for making benzimidazole compounds, methods of using the benzimidazole compounds and compositions comprising the benzimidazole compounds. Finally, the invention provides methods for treating, preventing or ameliorating symptoms associated with respiratory infection, particularly that caused by Respiratory Syncytial Virus utilizing the novel benzimidazole compounds of the invention.

39 Claims, No Drawings

OTHER PUBLICATIONS

Carstensen, J., 1995, Drug Stability: Principles and Practice, 2nd ed., Marcel Dekker, NY, NY pp. 379-380.

Castellanos et al., 1985, "Nucleophlic substitution in quaternary salts of N,N'-linked biazoles and related systems", J. of the Chem. Society, 1209-1215.

Collings et al., 1984, "Identification of a tenth mRNA of respiratory syncytial virus and assignment of polypeptides to the 10 viral genes", J Virol. 49(2):572-8.

Doud et al., 1992, "Respiratory syncytial virus pneumonia in a lung transplant recipient: case report", J Heart Lung Transplant. 11(1 Pt 1):77-9.

During et al., 1989, "Controlled release of dopamine from a polymeric brain implant: in vivo characterization", Ann Neurol. 25(4):351-6.

Falsey et al., 1991, "Noninfluenza respiratory virus infection in long-term care facilities", Infect Control Hosp Epidemiol. 12(10):602-8.

Feigen et al., eds., 1987, Textbook of Pediat. Infect. Disease, WB Saunders, Philadelphia, pp. 1653-1675.

Goodson et al., 1984, "The Scope of Dental Therapy", Med. Applications of Controlled Release, vol. 2, pp. 115-138.

Grey et al., 1980, "Outbreak of respiratory syncytial virus infection in the elderly", Br Med J. 281(6250):1253-4.

Groothuis et al., 1988, Respiratory syncytial virus infection in children with bronchopulmonary dysplasia', Pediatrics. 82(2):199-203.

Hall et al., 1981, "Modes of Transmission of Respiratory Synctial Virus", J. Pediatr. 99:101-103.

Hall et al., 1979, "Neonatal respiratory syncytial virus infection", N Engl J Med. 300(8):393-6.

Hall CB, 1993, "Respiratory Syntial Virus: What we know now", Contemp Pediatr. 10:92-110.

Harrison et al., 1965, "Nucleophilic substitution reactions of 2-chlorobenzimidazoles. Part II. Formation of benzimidazoine2-2thiones and related compounds", J. of the Chem. Society 3132-3135.

Hemming et al., 1995, "Hyperimmune globulins in prevention and treatment of respiratory syncytial virus infections", Clin Microbiol Rev.8(1):22-23.

Henderson et al., 1979, "Respiratory-syncytial-virus infections, reinfections and immunity. A prospective, longitudinal study in young children", N Engl J Med. 300(10):530-4.

Hertz et al., 1989, "Respiratory syncytial virus-induced acute lung injury in adult patients with bone marrow transplants: a clinical approach and review of the literature", Medicine(Baltimore). 68(5):269-81.

Hollinshead and Smith, "Effects of Certain Purines and Related Compounds on Virus Propagation", Purines in Virus Chemotherapy 123:54-62, 1958.

Howard et al., 1989, Intracerebral drug delivery in rats with lesion-induced memory deficits. J Neurosurg. 71(1):105-12.

Ishida et al., 1975, "Tris (benzimidazo)-1,3,5-triazine from the thermolysis of 2-aryloxybeznzimaidazoles", Bulletin of Chem. Soc. Of Japan 48:956-959.

Johnson et al., 1999, "A direct comparison of the activities of two humanized respiratory syncytial virus monoclonal antibodies: MEDI-493 and RSHZl9", J Infect Dis. Jul.; 180(1):35-40.

Johnson et al., 1997, "Development of a humanized monoclonal antibody (MEDI-493) with potent in vitro and in vivo activity against respiratory synctial virus", J Infect Dis. 176(5):1215-24.

Langer and Peppas, 1983, J Macromol. Sci. Rev. Marcomol. Chem. 23:61.

Langer et al., 1990, "New methods of drug delivery", Science. 249(4976):1527-33.

Levy et al., 1985, "Inhibition of calcification of bioprosthetic heart valves by local controlled-release diphosphonate", Science. 228(4696):190-2.

Lopez Bernstein et al., Liposomes in the Therapy of Infectious Diseases and Cancer, Lopez-Bernstein and Fidler eds, Liss, NY, pp. 353-465, pp. 317-327, 1989.

MacDonald et al., 1982, "Respiratory syncytial viral infection in infants with congenital heart disease", N Engl J Med. 307(7):397-400.

Murphy et al., 1994, "An update on approaches to the development of respiratory syncytial virus (RSV) and parainfluenza virus type 3 (PIV3) vaccines", Virus Res. 32(1):13-36.

Navas et al., 1992, "Improved outcome of respiratory syncytial virus infection in a high-risk hospitalized population of Canadian children. Pediatric Investigators Collaborative Network on Infections in Canada", J Pediatr. 121(3): 348-54.

Patterson et al., 1990, "Molecular mechanisms of action of ribavirin", Rev Infect Dis. 12(6):1139-46.

Peigue-Lafeuille et al., 1990, "Severe respiratory syncytial virus pneumonia in an adult renal transplant recipient: successful treatment with ribavirin", Scand J Infect Dis. 22(1):87-9.

Pohl et al., 1992, "Respiratory syncytial virus infections in pediatric liver transplant recipients", J Infect Dis. 165(1): 166-9.

Prince et al., 1985, "Quantitative aspects of passive immunity of respiratory syncytial virus infection in infant cotton rats", J Virol. Sep.; 55(3):517-20.

Pringle et al., 1985, "A survey of respiratory syncytial virus and parainfluenza virus type 3 neutralising and immunoprecipitating antibodies in relation to Paget disease", J Med Virol. 17(4):377-86.

Roderick et al., 1972, "Bisbenzimidazoles. Potent Inhibitors of Rhinoviruses", J. Med. Chem. 15:655-658.

Ruuskanen et al., "Respiratory syncytial virus", Curr Probl Pediatr., Feb. 1993; 23(2):50-79.

Saudek et al., 1989, "A preliminary trial of the programmable implantable medication system for insulin delivery", N Engl J Med. 321(9):574-9.

Schleicher et al., 1972, "Antiviral Activity in Tissue Culture Systems of bis-Benzimidazoles, Potent Inhibitors of Rhinoviruses", Microbiology 23:113-116.

Sefton et al, 1987, "Implantable pumps", Crit Rev Biomed Eng. 14(3):201-40.

Sinnott et al., 1988, "Respiratory syncytial virus pneumonia in a cardiac transplant recipient", J Infect Dis. 158(3):650-1.

Smith et al., 1991, "A controlled trial of aerosolized ribavirin in infants receiving mechanical ventilation for severe respiraotry syncytial virus infection", N Engl J Med.325(1): 24-9.

Steck et al., 1948, "Absorption spectra of heterocyclic compounds. III. Some benzimidazole derivatives", J. of the Amer. Chem. Society. 70:3406-3410.

Taylor et al., 1984, "Respiratory syncytial virus infection in mice", Infect Immun. 43(2):649-55.

Whimbey et al., 1995, "Respiratory syncytial virus pneumonia in hospitalized adult patients with leukemia", Clin Infect Dis. 21(2):376-9.

Willitzer et al., 1978, "Synthese und antivirale Wirsamkeit von substituierten 5-ureido-und 5-thioureidobenzimidazolderivaten", Pharmazie 33:30-38.

Wu and Wu, 1987, "Receptor-mediated in vitro gene transformation by a soluble DNA carrier system", J Biol Chem. 262(10):4429-32.

Wyatt et al., 1995, "Benzophenone Derivatives: A Novel Series of Potent and Selective Inhibitors of Human Immunodeficiency Virus Type I Reverse Transcriptionase", J. Med. Chem. 38:1657-1665.

Kuzmierkiewicz, W. "Oxidation Reaction of Benzimidazoline-2-Thione with Dimethyl Sulfoxide," *Polish Journal of Chemistry* 59(7-9):921-923 (1985).

* cited by examiner

BENZIMIDAZOLE COMPOUNDS AND ANTIVIRAL USES THEREOF

This application claims the benefit of U.S. Provisional Application No. 60/290,038 filed May 11, 2001, which is incorporated herein by reference.

1. INTRODUCTION

The present invention relates to novel benzimidazole compounds that have useful antiviral activity. More specifically, the invention encompasses benzimidazole compounds that inhibit membrane fusion associated events such as viral transmission, reduce viral load or otherwise treat viral infections. The invention also encompasses the use of benzimidazole compounds as inhibitors of membrane fusion associated events, such as viral transmission. In another embodiment, the invention encompasses processes for making benzimidazole compounds, methods of using the benzimidazole compounds and compositions comprising the benzimidazole compounds. Finally, the invention provides methods for treating, preventing or ameliorating symptoms associated with respiratory infection, particularly that caused by Respiratory Syncytial Virus utilizing the novel benzimidazole compounds of the invention.

2. BACKGROUND OF THE INVENTION

Respiratory infections strike millions of people each year and collectively cause more deaths than any single infectious disease (National Institute of Allergy and Infectious Diseases News Release, Oct. 30, 2000). Respiratory illness is most commonly caused by a viral infection.

Paramyxoviruses cause several respiratory diseases in humans and animals. Of these viruses, Respiratory Syncytial Virus ("RSV"), is an infectious agent that causes epidemics associated with extensive mortality and morbidity. The yearly epidemic nature of RSV infection is evident worldwide, but the incidence and severity of RSV disease in a given season vary by region (Hall, C. B., 1993, *Contemp. Pediatr.* 10:92–110). In temperate regions of the northern hemisphere, it usually begins in late fall and ends in late spring. Propagation of outbreaks is facilitated by the ease of transmission of RSV, which occurs by exposure to droplets of respiratory secretions of infected individuals (Hall et al., 1981, *J. Pediatr.* 99:101–103).

RSV is the leading cause of serious lower respiratory tract disease in infants and children (Feigen et al., eds., 1987, *In: Textbook of Pediatric Infectious Diseases,* W B Saunders, Philadelphia at pages 1653–1675; *New Vaccine Development, Establishing Priorities,* Vol. 1, 1985, National Academy Press, Washington D.C. at pages 397–409; and Ruuskanen et al., 1993, *Curr. Probl. Pediatr.* 23:50–79). By the age of three, virtually every child in America has had at least one respiratory infection caused by RSV. Of the eight million children under the age of five infected by RSV in the United States each year, approximately 5,000 die, another 100,000 are hospitalized, and 2.4 million are treated by a physician. Primary RSV infection occurs most often in children from 6 weeks to 2 years of age and uncommonly in the first 4 weeks of life during nosocomial epidemics (Hall et al, 1979, *New Engl. J. Med.* 300:393–396). Children at increased risk from RSV infection include preterm infants (Hall et al., 1979, *New Engl. J. Med.* 300:393–396) and children with bronchopulmonary dysplasia (Groothuis et al., 1988, *Pediatrics* 82:199–203), congenital heart disease (MacDonald et al., *New Engl. J. Med.* 307:397–400), congenital or acquired immunodeficiency (Ogra et al., 1988, *Pediatr. Infect. Dis. J.* 7:246–249; and Pohl et al., 1992, *J. Infect. Dis.* 165:166–169), and cystic fibrosis (Abman et al., 1988, *J. Pediatr.* 113:826–830). The fatality rate in infants with heart or lung disease who are hospitalized with RSV infection is 3%–4% (Navas et al., 1992, *J. Pediatr.* 121: 348–354).

RSV infects adults as well as infants and children. In healthy adults, RSV causes predominantly upper respiratory tract disease. Several epidemics have been reported among nursing home patients and institutionalized young adults (Falsey, 1991, *Infect. Control Hosp. Epidemiol.* 12:602–608; and Garvie et al., 1980, *Br. Med. J.* 281:1253–1254). RSV may cause serious disease in immunosuppressed persons, particularly bone marrow transplant patients (Hertz et al., 1989, *Medicine* 68:269–281). RSV has also been reported as a problem in individuals undergoing cardiac, renal and lung transplants and in leukemia patients (Sinnot, et al., 1988, *J. Infect. Dis.* 158:650–651; Peigue-Lafeuille et al., 1990, *Scand. J. Infect. Dis.* 22:87–89; Doud et al, 1992, *J. Heart Lung Transplant* 11:77–79; and Whimbey et al., *Clin. Infect. Dis.* 21:376–379).

RSV is a non-segmented, negative-stranded RNA virus of the Paramyxoviridae family. RSV replicates in the cytoplasm of infected host cells and buds through the apical membrane, thereby acquiring its lipid envelope. The entire genetic material is associated with virus-encoded proteins, including the polymerase, which together form the nucleocapsid and are packaged in the virion (Collins et al., 1996, *In: Virology,* Raven Press at pp. 1313–1351). The 15,222 nucleotide genome encodes ten major proteins of which three, the F (fusion), G (attachment) and small hydrophobic SH (unknown function) proteins, are expressed on the virion surface and anchored in the lipid membrane (Collins et al., 1984, *J. Virol.* 49:572–578). Of the surface proteins, the F protein has emerged as a target for therapeutic intervention, largely in part because of its crucial role in viral entry. The F protein is thought to mediate fusion of virus and host cell membranes in a fashion that is common to many viruses; however, the mechanism of RSV viral fusion remains to be determined. Although antiviral strategy targeting the fusion pathway of viruses such as HIV has been successful, a need for successful antiviral strategies against RSV still exists.

Treatment options for established RSV disease are limited. Severe RSV disease of the lower respiratory tract requires considerable supportive care, including administration of humidified oxygen and respiratory assistance (Fields et al., eds., 1990, *Fields Virology,* 2$^{nd}$ ed., Vol. 1, Raven Press, New York at pages 1045–1072). Understanding of molecular aspects of the RSV life cycle is limited and has prevented a more fundamental, mechanism-based approach for antiviral drug discovery. As a consequence, most inhibitors of RSV disclosed to date have been discovered by a strategy of screening using a tissue cell culture assay.

The only clinically approved small-molecule therapy for the treatment of RSV infection is the antiviral agent ribavirin (marketed for RSV by ICN Pharmaceuticals, Costa Mesa, Calif.) (American Academy of Pediatrics Committee on Infectious Diseases, 1993, *Pediatrics* 92:501–504). Ribavirin is a nucleoside analog, but the precise mode of action remains to be established (Patterson et al., 1997, *Rev. Infect. Dis.* 12:1139–1146). The compound is effective in vitro against a broad spectrum of RNA viruses, and the inhibition of influenza virus by ribavirin is well-studied. This compound has been shown to be effective in the treatment of RSV pneumonia and bronchiolitis and has been shown to modify the course of severe RSV disease in immunocompetent children (Smith et al., 1991, *New Engl. J. Med.* 325:24–29). However, ribavirin has had limited use against RSV infection because it requires prolonged aerosol administration and because of concerns about its potential risks and side effects.

In addition to nucleoside analogs, several other agents have been investigated as anti-RSV molecules. Some agents have been characterized as inhibitors of RSV adsorption, although a detailed understanding of their mode of action remains to be elucidated. Examples of such agents are peptidic fusion inhibitors based on the identification of domains in the RSV F protein hypothesized to interact with each during stages of the fusion process. Because of the difficulties associated with identifying inhibitors of viral proteins and a limited range of targets, viruses such as RSV have also emerged as candidates for the development of therapeutics based on antisense oligonucleotides.

The difficulties in finding effective therapeutic agents has led to a focus on finding agents for the prevention of RSV infection. No vaccine is yet licensed for this indication. A major obstacle to vaccine development is safety. Several candidate RSV vaccines have been abandoned and others are under development (Murphy et al., 1994, *Virus Res.* 32:13–36), but even if safety issues are resolved, vaccine efficacy must also be improved. Recently, antibodies designed to induce passive immunization, such as Synagis® (a monoclonal antibody developed by MedImmune, Gaithersburg, Md.), have proved to be safer and more efficient than viral vaccines (Hemming et al., 1995, *Clin. Microb. Rev.* 8:22–33; Weltzin, 1998, *Expert Opin. Invest. Drugs* 7:1271–1283). However, even though the characterization of prophylactic agents has yielded promising results, effective therapeutic agents are still needed for the treatment of established RSV infection. Primary RSV infection and disease do not protect well against subsequent RSV disease (Henderson et al., 1979, *New Engl. J. Med.* 300:530–534).

Although many agents are being investigated, potent and specific, orally active antiviral agents have yet to be definitively characterized. So far, there is no ideal treatment for RSV infection, and there is no cure. Accordingly, novel therapeutics are needed that more effectively treat RSV infection. In particular, compounds for the treatment or prevention of RSV infection as a primary or secondary infection in patients as described above is contemplated herein.

In addition, RSV infection is often mistaken for human parainfluenza virus ("HPIV") and influenza virus infection. (Collins et al., 1996, *Virology* pp. 1313–1351, Raven Press). HPIVs are also paramyxoviruses and are a common cause of lower respiratory tract disease in young children and can also cause serious lower respiratory tract disease with repeat infection (e.g., pneumonia, bronchitis, and bronchiolitis) among the elderly and those with compromised immune systems. HPIVs are spread from respiratory secretions through close contact with infected persons or contact with contaminated surfaces or objects. Influenza viruses are divided into three types, designated A, B, and C. Influenza types A and B are responsible for epidemics of respiratory illness that occur almost every winter and are often associated with increased rates for hospitalization and death. Influenza type C differs from types A and B in some important ways. Type C infection usually causes either a very mild respiratory illness or no symptoms at all; it does not cause epidemics and does not have the severe public health impact that influenza types A and B do. (See www.cdc.gov). Accordingly, novel therapeutics for the nonspecific treatment or prevention of respiratory illnesses caused by viral infection are also contemplated herein.

2.1 Benzimidazole Compounds

Specific benzimidazole compounds have been tested for antiviral activity. For example 2-(α-hydroxybenzyl)benzimidazole inhibits poliovirus type 1 in monkey kidney and HeLa cell cultures. A. C. Hollinshead et al., *J. Pharmacol. Exp. Ther.*, 1958, 123, 54. (For purposes of discussion, the benzimidazoles are numbered using the system illustrated in FIG. 1.) However, large concentrations of the specific benzimidazole was required to obtain any activity. Id. Other benzimidazole compounds directed to the hepatitis B virus were designed as nucleoside analogs, i.e., the benzimidazoles were produced containing a carbocyclic ring in place of the sugar residue. See U.S. Pat. No. 5,399,580. Accordingly, these compounds were substituted only with 5-membered rings at the 1 position of the benzimidazole ring. Id.

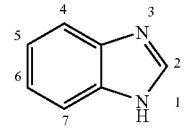

FIG. 1

Eli Lilly and Company studied substituted benzimidazole compounds with antiviral activity, however, activity was only shown for compounds having a benzophenone like structures, i.e., benzimidazoles with a carbonylbenzyl functional group at the 6 position. See U.S. Pat. No. 5,545,653. Although tested against poliovirus, rhinovirus, and coxsackie virus, toxic concentration levels were not determined, i.e., the cytotoxicity of the compounds was never studied to determine the safety of the compounds. These limited benzophenone like compounds were further studied by replacing the carbonyl functionality for acetylene and substituted acetylenes. See WO 96/40125. Activity, however, was shown only for acetylene substituted benzophenones that also required either a phenyl or thiazole ring at the 1 position of the benzimidazoles. Id.

In attempts to further enhance antiviral activity, others substituted benzimidazoles at the 2 position, however, these compounds were limited to benzotriazole substituted benzimidazoles. See WO 00/04900.

Compounds with a benzimidazole ring substituted at the 2-position of a benzimidazole ring have been studied for antiviral activity and it appears that these are the first class of compounds reported to inhibit all known serotypes of rhinovirus in cell culture. J. B. Scheleicher, et al., *Applied Microbiology*, 1972, 23, 113–116. However, success was dampened by the fact that not all compounds were active. Thus, there has yet to be developed a predictable structure-activity relationship with such 2-substituted compounds. Id. In particular, benzimidazole, 2-(α-hydroxybenzyl)benzimidazole, and 1,2-bis(2-benzimidazole)-1,2-ethanediol have been reported to be active antiviral agents against an assortment of picornaviruses. Id. However, there is considerable variation in the susceptibility of picornaviruses to any single antiviral compound and high concentrations were required to obtain any activity. Id.

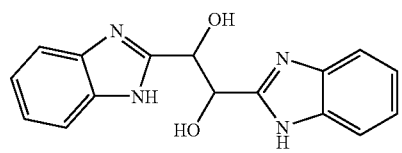

1,2-bis(2-benzimidazole)-1,2-ethanediol

Reportedly, compounds with two benzimidazole rings substituted at the 5-position are active against plaques of poliovirus type 1. W. R. Roderick, et al., "Bisbenzimidazoles. Potent Inhibitors of Rhinoviruses," *J. Med. Chem.*, 1972, 15, 655–658. In particular, 5-methoxybenzimidazole has been found to be a potent inhibitor of rhinoviruses producing 100% inhibition of the cytopathic effect. Id. Substitution at the 5-position, however, does not guarantee effectiveness, as demonstrated by the lack of activity of the 5-chloro substituted benzimidazole. Id. Also, monobenzimidazoles with similar substitution patterns do not inhibit rhinoviruses, although some have been reported to inhibit poliovirus. Id. Accordingly, predicting the activity of benzimidazoles is complex and does not follow any established pattern. Id.

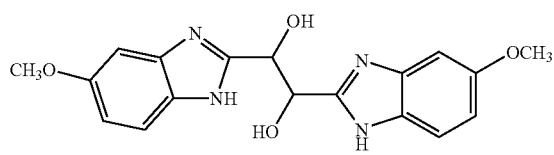

1,2-(5-methoxy-2-benzimidazole)-1,2-ethanediol

2-Benzyl-benzimidazole compounds substituted with alkyl amine groups at the 1 position allegedly posses anti-inflammatory and anti-pyretic properties. See U.S. Pat. No. 3,394,141. However, these compounds have not shown any antiviral activity.

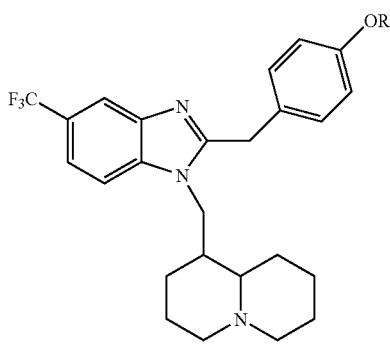

2-Benzyl-benzimidazole

Although some benzimidazole compounds posses antiviral activity, structure reactivity predictability is unknown. More importantly, benzimidazole compounds having a second benzimidazole ring at the 2 position have shown variable antiviral activity; thus, it appears that studies did not progress to include toxicity. Clearly, there is a great need for potent and non-toxic antiviral compounds, particularly, anti-RSV compounds. The benzimidazole compounds of the present invention have enhanced antiviral activity with low cytotoxicity, and they are readily synthesized from standard starting materials.

3. SUMMARY OF THE INVENTION

The invention encompasses the discovery of a novel class of benzimidazoles that are potent and selective antivirals. In particular, the compounds of the invention are selective for virally infected cells and thus have little or no cytotoxicity for healthy or uninfected cells. In preferred embodiments, the benzimidazole compounds demonstrate high inhibitory activity against viruses and low cytotoxicity activity against host cells. Such compounds are particularly useful in vivo for the treatment or prevention of viral-mediated diseases or infections. Accordingly, the present invention relates to benzimidazole compounds which have utility in the treatment, prevention or amelioration of symptoms associated with a viral infection. In particular, the invention encompasses benzimidazole compounds which have utility in the treatment, prevention or amelioration of symptoms associated with RSV infection. Additionally, the invention encompasses benzimidazole compounds which have utility in the inhibition or downregulation of HPIV or influenza virus replication. The benzimidazole compounds of the present invention are described below in detail.

Generally, the compounds of the invention are encompassed by the following formulas:

Formula I

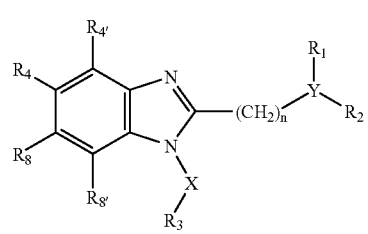

Formula II

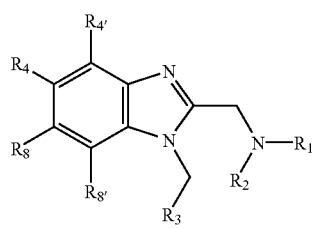

Formula III

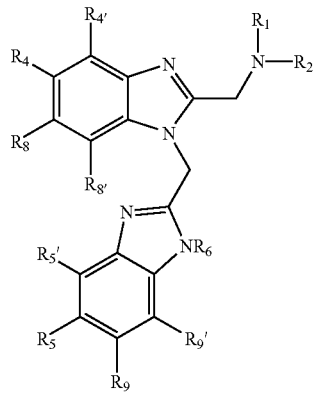

Formula IV

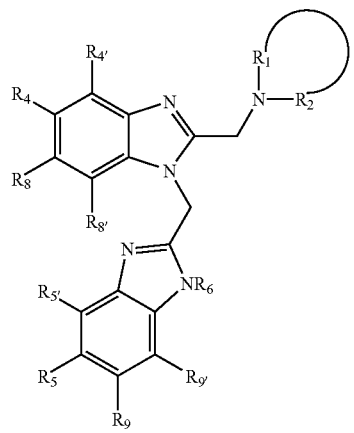

-continued

Formula V

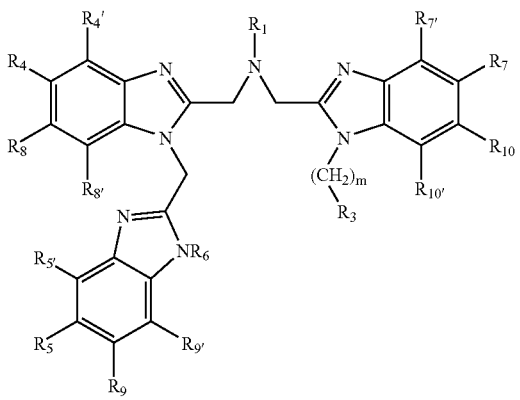

wherein $R_1$, $R_2$, $R_3$, $R_4$, $R_{4'}$, $R_5$, $R_{5'}$, $R_6$, $R_7$, $R_{7'}$, $R_8$, $R_{8'}$, $R_9$, $R_{9'}$, $R_{10}$, $R_{10'}$, X, Y, m and n are as defined below. Preferred embodiments are set forth below.

The present invention is based in part on novel benzimidazole compounds which have a utility for treating, preventing or ameliorating symptoms associated with viral infection, such as RSV infection and HPIV infection. Although not intending to be bound by any mechanism of action, the benzimidazole compounds are predicted to inhibit or interfere with viral membrane fusion associated events.

In certain embodiments, the invention encompasses methods for treating, preventing or ameliorating symptoms associated with a viral infection in a subject comprising administering to said subject one or more benzimidazole compounds of the invention. In another embodiment, the invention includes the treatment of viral infection by the inhibition of membrane fusion associated events. In other embodiments, the invention includes:
(a) methods of inhibiting viral transmission from cell to cell and/or replication; and
(b) methods of reducing viral titer and viral load.

The invention also encompasses methods for treating, preventing or ameliorating symptoms associated with RSV infection in a subject comprising administering to said subject one or more benzimidazole compounds of the invention. In a preferred embodiment, the benzimidazole is substituted in the 1-position by a methylene-benzimidazole moiety. In another preferred embodiment, the benzimidazole is substituted in the $R_4$ or $R_8$ position of formulas I, II, III, IV and V.

The present invention also provides pharmaceutical compositions comprising one or more benzimidazole compounds of the invention, including single unit dosage forms for oral administration, parenteral administration, intranasal administration, and by aerosol or other means directly into the lung. Thus, both solid and liquid formulations are encompassed as well as sterile compositions. Lyophilized powders suitable for reconstitution are also contemplated by the invention.

Also encompassed by the invention are methods of delivering one or more benzimidazole compounds, kits comprising one or more benzimidazole compounds or kits comprising one or more pharmaceutical compositions comprising one or more benzimidazole compounds, as well as therapeutic protocols comprising the administration of one or more benzimidazole compounds in combination with other prophylactic or therapeutic agents such as but not limited to antiviral, anti-inflammatory, anti-parasitic, anti-cancer and antibiotic agents.

3.1 Definitions

As used herein, the terms used have the following meaning:

As used herein, unless otherwise specified the term "alkyl" means a straight chain or branched saturated hydrocarbon moiety. An alkyl group can be unsubstituted or substituted. Unsaturated alkyl groups include alkenyl groups and alkynyl groups, which are discussed below.

As used herein, unless otherwise specified the term "alkenyl group" means a monovalent unbranched or branched hydrocarbon chain having one or more double bonds therein. The double bond of an alkenyl group can be unconjugated or conjugated to another unsaturated group. An alkenyl group can be unsubstituted or substituted.

As used herein, unless otherwise specified the term "alkynyl group" means a monovalent unbranched or branched hydrocarbon chain having at least one triple bond therein. The triple bond of an alkynyl group can be unconjugated or conjugated to another unsaturated group. An alkynyl group can be unsubstituted or substituted.

As used herein, unless otherwise specified the term "halogen" means fluorine, chlorine, bromine, or iodine.

As used herein, unless otherwise specified the term "alkyl sulfonyl" means -Alkyl-$SO_3$H or —$SO_3$-alkyl, wherein alkyl is defined as above.

As used herein, unless otherwise specified the term "carboxyl" means —COOH.

As used herein, unless otherwise specified the term "alkoxy" means —O-(alkyl), wherein alkyl is defined above.

As used herein, unless otherwise specified the term "alkoxycarbonyl" means —C(=O)O-(alkyl), wherein alkyl is defined above.

As used herein, unless otherwise specified the term "alkoxy alkyl" means -(alkyl)-O-(alkyl), wherein each "alkyl" is independently an alkyl group as defined above.

As used herein, unless otherwise specified the term "aryl" means a carbocyclic aromatic ring containing from 5 to 14 ring atoms. The ring atoms of a carbocyclic aryl group are all carbon atoms, such as, phenyl, tolyl, anthracenyl, fluorenyl, indenyl, azulenyl, and naphthyl, as well as benzo-fused carbocyclic moieties such as 5,6,7,8-tetrahydronaphthyl and the like. A carbocyclic aryl group can be unsubstituted or substituted.

As used herein, unless otherwise specified the term "heteroaryl" means a carbocyclic aromatic ring containing from 5 to 14 ring atoms and the ring atoms contain at least one heteroatom, preferably 1 to 3 heteroatoms, independently selected from nitrogen, oxygen, or sulfur. Heteroaryl ring structures include compounds having one or more ring structures such as mono-, bi-, or trycylic compounds. Illustrative examples of heteroaryl groups are pyridinyl, pyridazinyl, pyrimidyl, pyrazinyl, benzimidazolyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isothiazolyl, thiazolyl, furyl, phienyl, isoxazolyl, oxadiazolyl, and oxazolyl. A heteroaryl group can be unsubstituted or substituted.

As used herein, unless otherwise specified the term "aryloxy" means —O-aryl group, wherein aryl is as defined above. An aryloxy group can be unsubstituted or substituted.

As used herein, unless otherwise specified the term "arylalkyl" means -(alkyl)-(aryl), wherein alkyl and aryl are defined above.

As used herein, unless otherwise specified the term "arylalkyloxy" means —O-(alkyl)-(aryl), wherein alkyl and aryl are defined above.

As used herein, unless otherwise specified the term "cycloalkyl" means a monocyclic or polycyclic saturated ring comprising carbon and hydrogen atoms and having no carbon-carbon multiple bonds. A cycloalkyl group can be unsubstituted or substituted. Preferably, the cycloalkyl group is a monocyclic ring or bicyclic ring.

As used herein, unless otherwise specified the term "heterocyclyl" means a monocyclic or polycyclic ring comprising carbon and hydrogen atoms, optionally having 1 or 2 multiple bonds, and the ring atoms contain at least one heteroatom, preferably 1 to 3 heteroatoms, independently selected from nitrogen, oxygen, and sulfur. Heterocyclyl ring structures include compounds having one or more ring structures such as mono-, bi-, or trycylic compounds. Preferably, the heterocyclyl group is a monocyclic ring or bicyclic ring. Illustrative examples include, but are not limited to, oxiranyl, 2H-pyranyl, 4H-pyranyl, parathiazinyl, pyrazolidinyl, imidazolinyl, imidazolidinyl, piperidinyl, piperazinyl, and morpholinyl. A heterocyclyl ring can be unsubstituted or substituted.

As used herein, unless otherwise specified the term "cycloalkyloxy" means —O-(cycloalkyl), wherein cycloalkyl is defined above.

As used herein, unless otherwise specified the term "cycloalkylalkyloxy" means —O-(alkyl)-(cycloalkyl), wherein cycloalkyl and alkyl are defined above.

As used herein, unless otherwise specified the term "aminoalkoxy" means —O-(alkyl)-NH$_2$, wherein alkyl is defined above.

As used herein, unless otherwise specified the term "alkylamino" means —NH(alkyl) or —N(alkyl)(alkyl), wherein alkyl is defined above.

As used herein, unless otherwise specified the term "arylamino" means —NH(aryl), wherein aryl is defined above.

As used herein, unless otherwise specified the term "arylalkylamino" means —NH-(alkyl)-(aryl), wherein alkyl and aryl are defined above.

As used herein, unless otherwise specified the term "cycloalkylamino" means —NH-(cycloalkyl), wherein cycloalkyl is defined above.

As used herein, unless otherwise specified the term "aminoalkyl" means -(alkyl)-NH$_2$, wherein alkyl is defined above.

As used herein, unless otherwise specified the term "alkylaminoalkyl" means -(alkyl)-NH(alkyl) or -(alkyl)-N(alkyl)(alkyl), wherein each "alkyl" is independently an alkyl group defined above.

As used herein, the term "pharmaceutically acceptable salts" refer to salts of compounds of Formula I–XIV. prepared from pharmaceutically acceptable non-toxic acids or bases including inorganic acids and bases and organic acids and bases. Suitable pharmaceutically acceptable base addition salts for the compound of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include xinofoate, hydrochloride mesylate, zinc, potassium, or iron salts. In certain embodiments, both water-soluble and water-insoluble salts will be useful based on the mode of administration. Thus, the term "pharmaceutically acceptable salt(s)" of a compound of Formula I–XIV is intended to encompass any and all acceptable salt forms.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives and metabolites of Compound A that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Prodrugs can typically be prepared using well-known methods, such as those described by 1 Burger's Medicinal Chemistry and Drug Discovery, 172–178, 949–982 (Manfred E. Wolff ed., 5th ed. 1995).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters. Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

The term "human infant" as used herein refers to a human less than 24 months, preferably less than 16 months, less than 12 months, less than 6 months, less than 3 months, less than 2 months, or less than 1 month of age.

The term "human infant born prematurely" as used herein refers to a human born at less than 40 weeks gestational age, preferably less than 35 weeks gestational age, who is less than 6 months old, preferably less than 3 months old, more preferably less than 2 months old and most preferably less than 1 month old.

As used herein, unless otherwise specified, a "therapeutically effective amount" refers to that amount of the compound sufficient to result in amelioration of one or more symptoms of a disease. The term is also meant to include the amount of the compound sufficient to result in inhibition of or interference with membrane fusion events, viral entry, viral replication or viral infection. The term also encompasses the inhibition of viral transmission or prevention of viral establishment in its host. One such measure is reduction in viral load or viral pathogenesis or decrease in mortality and/or morbidity.

As used herein, unless otherwise specified, a "prophylactically effective amount" refers to that amount of the compound sufficient to result in the prevention of the onset or recurrence of symptoms of an infection. The term is also meant to include the amount of the compound sufficient to result in the prevention of membrane fusion events, viral entry, viral replication or viral infection. The term also encompasses the prevention of viral transmission or viral establishment in its host.

As used herein, unless otherwise specified, "inhibition of membrane fusion associated events", "anti-membrane fusion capability" and "antifusogenic" refer to the ability to block, reduce or prevent the occurrence of viral fusion with a host cell, or viral binding and/or attachment to a host cell receptor. The terms also refer to a compound's ability to inhibit or reduce the level of membrane fusion events between two or more moieties relative to the level of membrane fusion which occurs between said moieties in the absence of the compound. The moieties may be, for example, cell membranes or viral structures. Also encompassed by the terms are the ability of a compound to interfere with or inhibit viral entry into its host cell.

As used herein, unless otherwise specified, the term "antiviral activity" is meant to include partial and total inhibition of viral replication as well as decreases in the rate of viral replication. The term antiviral activity can also refer to any activity that results in the reduced function, activity or expression of a virus. Antiviral activity also refers to the prevention by down-regulation or inhibition of a protein required in the viral fusion pathway or the viral replication pathway or by interference with membrane fusion associated events. A compound with antiviral activity can interfere with or inactivate or destroy viral replication or infectivity. Accordingly, the term includes references to the compound's ability to inhibit viral infection of cells, via, for example, cell-cell fusion or free virus infection. Such infection may involve membrane fusion, as occurs in the case of enveloped viruses, or some other fusion event involving a viral structure and a cellular structure (e.g., such as the fusion of a viral pilus and bacterial membrane during bacterial conjugation). A compound with antiviral activity can also interfere with or inhibit or prevent viral entry into a host, viral transmission to a host, or viral establishment in its host. One skilled in the art could readily measure antiviral activity by a reduction in viral load or viral pathogenesis or decrease in mortality and/or morbidity.

4. DETAILED DESCRIPTION OF THE INVENTION

4.1 Benzimidazole Compounds

The present invention encompasses benzimidazole compounds, preferably, di-substituted benzimidazole compounds substituted at the 1- and 2-positions, preferably via an alkyl, or more preferably substituted with a methylenebenzimidazole. The compounds of the invention encompass compounds with antiviral activity and low cytotoxicity. In one embodiment, the present invention encompasses compounds of the general Formula I:

Formula I

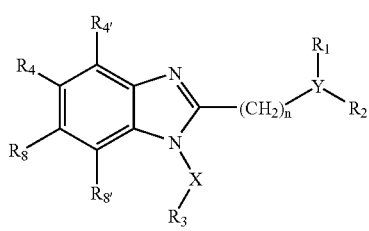

or a pharmaceutically-acceptable prodrug, salt, solvate including hydrate, clathrate, enantiomer, diastereomer, racemate, or mixture of stereoisomers thereof, wherein:

$R_1$ and $R_2$ are each independently: hydrogen, saturated or unsaturated straight or branched substituted or unsubstituted alkyl, substituted or unsubstituted cycloalkyl, substituted or unsubstituted heterocycloalkyl, substituted or unsubstituted heterocycloaryl; substituted or unsubstituted aryl, substituted or unsubstituted heteroaryl, or substituted or unsubstituted arylalkyl; wherein, if present, the substituent is at least one alkanoyl, imide, alkyl, hydroxy, halide, methoxy, ethoxy, carboxylic acid, cyano, amine, amide, alkylamine, acetal, acetylene, aminal, amino acid, amino acid ester, azo, diazo, azide, carbamate, carboxylic acid ester, carboalkoxy ester, cyanohydrin, diazonium salt, glucoside, glucuronide, halocarbon, polyhalocarbon, halocarbonoxy, polyhalocarbonoxy, hydroxylamine, ketone, lactone, nitrile, nitrile oxide, N-oxides, nucleoside linked, oxime, phosphate, phosphinate, phosphonate, phosphonic acid, quaternary ammonium salt, sulfoxide, sulfone, sulfonate ester, sulfinate ester, sulfonic acid, thioacetal, thiocarboxylic acid, thiol, thioaryl, or $R_1$ and $R_2$ may be joined to form a substituted or unsubstituted ring including a heterocycloalkyl, heterocycloaryl or heteroaryl group;

preferably, $R_1$ and $R_2$ are each independently $C_1$–$C_8$ saturated or unsaturated straight or branched substituted or unsubstituted alkyl, substituted or unsubstituted 3 to 8 membered cycloalkyl, substituted or unsubstituted 5 to 16 membered aryl, substituted or unsubstituted 5 to 10 membered arylalkyl, substituted or unsubstituted 4 to 12 membered heterocycloalkyl or heteroaryl group having at least one oxygen, sulfur, or nitrogen atom within the ring, wherein, if present, the substituent is least one $C_1$–$C_4$ alkyl, hydroxy, halide, methoxy, ethoxy, carboxylic acid, ester, amine, or $C_1$–$C_4$ alkylamine;

more preferably, $R_1$ and $R_2$ are each independently $C_1$–$C_4$ saturated or unsaturated straight or branched substituted or unsubstituted alkyl, substituted or unsubstituted 3 to 6 membered cycloalkyl, substituted or unsubstituted 5 to 8 membered aryl, substituted or unsubstituted 5 to 8 membered arylalkyl, or substituted or unsubstituted 4 to 9 membered heterocycloalkyl or heteroaryl with at least one oxygen, sulfur, or nitrogen atom within the ring, wherein, if present, the substituent is least one $C_1$–$C_4$ alkyl, hydroxy, fluoride, chloride, bromide, methoxy, ethoxy, carboxylic acid, ester, amine, or $C_1$–$C_4$ alkylamine; and most preferably, $R_1$ and $R_2$ are each independently benzyl, cyclopentyl, cyclohexyl, isopropyl, propyl, butyl, methylene cyclopropyl, methylene cyclobutyl, benzimidazolyl, methylene benzimidazolyl, or $R_1$ and $R_2$ are attached to form a pyrrolidinyl or piperidinyl ring.

$R_3$ is hydrogen, halide, saturated or unsaturated straight or branched substituted or unsubstituted alkyl, hydroxy, substituted or unsubstituted alkoxy, substituted or unsubstituted aryl, substituted or unsubstituted arylalkyl, substituted or unsubstituted heterocycloalkyl, or substituted or unsubstituted heteroaryl; wherein, if present the substiuent is at least one alkanoyl, imide, alkyl, hydroxy, halide, methoxy, ethoxy, carboxylic acid, amine, amide, alkylamine, acetal, acetylene, aminal, amino acid, amino acid ester, azo, diazo, azide, carbamate, carboxylic acid ester, carboalkoxy ester, cyanohydrin, diazonium salt, glucoside, glucuronide, halocarbon, polyhalocarbon, halocarbonoxy, polyhalocarbonoxy, hydroxylamine, ketone, lactone, nitrile, nitrile oxide, N-oxides, nucleoside linked, oxime, phosphate, phosphinate, phosphonate, phosphonic acid quaternary ammonium salt, sulfoxide, sulfone, sulfonate ester, sulfinate ester, sulfonic acid, thioacetal, thiocarboxylic acid, thiol, or thioaryl;

preferably, $R_3$ is hydrogen, straight chain or branched substituted or unsubstituted $C_1$–$C_8$ alkyl or unsaturated alkyl, substituted or unsubstituted 3 to 8 membered cycloalkyl, substituted or unsubstituted 5 to 16 membered aryl, substituted or unsubstituted 5 to 10 membered arylalkyl, substituted or unsubstituted 4 to 12 membered heterocycloalkyl or heteroaryl having at least one oxygen, sulfur, or nitrogen atom within the ring, wherein the substituent is at least one hydroxy, fluoride, chloride, bromine, $C_1$–$C_4$ alkoxy, $C_1$–$C_4$ sulfide, $C_1$–$C_4$ sulfonyl, nitro, carboxylic acid, ester, amine, or $C_1$–$C_4$ alkylamine;

more preferably, $R_3$ is a substituted or unsubstituted $C_1$–$C_4$ straight chain or branched alkyl or unsaturated alkyl, substituted or unsubstituted 3 to 6 membered cycloalkyl, substituted or unsubstituted 5 to 12 membered aryl, substituted or unsubstituted 6 to 12 membered arylalkyl, substituted or unsubstituted 4 to 12 membered heterocycloalkyl or heteroaryl with at least one oxygen, sulfur, or nitrogen atom within the ring, wherein, if present, the substituent is at least one hydroxy, fluoride, chloride, bromide, $C_1$–$C_4$ alkyl, $C_1$–$C_4$ alkoxy, $C_1$–$C_4$ sulfide, $C_1$–$C_4$ sulfonyl, nitro, carboxylic acid, ester, amine, or $C_1$–$C_4$ alkylamine; and most preferably, $R_3$ is a substituted or unsubstituted phenyl, substituted or unsubstituted pyrrolidinyl, substituted or unsubstituted pyrrolyl, substituted or unsubstituted piperidinyl, substituted or unsubstituted pyridinyl, substituted or unsubstituted quinolinyl, substituted or unsubstituted acridinyl, substituted or unsubstituted thiazolyl, substituted or unsubstituted benzimidazolyl, substituted or unsubstituted benzodioxanyl, substituted or unsubstituted phenylphenolyl, wherein, if present, the substituent is at least one $C_1$–$C_4$ alkyl, $C_1$–$C_4$ alkoxy, $C_1$–$C_4$ sulfide, $C_1$–$C_4$ sulfonyl, nitro, fluoride, chloride, or bromide.

$R_4$, $R_{4'}$, $R_8$, and $R_{8'}$ are each independently hydrogen, halide, saturated or unsaturated straight or branched substituted or unsubstituted alkyl, hydroxy, substituted or unsubstituted alkoxy, substituted or unsubstituted aryl, substituted or unsubstituted arylalkyl, substituted or unsubstituted heterocycloalkyl, substituted or unsubstituted heteroaryl; wherein, if present the substituent is at least one alkanoyl, imide, amine, alkylamine, amide, carboxylic acid, ester, nitro, sulfide, sulfonyl, sulfonamide, acetal, acetylene, aminal, amino acid, amino acid ester, azo, diazo, azide, carbamate, carboxylic acid ester, carboalkoxy ester, cyanohydrin, diazonium salt, glucoside, glucuronide, halocarbon, polyhalocarbon, halocarbonoxy, polyhalocarbonoxy, hydroxylamine, ketone, lactone, nitrile, nitrile oxide, N-oxides, nucleoside linked, oxime, phosphate, phosphinate, phosphonate, phosphonic acid, quaternary ammonium salt, sulfoxide, sulfone, sulfonate ester, sulfinate ester, sulfonic acid, thioacetal, thiocarboxylic acid, thiol, or thioaryl;

preferably, $R_4$, $R_{4'}$, $R_8$, and $R_{8'}$, are each independently hydrogen, $C_1$–$C_4$ alkyl, $C_1$–$C_4$ alkoxy, amine, $C_1$–$C_4$ alkylamine, carboxylic acid, ester, $C_1$–$C_4$ amide, halide, hydroxy, nitro, $C_1$–$C_4$ sulfide, $C_1$–$C_4$ sulfonyl, or sulfonamide;

more preferably, $R_4$ and $R_8$ are each independently hydrogen, $C_1$–$C_2$ alkyl, $C_1$–$C_2$ alkoxy, amine, $C_1$–$C_2$ alkylamine, fluoride, chloride, bromide, hydroxy, nitro, $C_1$–$C_2$ sulfide, or $C_1$–$C_2$ sulfonyl;

more preferably, $R_{4'}$ and $R_{8'}$ are each independently, hydrogen, $C_1$–$C_2$ alkyl, amine, $C_1$–$C_2$ alkylamine, $C_1$–$C_2$ alkoxy, carboxylic acid, $C_2$–$C_4$ ester, $C_1$–$C_2$ amide, or sulfonamide;

most preferably, $R_4$ and $R_8$ are each independently hydrogen, methyl, methoxy, thiomethyl, fluoride, chloride, nitro, or methylsulfonyl; and most preferably, $R_{4'}$ and $R_{8'}$ are each independently, hydrogen, methyl, methyl ester, ethyl ester, $C_1$–$C_2$ amide, carboxylic acid, methoxy, or sulfonamide.

X is a bond, straight chain or branched substituted or unsubstituted alkyl or unsaturated alkyl, -(alkyl)N—, -(alkyl)O—, —C=N—, carbonyl, phosphorus, or sulfur;

preferably, X is a bond, straight chain or branched substituted or unsubstituted $C_1$–$C_4$ alkyl, —($C_1$–$C_4$ alkyl)N—, —($C_1$–$C_4$ alkyl)O—, carbonyl, or sulfur;

more preferably, X is a bond, methylene, ethylene, or carbonyl; and most preferably, X is methylene.

Y is nitrogen, phosphorus, oxygen, or sulfur; wherein, if Y is oxygen or sulfur, $R_2$ is not present; preferably Y is nitrogen, or phosphorus; and more preferably, Y is nitrogen.

The "n" is an integer from 0 to about 4; preferably n is from 0 to 1; and more preferably, n is 1.

In another embodiment of the compounds of Formula I, $R_{4'}$, and $R_{8'}$ are hydrogen. In another embodiment of the compounds of Formula I, $R_4$, $R_{4'}$, $R_8$, and $R_{8'}$ are all hydrogen. In yet another embodiment of the compounds of Formula I, at least one of $R_4$, $R_{4'}$, $R_8$, or $R_{8'}$ is not hydrogen. In yet another embodiment of the compounds of Formula I, at least two of $R_4$, $R_{4'}$, $R_8$, and $R_{8'}$ are not hydrogen. In another embodiment of the compounds of Formula I, at least three of $R_4$, $R_{4'}$, $R_8$, and $R_{8'}$ are not hydrogen.

With the proviso that compounds of Formula I do not include a compound where $R_1$, $R_2$, $R_3$, $R_4$, $R_{4'}$, $R_8$, $R_{8'}$ are hydrogen, X is a bond, and n=0 or 1; or a compound where $R_3$, $R_4$, $R_{4'}$, $R_8$, and $R_{8'}$ are hydrogen, X is a bond, n=0, one of $R_1$ or $R_2$ is a hydrogen, and the other is a 4-piperidinyl or N-substituted 4-piperidinyl.

Preferred compounds include:

1-(1H-Benzimidazol-2-ylmethyl)-2-morpholin-4-ylmethyl-1H-benzimidazole-5-carboxylic acid methyl ester;

1-(1H-Benzimidazol-2-ylmethyl)-2-morpholin-4-ylmethyl-1H-benzimidazole-6-carboxylic acid methyl ester;

{1-[1-(1H-Benzoimidazol-2-ylmethyl)-1H-benzoimidazol-2-ylmethyl]-piperidin-3-yl}-methanol;

{1-[1-(1H-Benzoimidazol-2-ylmethyl)-1H-benzoimidazol-2-ylmethyl]-pyrrolidin-2-yl}-methanol;

2-{1-[1-(1H-benzoimidazol-2-ylmethyl)-1H-benzoimidazol-2-ylmethyl]-piperidin-2-yl}-ethanol;

[1,2,4]Oxadiazol-3-ylmethyl-2-[4-(3-trifluoromethyl-phenyl)-piperazin-1-ylmethyl]-1H-benzoimidazole;

1-[1-(1H-Benzoimidazol-2-ylmethyl)-1H-benzoimidazol-2-ylmethyl]-4-(3-trifluoromethyl-phenyl)piperazine;

1-[1-(1H-Benzoimidazol-2-ylmethyl)-1H-benzoimidazol-2-ylmethyl]-4-(4-trifluoromethyl-phenyl)piperazine;

1-[1-(1H-Benzoimidazol-2-ylmethyl)-1H-benzoimidazol-2-ylmethyl]-4-pyridin-2-ylpiperazine;

(R)-{1-[1-(1H-Benzoimidazol-2-ylmethyl)-1H-benzoimidazol-2-ylmethyl]-pyrrolidin-2-yl }-methanol;

(S)-1-[1-(1H-Benzoimidazol-2-ylmethyl)-1H-benzoimidazol-2-ylmethyl]-pyrrolidine-2-carboxylic acid methyl ester;

(S)-1-[1-(1H-Benzoimidazol-2-ylmethyl)-1H-benzoimidazol-2-ylmethyl]-pyrrolidine-2-carboxylic acid amide;

2-{4-[1-(1H-Benzoimidazol-2-ylmethyl)-1H-benzoimidazol-2-ylmethyl]-piperazin-1-yl}-acetamide;

1-[1-(1H-Benzoimidazol-2-ylmethyl)-1H-benzoimidazol-2-ylmethyl]-piperidine-3-carboxylic acid 1-(1H-benzoimidazol-2-ylmethyl)-1H-benzoimidazol-2-ylmethyl ester; and 1-[1-(1H-Benzoimidazol-2-ylmethyl)-1H-benzoimidazol-2-ylmethyl]-pyrrolidine-2-carboxylic acid 1-(1H-benzoimidazol-2-ylmethyl)-1H-benzoimidazol-2-ylmethyl ester.

A few examples of compounds of the invention are depicted in Tables 1–8 for illustration and not limitation. Because of possible discrepancies in using chemical nomenclature where structures are provided for compounds or moieties the structure controls the definition of the compound or moiety, if there is a discrepancy with the chemical name. Each compound in Tables 1–8 has been prepared, isolated, purified, and tested for antiviral activity and cytotoxicity as discussed below. The drawings described below use standard chemical nomenclature. For example, terminal lines represent methyl groups and corners represent saturated carbons unless otherwise indicated:

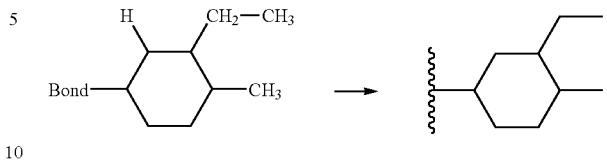

A wavy line perpendicular to a terminal line represents a point of bond attachment.

TABLE 1

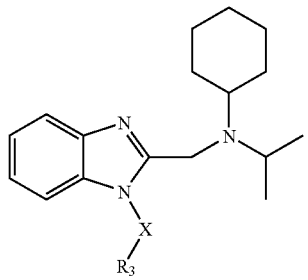

Formula VII

| Cmpd. # | $R_3$ | X | PRA ($IC_{50}$) μg/mL | XTT ($CC_{50}$) μg/mL | Selective Index |
|---|---|---|---|---|---|
| 1 | quinolin-2-yl | —$CH_2$— | 5.16 | 50 | 9.69 |
| 2 | 2-methylthiazol-4-yl | —$CH_2$— | 2.28 | 50 | 21.93 |
| 3 | 3,5-dimethoxyphenyl | —$CH_2$— | 4.56 | 50 | 10.96 |
| 4 | 2-methylphenyl | C=O | 6.25 | 50 | 8 |
| 5 | 3-nitrophenyl | —$CH_2$— | 4.21 | 50 | 11.88 |

TABLE 1-continued
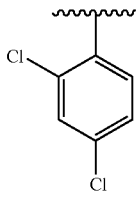
Formula VII
| Cmpd. # | R₃ | X | PRA (IC$_{50}$) μg/mL | XTT (CC$_{50}$) μg/mL | Selective Index |
|---|---|---|---|---|---|
| 6 | 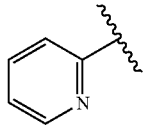 | —CH₂— | 3 | 50 | 16.67 |
| 7 | 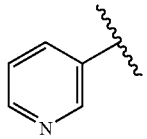 | —CH₂— | 0.8 | 100 | 125 |
| 8 | 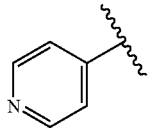 | —CH₂— | 1.1 | 100 | 91 |
| 9 | 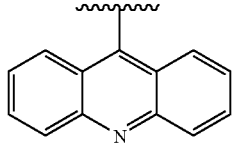 | —CH₂— | 1.6 | 100 | 63 |
| 10 | 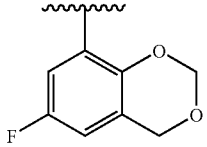 | —CH₂— | 1.7 | 100 | 59 |
| 11 | 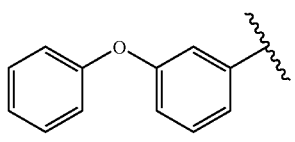 | —CH₂— | 0.67 | 26 | 39 |
| 12 | 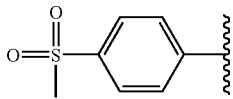 | —CH₂— | 1.98 | 100 | 51 |
| 13 |  | —CH₂— | 0.9 | 100 | 111 |

TABLE 1-continued

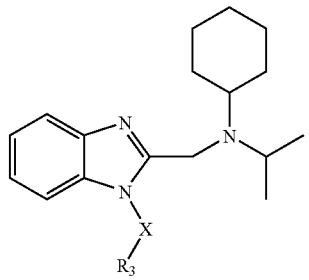

Formula VII

| Cmpd. # | R₃ | X | PRA (IC$_{50}$) µg/mL | XTT (CC$_{50}$) µg/mL | Selective Index |
|---|---|---|---|---|---|
| 14 | (4-methylthiophenyl) | —CH₂— | 1.6 | 30 | 19 |

In another embodiment, the 2-position of the benzimidazole ring is substituted with an aminoalkyl group, with reference to Formula I, X is methylene, Y is nitrogen, and n is 1, thus, in another embodiment, the present invention encompasses compounds of the general Formula II:

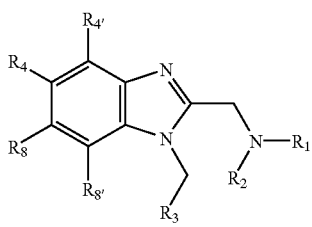

Formuula II or a pharmaceutically-acceptable prodrug, salt, solvate including hydrate, clathrate, enantiomer, diastereomer, racemate, or mixture of stereoisomers thereof, wherein:

$R_1$ and $R_2$ are each independently: a straight or branched substituted or unsubstituted alkyl or unsaturated alkyl, substituted or unsubstituted cycloalkyl, substituted or : unsubstituted heterocycloalkyl, substituted or unsubstituted aryl, substituted or unsubstituted heteroaryl, substituted or unsubstituted arylalkyl, acetal, acetylene, aminal, amino acid, amino acid ester, azo, diazo, azide, carbamate, carboxylic acid ester, carboalkoxy ester, cyanohydrin, diazonium salt, glucoside, glucuronide, halocarbon, polyhalocarbon, halocarbonoxy, polyhalocarbonoxy, hydroxylamine, ketone, lactone, nitrile, nitrile oxide, N-oxides, nucleoside linked, oxime, phosphate, phosphinate, phosphonate, phosphonic acid, quaternary ammonium salt, sulfoxide, sulfone, sulfonate ester, sulfinate ester, sulfonic acid, thioacetal, thiocarboxylic acid, thiol, thioaryl, or $R_1$ and $R_2$ may be joined to form a ring including a heterocycloalkyl or heteroaryl group;

preferably, $R_1$ and $R_2$ are each independently: $C_1$–$C_8$ straight chain or branched alkyl or substituted alkyl or unsaturated alkyl, substituted or unsubstituted 3 to 8 membered cycloalkyl, substituted or unsubstituted 5 to 16 membered aryl, substituted or unsubstituted 5 to 10 membered arylalkyl, 4 to 12 membered heterocycloalkyl or heteroaryl with at least one oxygen, sulfur, or nitrogen atom within the ring, wherein, if present, the substituent is at least one hydroxy, halide, methoxy, ethoxy, carboxylic acid, ester, amine, or alkylamine;

more preferably, $R_1$ and $R_2$ are each independently: $C_1$–$C_4$ straight chain or branched alkyl or unsaturated alkyl, substituted or unsubstituted 3 to 6 membered cycloalkyl, substituted or unsubstituted 5 to 6 membered aryl, substituted or unsubstituted 5 to 8 membered arylalkyl, or 4 to 8 membered heterocycloalkyl or heteroaryl with at least one oxygen, sulfur, or nitrogen atom within the ring, wherein, if present, the substituent is at least one hydroxy, fluoride, chloride, bromide, methoxy, ethoxy, carboxylic acid, ester, amine, or $C_1$–$C_4$ alkylamine; and most preferably, $R_1$ and $R_2$ are each independently: benzyl, cyclopentyl, cyclohexyl, isopropyl, propyl, butyl, methylene cyclopropyl, methylene cyclobutyl, or $R_1$ and $R_2$ are attached to form a pyrrolidinyl or piperidinyl ring.

$R_3$ is hydrogen, halide, straight chained or branched substituted or unsubstituted alkyl or unsaturated alkyl, hydroxy, substituted or unsubstituted alkoxy, substituted or unsubstituted cycloalkyl, substituted or unsubstituted aryl, substituted or unsubstituted arylalkyl, substituted or unsubstituted heterocycloalkyl, or substituted or unsubstituted heteroaryl;

preferably, $R_3$ is hydrogen, $C_1$–$C_8$ straight chain or branched substituted or unsubstituted alkyl or unsaturated alkyl, substituted or unsubstituted 3 to 8 membered cycloalkyl, substituted or unsubstituted 5 to 16 membered aryl, substituted or unsubstituted 5 to 10 membered arylalkyl, substituted or unsubstituted 4 to 12 membered heterocycloalkyl or heteroaryl with at least one oxygen, sulfur, or nitrogen atom within the ring, wherein, if present, the substituent is at least one hydroxy, halide, $C_1$–$C_4$ alkyl, $C_1$–$C_4$ alkoxy, $C_1$–$C_4$ sulfide, $C_1$–$C_4$ sulfonyl, nitro, carboxylic acid, ester, amine, or $C_1$–$C_4$ alkylamine;

more preferably, $R_3$ is $C_1$–$C_4$ straight chain or branched alkyl or unsaturated alkyl, substituted or unsubstituted 3 to 6 membered cycloalkyl, substituted or unsubstituted 5 to 12 membered aryl, substituted or unsubstituted 5 to 12 membered arylalkyl, or 4 to 12 membered heterocycloalkyl or heteroaryl with at least one oxygen, sulfur, or nitrogen atom within the ring, wherein, if present, the substituent is at least one hydroxy, halide, $C_1$–$C_4$ alkyl, $C_1$–$C_4$ alkoxy, $C_1$–$C_4$ sulfide, $C_1$–$C_4$ sulfonyl, nitro, carboxylic acid, ester, amine, or $C_1$–$C_4$ alkylamine; and most preferably, $R_3$ is a substituted or unsubstituted phenyl, substituted or unsubstituted pyrrolidinyl, substituted or unsubstituted pyrrolyl, substituted or unsubstituted piperidinyl, substituted or unsubstituted pyridinyl, substituted or unsubstituted quinolinyl, substituted or unsubstituted acridinyl, substituted or unsubstituted thiazolyl, substituted or unsubstituted benzodioxanyl, substituted or unsubstituted benzimidazolyl, substituted or unsubstituted phenylphenolyl, wherein, if present, the substituent is at least one $C_1$–$C_4$ alkyl, $C_1$–$C_4$ alkoxy, $C_1$–$C_4$ sulfide, $C_1$–$C_4$ sulfonyl, nitro, fluoride, chloride, bromide, or iodide.

$R_4$, $R_{4'}$, $R_8$, and $R_{8'}$ are each independently hydrogen, halide, straight chained or branched substituted or unsubstituted alkyl or unsaturated alkyl, hydroxy, substituted or unsubstituted alkoxy, substituted or unsubstituted cycloalkyl, substituted or unsubstituted aryl, substituted or unsubstituted arylalkyl, substituted or unsubstituted heterocycloalkyl, or substituted or unsubstituted heteroaryl, amine, alkylamine, amide, carboxylic acid, ester, nitro, sulfide, sulfonyl, sulfonamide, acetal, acetylene, aminal, amino acid, amino acid ester, azo, diazo, azide, carbamate, carboxylic acid ester, carboalkoxy ester, cyanohydrin, diazonium salt, glucoside, glucuronide, halocarbon, polyhalocarbon, halocarbonoxy, polyhalocarbonoxy, hydroxylamine, ketone, lactone, nitrile, nitrile oxide, N-oxides, nucleoside linked, oxime, phosphate, phosphinate, phosphonate, phosphonic acid, quaternary ammonium salt, sulfoxide, sulfone, sulfonate ester, sulfinate ester, sulfonic acid, thioacetal, thiocarboxylic acid, thiol, or thioaryl;

preferably, $R_4$, $R_{4'}$, $R_8$, and $R_{8'}$ are each independently hydrogen, $C_1$–$C_4$ alkyl, $C_1$–$C_4$ alkoxy, amine, $C_1$–$C_4$ alkylamine, $C_1$–$C_4$ amide, carboxylic acid, ester, halide, hydroxy, nitro, $C_1$–$C_4$ sulfide, $C_1$–$C_4$ sulfonyl, or sulfonamide;

more preferably, $R_4$ and $R_8$ are each independently are hydrogen $C_1$–$C_2$ alkyl, $C_1$–$C_2$ alkoxy, amine, $C_1$–$C_2$ alkylamine, fluoride, chloride, bromide, hydroxy, nitro, $C_1$–$C_2$ sulfide, or $C_1$–$C_2$ sulfonyl;

more preferably, $R_{4'}$ and $R_{8'}$ are each independently, hydrogen, $C_1$–$C_2$ alkyl, amine, $C_1$–$C_2$ alkylamine, $C_1$–$C_2$ amide, carboxylic acid, $C_2$–$C_4$ ester, or sulfonamide;

most preferably, $R_4$ and $R_8$ are each independently are hydrogen, methyl, methoxy, thiomethyl, fluorine, chlorine, nitro, or methylsulfonyl; and most preferably, $R_{4'}$ and $R_{8'}$ are each independently, hydrogen, methyl, methyl ester, ethyl ester, $C_1$–$C_2$ amide, carboxylic acid, methoxy, or sulfonamide.

In another embodiment of the compounds of Formula II, $R_{4'}$ and $R_{8'}$ are hydrogen. In yet another embodiment of the compounds of Formula II, $R_4$, $R_{4'}$, $R_8$, and $R_{8'}$ are hydrogen. In yet another embodiment of the compounds of Formula II, at least one of $R_4$, $R_{4'}$, $R_8$, or $R_{8'}$ is not hydrogen. In another embodiment of the compounds of Formula II, at least two of $R_4$, $R_{4'}$, $R_8$, and $R_{8'}$ are not hydrogen. In another embodiment of the compounds of Formula II, at least three of $R_4$, $R_{4'}$, $R_8$, and $R_{8'}$ are not hydrogen.

In a further embodiment of the invention, the compounds of the invention include compounds described in the formulas of the headers of Tables 2, 3, 4, and 5, additional non-limiting specific compounds are contained within the tables. The specific compounds are for illustration and not limitation. Each compound in Tables 2–5 has been prepared, isolated, purified, and tested for antiviral activity and cytotoxicity as discussed below.

TABLE 2

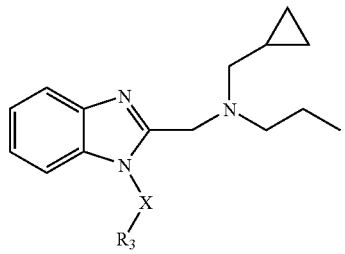

Formula VIII

| Cmpd. # | $R_3$ | X | PRA ($IC_{50}$) μg/mL | XTT ($CC_{50}$) μg/mL | Selective Index |
|---|---|---|---|---|---|
| 20 | quinolin-2-yl | —$CH_2$— | 3.25 | 50 | 15.38 |
| 21 | 2-methylthiazol-4-yl | —$CH_2$— | 2.14 | 50 | 23.36 |

TABLE 2-continued
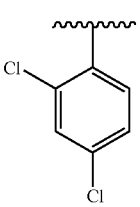
Formula VIII
| Cmpd. # | R₃ | X | PRA (IC$_{50}$) μg/mL | XTT (CC$_{50}$) μg/mL | Selective Index |
|---|---|---|---|---|---|
| 22 | 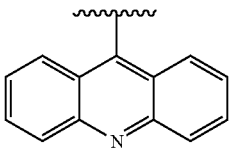 | —CH$_2$— | 4.5 | 50 | 11.11 |
| 23 | 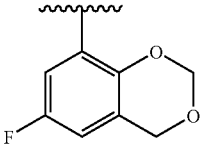 | —CH$_2$— | 1.8 | 101 | 56 |
| 24 | 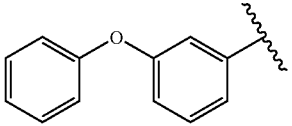 | —CH$_2$— | 0.85 | 82 | 96 |
| 25 | 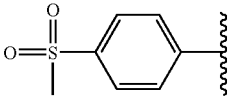 | —CH$_2$— | 1.8 | 101 | 56 |
| 26 | 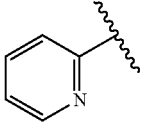 | —CH$_2$— | 1.2 | 97 | 83 |
| 27 | 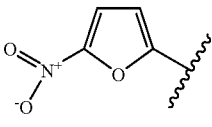 | —CH$_2$— | 0.56 | 100 | 179 |
| 28 |  | —CH$_2$— | 1.6 | | |

TABLE 3
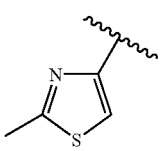
Formula IX
| Cmpd. # | R₃ | X | PRA (IC$_{50}$) μg/mL | XTT (CC$_{50}$) μg/mL | Selective Index |
|---|---|---|---|---|---|
| 40 | 2-methylthiazol-4-yl | —CH$_2$— | 3.72 | 50 | 13.44 |
TABLE 3-continued
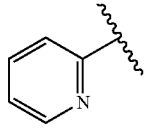
Formula IX
| Cmpd. # | R₃ | X | PRA (IC$_{50}$) μg/mL | XTT (CC$_{50}$) μg/mL | Selective Index |
|---|---|---|---|---|---|
| 41 | pyridin-2-yl | —CH$_2$— | 0.84 | 71 | 85 |
TABLE 4
Formula XI
| Cmpd. # | R₃ | X | PRA (IC$_{50}$) μg/mL | XTT (CC$_{50}$) μg/mL | Selective Index |
|---|---|---|---|---|---|
| 50 | quinolin-2-yl | —CH$_2$— | 3.56 | 50 | 14.04 |
| 51 | 2-methylthiazol-4-yl | —CH$_2$— | 2.05 | 50 | 24.39 |
| 52 | biphenyl-4-yl | —CH$_2$— | 4.42 | 50 | 11.31 |

TABLE 4-continued
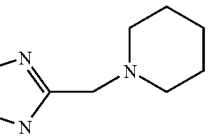
Formula XI
| Cmpd. # | R$_3$ | X | PRA (IC$_{50}$) μg/mL | XTT (CC$_{50}$) μg/mL | Selective Index |
|---|---|---|---|---|---|
| 53 | 2-methylphenyl | C=O | 3.85 | 50 | 12.99 |
| 54 | 5-nitrofuran-2-yl | —CH$_2$— | 1.2 | 97 | 83 |
| 55 | 2,4-dichlorophenyl | —CH$_2$— | 4.1 | 50 | 12.2 |
| 56 | pyridin-2-yl | —CH$_2$— | 2 | 100 | 50 |
| 57 | pyridin-3-yl | —CH$_2$— | 1.7 | 100 | 59 |
| 58 | pyridin-4-yl | —CH$_2$— | 1.3 | 100 | 77 |
| 59 | 6-fluoro-4H-benzo[1,3]dioxin-8-yl | —CH$_2$— | 1.4 | 100 | 71 |
| 60 | 4-(methylsulfonyl)phenyl | —CH$_2$— | 1.5 | 100 | 67 |

TABLE 4-continued
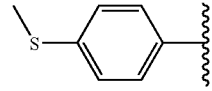
Formula XI
| Cmpd. # | R₃ | X | PRA (IC$_{50}$) μg/mL | XTT (CC$_{50}$) μg/mL | Selective Index |
|---|---|---|---|---|---|
| 61 | 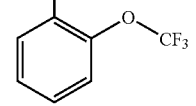 | —CH$_2$— | 1.3 | 20 | 15 |
| 62 | 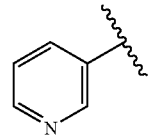 | —CH$_2$— | 1.3 | 34 | 26 |
TABLE 5
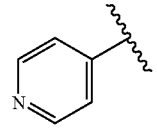
Formula XI
| Cmpd. # | R₃ | X | PRA (IC$_{50}$) μg/mL | XTT (CC$_{50}$) μg/mL | Selective Index |
|---|---|---|---|---|---|
| 70 | 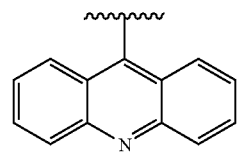 | —CH$_2$— | 0.37 | 100 | 270 |
| 71 | (4-pyridyl) | —CH$_2$— | 1.6 | 100 | 63 |
| 72 | (acridin-9-yl) | —CH$_2$— | 0.67 | 100 | 149 |

TABLE 5-continued
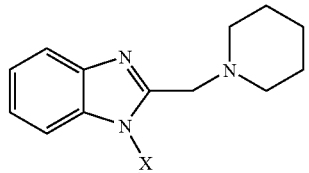
Formula XI
| Cmpd. # | R₃ | X | PRA (IC$_{50}$) μg/mL | XTT (CC$_{50}$) μg/mL | Selective Index |
|---|---|---|---|---|---|
| 73 | 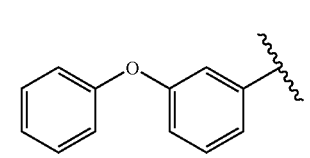 | —CH$_2$— | 1.8 | 101 | 56 |
| 74 | 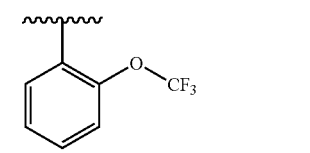 | —CH$_2$— | 1.4 | 10 | 7 |
| 75 | 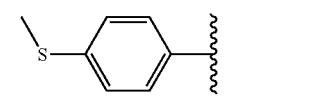 | —CH$_2$— | 0.93 | 24 | 26 |
| 76 | 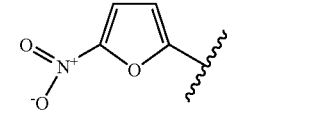 | —CH$_2$— | 1.8 | 11 | 6 |
| 77 | 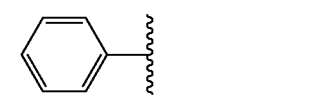 | —CH$_2$— | 1.5 | 100 | 67 |
| 78 | 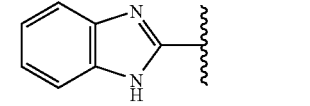 | —CH$_2$— | 0.43 | 10 | 24 |
| 79 |  | —CH$_2$— | 0.02 | 100 | 5000 |

In a preferred embodiment of the invention, with reference to Formula II, $R_3$ is a substituted or unsubstituted benzimidazole moiety, thus, the present invention encompasses compounds of the general Formula III:

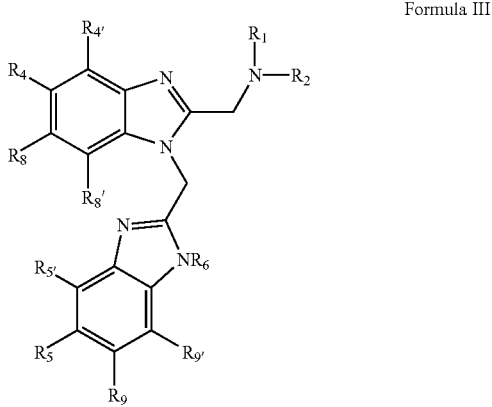

Formula III or a pharmaceutically-acceptable prodrug, salt, solvate including hydrate, clathrate, enantiomer, diastereomer, racemate, or mixture of stereoisomers thereof, wherein:

$R_1$ and $R_2$ are each independently: hydrogen, saturated or unsaturated straight or branched substituted or unsubstituted alkyl, substituted or unsubstituted alkoxy, substituted or unsubstituted alkylamino, substituted or unsubstituted cycloalkyl, substituted or unsubstituted heterocycloalkyl, substituted or unsubstituted aryl, substituted or unsubstituted arylalkyl, substituted or unsubstituted heterocycloaryl, substituted or unsubstituted heteroaryl, alkanoyl, or imide, wherein, if present, the substituent is at least one alkyl, alkanoyl, imide, alkoxy, carboxylic acid, amine, alkylamine, cyano, halide, hydroxy, nitro, thiol, acetal, acetylene, aminal, amino acid, amino acid ester, azo, diazo, azide, carbamate, carboxylic acid ester, carboalkoxy ester, cyanohydrin, diazonium salt, glucoside, glucuronide, halocarbon, polyhalocarbon, halocarbonoxy, polyhalocarbonoxy, hydroxylamine, lactone, nitrile, nitrile oxide, N-oxides, nucleoside linked, oxime, quaternary ammonium salt, sulfoxide, sulfone, sulfonate ester, sulfinate ester, sulfonic acid, thioacetal, thiocarboxylic acid, thiol, or thioaryl;

preferably, $R_1$ and $R_2$ are each independently straight chain or branched substituted or unsubstituted $C_1$–$C_{11}$ alkyl or unsaturated alkyl, $C_1$–$C_{12}$ alkoxy, substituted or unsubstituted $C_1$–$C_{11}$ alkylamino, substituted or unsubstituted 3 to 10 membered cycloalkyl, substituted or unsubstituted 3 to 10 membered heterocycloalkyl, substituted or unsubstituted 5 to 12 membered aryl, substituted or unsubstituted 5 to 12 membered arylalkyl, substituted or unsubstituted 4 to 13 membered heteroaryl, alkanoyl, or imide, wherein, if present, the substituent is at least one $C_1$–$C_4$ alkyl, cyano, fluoride, chloride, bromide, hydroxy, nitro, or thiol;

more preferably, $R_1$ and $R_2$ are each independently straight chain or branched substituted or unsubstituted $C_1$–$C_8$ alkyl or unsaturated alkyl, $C_1$–$C_4$ alkoxy, substituted or unsubstituted $C_2$–$C_6$ alkylamino, substituted or unsubstituted 3 to 6 membered cycloalkyl, substituted or unsubstituted 4 to 5 membered heterocycloalkyl having at least one oxygen, nitrogen, or sulfur atom within the ring, substituted or unsubstituted 5 to 16 membered aryl, substituted or unsubstituted 5 to 10 membered arylalkyl, substituted or unsubstituted 4 to 6 membered heteroaryl having at least one oxygen, nitrogen, or sulfur atom in the ring, $C_1$–$C_4$ alkanoyl, or imide, wherein, if present, the substituent is at least one $C_1$–$C_4$ alkyl, cyano, fluoride, chloride, bromide, hydroxy, nitro, or thiol; and most preferably, $R_1$ and $R_2$ are each independently hydrogen, methyl, ethyl, propyl, isopropyl, sec-butyl, 3-methylbutyl, 2-methyl-2-propenyl, 2-propynyl, pentyl, hexyl, 2-butylyl, 2-hydroxy-2-(4-hydroxyphenyl)ethyl, 2-(2-pyridinyl) ethyl, 2-hydroxy-2-(3,4-dihydroxyphenyl)ethyl, 3-pyridinylmethyl, 2,5-difluorobenzyl, 4-trifluoromethoxyphenylmethyl, 3-methoxypropyl, 2-hydroxyethyl, 4-phenylbutyl, 2-phosphonatethyl, 3-(2-methyl)ethoxypropyl, 2-(2-thiophenyl)ethyl, N-benzyl-4-piperidinyl, 3-(1-pyrrolidinyl)propyl, 2-(N,N-diethyl)ethyl, tetrahydrofuranylmethyl, cyclopentyl, or cyclohexyl.

$R_4$, $R_{4'}$, $R_5$, $R_{5'}$, $R_8$, $R_{8'}$, $R_9$, and $R_{9'}$ are each independently hydrogen, halide, saturated or unsaturated straight or branched substituted or unsubstituted alkyl, hydroxy, substituted or unsubstituted alkoxy, substituted or unsubstituted cycloalkyl, substituted or unsubstituted aryl, substituted or unsubstituted arylalkyl, substituted or unsubstituted heterocycloalkyl, substituted or unsubstituted heterocycloaryl or substituted or unsubstituted heteroaryl; wherein, if present, the substituent is at least one alkanoyl, imide, alkyl, hydroxy, halide, methoxy, ethoxy, carboxylic acid, cyano, amine, alkylamine, amide, carboxylic acid, ester, nitro, sulfide, sulfonyl, sulfonamide, acetal, acetylene, aminal, amino acid, amino acid ester, azo, diazo, azide, carbamate, carboxylic acid ester, carboalkoxy ester, cyanohydrin, diazonium salt, glucoside, glucuronide, halocarbon, polyhalocarbon, halocarbonoxy, polyhalocarbonoxy, hydroxylamine, ketone, lactone, nitrile, nitrile oxide, N-oxides, nucleoside linked, oxime, phosphate, phosphinate, phosphonate, phosphonic acid, quaternary ammonium salt, sulfoxide, sulfone, sulfonate ester, sulfinate ester, sulfonic acid, thioacetal, thiocarboxylic acid, thiol, or thioaryl; and preferably, $R_5$, $R_{5'}$, $R_9$, and $R_{9'}$ are each independently hydrogen, $C_1$–$C_4$ alkyl, $C_1$–$C_4$ alkoxy, amine, $C_1$–$C_4$ alkylamine, $C_1$–$C_4$ amide, carboxylic acid, ester, halide, hydroxy, nitro, $C_1$–$C_4$ sulfide, $C_1$–$C_4$ sulfonyl, or sulfonamide;

more preferably, $R_5$ and $R_9$ are each independently are hydrogen $C_1$–$C_2$ alkyl, $C_1$–$C_2$ alkoxy, amine, $C_1$–$C_2$ alkylamine, fluoride, chloride, bromide, hydroxy, nitro, $C_1$–$C_2$ sulfide, or $C_1$–$C_2$ sulfonyl;

more preferably, $R_{5'}$ and $R_{9'}$ are each independently, hydrogen, $C_1$–$C_2$ alkyl, $C_1$–$C_2$ alkoxy, amine, $C_1$–$C_2$ alkylamine, $C_1$–$C_2$ amide, carboxylic acid, $C_2$–$C_4$ ester, or sulfonamide;

most preferably, $R_5$ and $R_9$ are each independently are hydrogen, methyl, methoxy, thiomethyl, fluorine, chlorine, nitro, or methylsulfonyl; and most preferably, $R_{5'}$ and $R_{9'}$ are each independently, hydrogen, methyl, methyl ester, ethyl ester, $C_1$–$C_2$ amide, carboxylic acid, methoxy, or sulfonamide.

$R_6$ is hydrogen, saturated or unsaturated,saturated or unsaturated straight or branched substituted or unsubstituted alkyl, substituted or unsubstituted alkoxy, substituted or unsubstituted alkylamino, substituted or unsubstituted cycloalkyl, substituted or unsubstituted heterocycloalkyl, substituted or unsubstituted aryl, substituted or unsubstituted arylalkyl, substituted or unsubstituted heterocycloaryl or substituted or unsubstituted heteroaryl; wherein, if present, the substituent is at least one alkanoyl, imide, alkyl, hydroxy, halide, methoxy, ethoxy, carboxylic acid, cyano, nitro, thiol, alkanoyl, imide, acetal, acetylene, aminal, amino acid, azo, diazo, carbamate, carboalkoxy ester, cyanohydrin, glucoside, glucuronide, halocarbon, polyhalocarbon, halocarbonoxy, polyhalocarbonoxy, ketone, nitrile, nitrile oxide, N-oxides, nucleoside linked, oxime, sulfone, or sulfonic acid.

preferably, $R_6$ is hydrogen, a $C_1$–$C_8$ straight chain or branched alkyl or substituted alkyl or unsaturated alkyl, substituted or unsubstituted 3 to 8 membered cycloalkyl, substituted or unsubstituted 5 to 16 membered aryl, substituted or unsubstituted 5 to 10 membered arylalkyl, 4 to 12 membered heterocycloalkyl or heteroaryl with at least one oxygen, sulfur, or nitrogen atom within the ring, wherein, if present, the substituent is at least one hydroxy, halide, methoxy, ethoxy, carboxylic acid, ester, amine, or alkylamine;

more preferably, $R_6$ is hydrogen, a $C_1$–$C_4$ straight chain or branched alkyl or unsaturated alkyl, substituted or unsubstituted 3 to 6 membered cycloalkyl, substituted or unsubstituted 5 to 6 membered aryl, substituted or unsubstituted 5 to 8 membered arylalkyl, or 4 to 9 membered heterocycloalkyl or heteroaryl with at least one oxygen, sulfur, or nitrogen atom within the ring, wherein, if present, the substituent is at least one hydroxy, fluoride, chloride, bromide, methoxy, ethoxy, carboxylic acid, ester, amine, or $C_1$–$C_4$ alkylamine; and most preferably, $R_6$ is hydrogen, a benzyl, cyclopentyl, cyclohexyl, isopropyl, propyl, butyl, methylene cyclopropyl, methylene cyclobutyl, or benzimidazolyl.

In a preferred compound of Formula III, $R_{4'}$, $R_{5'}$, $R_{8'}$, $R_{9'}$ and $R_6$ are hydrogen. In another embodiment of the compounds of Formula III, at least one of $R_4$, $R_{4'}$, $R_8$, and $R_{8'}$ is not hydrogen. In another embodiment of the compounds of Formula III, at least two of $R_4$, $R_{4'}$, $R_8$, and $R_{8'}$ are not hydrogen. In another embodiment of the compounds of Formula III, at least three of $R_4$, $R_{4'}$, $R_8$, and $R_{8'}$ are not hydrogen. In another embodiment of the compounds of Formula III, at least one of $R_5$, $R_{5'}$, $R_9$, and $R_{9'}$ is not hydrogen. In another embodiment of the compounds of Formula III, at least two of $R_5$, $R_{5'}$, $R_9$, and $R_{9'}$ are not hydrogen. In another embodiment of the compounds of Formula III, at least three of $R_5$, $R_{5'}$, $R_9$, and $R_{9'}$ are not hydrogen.

The compounds of the invention encompassed by Formula III include compounds of Formula XII as described in the formula of the header of Table 6, additional non-limiting specific compounds are contained within the table. The specific compounds are for illustration and not limitation. In each compound in Table 6, $R_6$ is hydrogen. Each compound in Table 6 has been prepared, isolated, purified, and tested for antiviral activity and cytotoxicity as discussed below.

TABLE 6

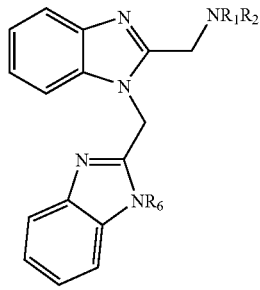

Formula XII

| Cmpd. # | $R_1$ | $R_2$ | PRA ($IC_{50}$) μg/mL | XTT ($CC_{50}$) μg/mL | Selective Index |
|---|---|---|---|---|---|
| 80 | (piperidin-4-yl, N-methyl) | —$CH_3$ | 8 | 58 | 7.3 |
| 81 | Isopropyl | —$CH_2CH_3$ | 0.14 | 63 | 450 |
| 82 | Isopropyl | —$CH_3$ | 0.02 | 25 | 1388.9 |
| 83 | (allyl) | —$CH_3$ | 0.19 | 58 | 305.3 |
| 84 | (2-(dimethylamino)ethyl) | —$CH_3$ | 1.8 | 100 | 55.6 |
| 85 | (furfuryl) | —$CH_3$ | 0.46 | 100 | 217.4 |

TABLE 6-continued
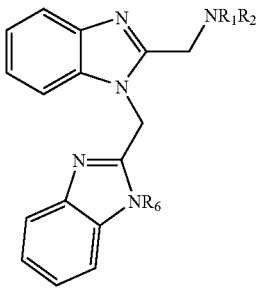
Formula XII
| Cmpd. # | R$_1$ | R$_2$ | PRA (IC$_{50}$) μg/mL | XTT (CC$_{50}$) μg/mL | Selective Index |
|---|---|---|---|---|---|
| 86 | (1-phenylethyl) | —CH$_3$ | 0.41 | 62 | 151.2 |
| 87 | (isobutyl-like) | (isobutyl-like) | 0.15 | 100 | 666.7 |
| 88 | n-hexyl- | —CH$_3$ | 0.15 | 100 | 666.7 |
| 89* | (2-methylallyl) | —CH$_2$CH$_3$ | 0.07 | 100 | 1470.6 |
| 90 | (propargyl) | —CH$_3$ | 0.31 | 100 | 322.6 |
| 91 | n-pentyl- | —CH$_3$ | 0.17 | 80 | 470.6 |
| 92 | n-butyl- | —CH$_2$CH$_3$ | 0.1 | 68 | 715.8 |
| 93 | (benzyl) | (dimethylaminoethyl) | 0.54 | 100 | 185.2 |
| 94 | (3-butynyl) | —CH$_3$ | 1.3 | 16 | 12.3 |
| 95 | (CH$_2$C(O)OCH$_3$) | —CH$_3$ | 7.8 | 100 | 12.8 |
| 96 | HO—CH$_2$CH$_2$— | —CH$_2$CH$_3$ | 0.53 | 100 | 188.7 |
| 97 | (4-hydroxyphenyl-CH(OH)-CH$_2$-) | —CH$_3$ | 0.13 | 77 | 592.3 |

TABLE 6-continued
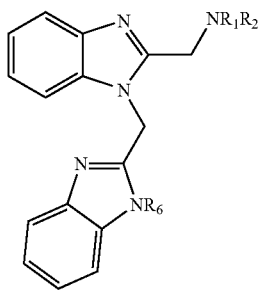
Formula XII
| Cmpd. # | R₁ | R₂ | PRA (IC$_{50}$) μg/mL | XTT (CC$_{50}$) μg/mL | Selective Index |
|---|---|---|---|---|---|
| 98 | 2-pyridylethyl | —CH₃ | 0.3 | 100 | 333.3 |
| 99 | 4-pyridylmethyl | —CH₂CH₃ | 6.9 | 100 | 14.5 |
| 100 | di-n-butylamino-ethyl | H | 8 | 9.3 | 1.2 |
| 101 | dimethylaminopropyl | dimethylaminopropyl | 8 | 100 | 125 |
| 102 | 3-pyridylmethyl | cyanopropyl | 8 | 100 | 12.5 |
| 103 | cyanomethyl | H | 8 | 100 | 12.5 |
| 104 | amidino | H | 8 | 100 | 12.5 |
| 105 | imidazolylpropyl | H | 1.6 | 26 | 16.3 |
| 106 | n-octyl | n-octyl | 8 | 74 | 9.3 |

TABLE 6-continued
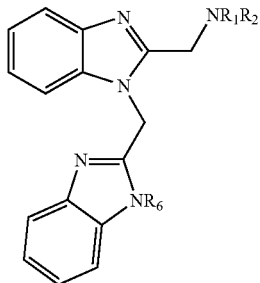
Formula XII
| Cmpd. # | R$_1$ | R$_2$ | PRA (IC$_{50}$) μg/mL | XTT (CC$_{50}$) μg/mL | Selective Index |
|---|---|---|---|---|---|
| 107 | HO, OH, OH (catechol with CH(OH)) | isopropyl | 0.05 | 100 | 1886.8 |
| 108 | naphthyl-CH(CH$_3$)- | —CH$_3$ | 0.35 | 28 | 80 |
| 109 | naphthyl-CH(CH$_3$)- | —CH$_3$ | 2.3 | 100 | 43.5 |
| 110 | 4-methoxyphenyl | —CH$_3$ | 1.6 | 100 | 62.5 |
| 111 | diphenylmethyl | —CH$_3$ | 8 | 100 | 12.5 |
| 112 | 4-methylpiperazinyl-propyl | H | 0.7 | 100 | 143 |
| 113 | pyridin-3-yl-ethyl | H | 0.17 | 100 | 588 |

TABLE 6-continued
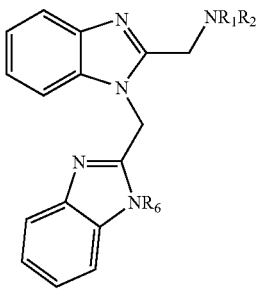
Formula XII
| Cmpd. # | R₁ | R₂ | PRA (IC$_{50}$) μg/mL | XTT (CC$_{50}$) μg/mL | Selective Index |
|---|---|---|---|---|---|
| 114 | 2,5-difluorobenzyl | H | 0.15 | 100 | 667 |
| 115 | 4-(trifluoromethoxy)benzyl | H | 0.2 | 100 | 500 |
| 116 | CH$_3$—O—CH$_2$ CH$_2$CH$_2$— | H | 0.135 | 100 | 741 |
| 117** | HO—CH$_2$CH$_2$— | H | 0.13 | 100 | 769 |
| 118 | 4-phenylbutyl | H | 0.16 | 95 | 594 |
| 119 | norbornyl | H | 0.11 | 100 | 909 |
| 120 | 4-methoxyphenethyl | H | 0.62 | 100 | 161 |
| 121 | CH(CH$_3$)P(O)(OH)$_2$ | H | 0.16 | 100 | 625 |
| 122 | 3,5-dimethoxybenzyl | H | 0.9 | 100 | 111 |
| 123 | —CH$_2$CH$_3$ | H | 0.26 | 100 | 3846 |

TABLE 6-continued
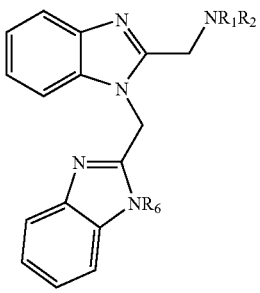
Formula XII
| Cmpd. # | R₁ | R₂ | PRA (IC$_{50}$) μg/mL | XTT (CC$_{50}$) μg/mL | Selective Index |
|---|---|---|---|---|---|
| 124 | morpholinopropyl | H | 0.4 | 100 | 250 |
| 125 | 2-(pyridin-2-yl)ethyl | H | 0.31. | 100 | 323 |
| 126 | 4-fluorobenzyl | H | 3.8 | 100 | 26 |
| 127*** | 3-(trifluoromethoxy)benzyl | H | 1.9 | 100 | 53 |
| 128 | —CH₂CH₂CH₃ | H | 0.12 | 100 | 833 |
| 129 | 2-isopropoxyethyl (propyl chain) | H | 0.18 | 100 | 556 |
| 130 | 2-(thiophen-2-yl)ethyl | H | 0.21 | 100 | 476 |
| 131 | 2-phenylpropyl | H | 0.36 | 100 | 278 |
| 132 | 3,3-diphenylpropyl | H | 0.86 | 100 | 116 |

TABLE 6-continued
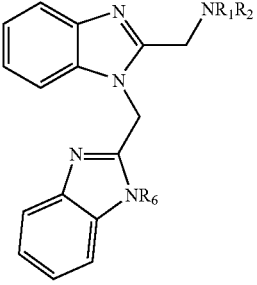
Formula XII
| Cmpd. # | $R_1$ | $R_2$ | PRA ($IC_{50}$) μg/mL | XTT ($CC_{50}$) μg/mL | Selective Index |
|---|---|---|---|---|---|
| 133 | 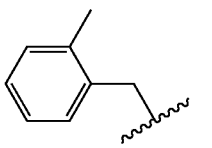 | H | 0.7 | 100 | 143 |
| 134 | 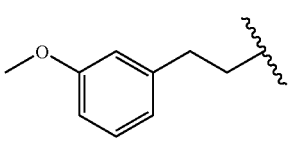 | H | 0.41 | 100 | 244 |
| 135 | 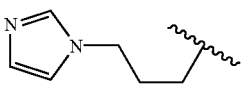 | H | 0.41 | 100 | 244 |
| 136 | 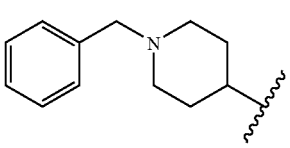 | H | 0.76 | 100 | 132 |
| 137 | 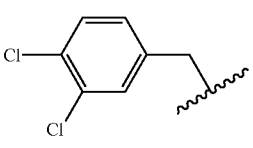 | H | 0.26 | 95 | 365 |
| 138 | 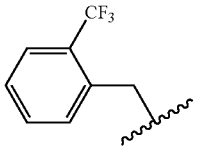 | H | 0.9 | 6.5 | 7 |
| 139 | 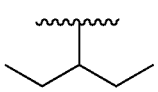 | H | 0.79 | 18 | 23 |
| 140 | | H | 0.76 | 100 | 132 |

TABLE 6-continued
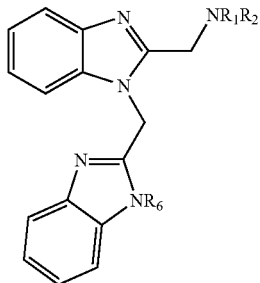
Formula XII
| Cmpd. # | R$_1$ | R$_2$ | PRA (IC$_{50}$) µg/mL | XTT (CC$_{50}$) µg/mL | Selective Index |
|---|---|---|---|---|---|
| 141 | pyrrolidinone-butyl | H | 0.6 | 35 | 58 |
| 142 | thiophene-methyl | H | 1.6 | 100 | 63 |
| 143 | phenyl-CH$_2$CH$_2$CH(CH$_3$)- | H | 0.45 | 41 | 91 |
| 144 | indanyl | H | 1.8 | 100 | 56 |
| 145 | benzyl | H | 1.98 | 100 | 51 |
| 146 | 4-methoxybenzyl | H | 2.2 | 100 | 45 |
| 147 | pyrrolidinyl-butyl | H | 0.29 | 100 | 345 |
| 148 | Et$_2$N-CH$_2$CH$_2$CH$_2$CH(CH$_3$)- | H | 1.24 | 100 | 81 |
| 149 | 1-benzyl-pyrrolidin-3-yl | H | 0.93 | 39 | 42 |

TABLE 6-continued
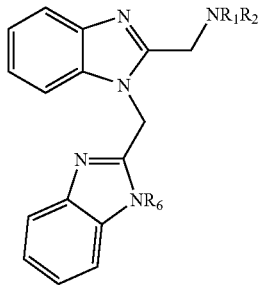
Formula XII
| Cmpd. # | R₁ | R₂ | PRA (IC$_{50}$) μg/mL | XTT (CC$_{50}$) μg/mL | Selective Index |
|---|---|---|---|---|---|
| 150 | 2-chlorobenzyl | H | 1.3 | 100 | 77 |
| 151 | 4-(trifluoromethyl)benzyl | H | 8 | 100 | 13 |
| 152 | isopropyl | H | 0.047 | 100 | 2128 |
| 153 | cyclohexylmethyl | H | 0.645 | 100 | 155 |
| 154 | furfuryl | H | 2 | 100 | 50 |
| 155 | phenethyl | H | 0.46 | 100 | 217 |
| 156 | 1,2,3,4-tetrahydronaphthyl | H | 0.85 | 100 | 118 |
| 157 | 3-chlorobenzyl | H | 0.58 | 100 | 172 |
| 158 | 4-(2-oxopyrrolidin-1-yl)butyl | H | 0.34 | 100 | 294 |
| 159 | CH₃CH₂—O—CH₂CH₂CH₂— | H | 0.49 | 100 | 204 |

TABLE 6-continued
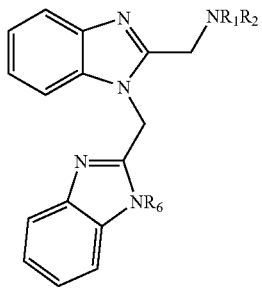
Formula XII
| Cmpd. # | R₁ | R₂ | PRA (IC$_{50}$) μg/mL | XTT (CC$_{50}$) μg/mL | Selective Index |
|---|---|---|---|---|---|
| 160 | 2-methylpiperidinyl-propyl | H | 1.9 | 88 | 46 |
| 161 | 2,6-difluorobenzyl | H | 0.58 | 100 | 172 |
| 162 | N,N-diethylaminopropyl | H | 0.3 | 100 | 333 |
| 163 | 4-chlorophenethyl | H | 0.45 | 16 | 36 |
| 164 | CH₃— | H | 0.8 | 100 | 125 |
| 165 | cyclohexyl | H | 1.75 | 100 | 57 |
| 166 | (2-oxoimidazolidin-1-yl)propyl | H | 0.65 | 100 | 154 |
| 167 | 4-fluorophenethyl | H | 0.39 | 100 | 256 |
| 168 | 1,2-diphenylethyl | H | 4.9 | 100 | 20 |

TABLE 6-continued
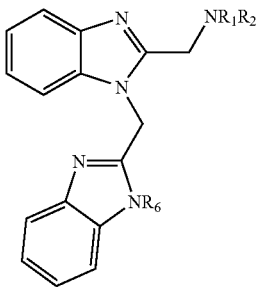
Formula XII
| Cmpd. # | R$_1$ | R$_2$ | PRA (IC$_{50}$) μg/mL | XTT (CC$_{50}$) μg/mL | Selective Index |
|---|---|---|---|---|---|
| 169 | benzodioxole-CH$_2$- | H | 1.32 | 100 | 76 |
| 170 | tetrahydrofuran-2-yl-CH$_2$- | H | 0.17 | 100 | 588 |
| 171 | 3,4-dichlorobenzyl | H | 0.93 | 58 | 62 |
| 172 | (1-methylpyrrolidin-2-yl)ethyl | H | 0.7 | 95 | 136 |
| 173 | 3,5-difluorobenzyl | H | 0.799 | 6.4 | 8 |
| 174 | 3-(dimethylamino)propyl | H | 1.5 | 100 | 67 |
| 175 | 2-methoxyphenethyl | H | 0.36 | 100 | 278 |
| 176 | 2-(hydroxymethyl)hexyl | H | 0.51 | 100 | 196 |
| 177 | cyclopentyl | H | 0.03 | 100 | 3333 |

TABLE 6-continued
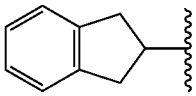
Formula XII
| Cmpd. # | R₁ | R₂ | PRA (IC$_{50}$) µg/mL | XTT (CC$_{50}$) µg/mL | Selective Index |
|---|---|---|---|---|---|
| 178 | 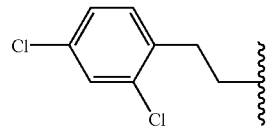 | H | 0.23 | 16 | 70 |
| 179 | 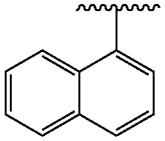 | H | 1 | 45 | 45 |
| 180 | 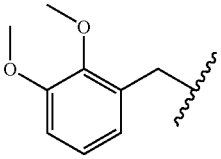 | H | 0.395 | 14 | 35 |
| 181 | 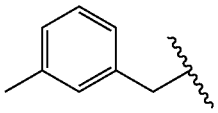 | H | 0.7 | 100 | 143 |
| 182 | CH₃CH₂—O—CH₂CH₂CH₂— | H | 0.27 | 100 | 370 |
| 183 |  | H | 0.32 | 100 | 313 |
*¹H NMR (d₆-DMSO) δ ppm: 7.78 (d, 2H); 7.58 (m, 2H); 7.35 (m, 2H); 7.21 (m, 2H); 5.9 (s, 2H); 4.28 (s, 2H); 3.95 (s, 2H); 3.25 (q, 2H); 1.8 (s, 3H); 1.3 (t, 3H).
**¹H NMR(d₆-DMSO) δ ppm: 7.75 (m, 2H); 7.61 (m, 2H); 7.3 (m, 4H); 5.98 (s, 2H); 4.8 (s, 2H); 3.79 (t, 2H); 3.25 (t, 2H).
***¹H NMR(d₆-DMSO) δ ppm: 7.75 (d, 2H); 7.61 (s, 1H); 7.6 (d, 2H); 7.45 (m, 1H); 7.38 (m, 2H); 7.3 (m, 2H); 7.19 (m, 2H); 5.85 (s, 2H); 4.82 (s, 2H); 4.5 (s, 2H).

In another preferred embodiment of the invention, with reference to Formula III, $R_1$ and $R_2$ are taken together to form a saturated or unsaturated nitrogen containing ring, the 1-position of the benzimidazole moiety is substituted with a substituted or unsubstituted methylene-benzimidazole moiety, thus, the present invention encompasses compounds of the general Formula IV:

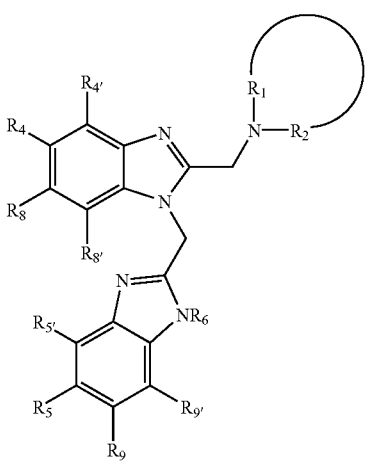

Formula IV or a pharmaceutically-acceptable prodrug, salt, solvate including hydrate, clathrate, enantiomer, diastereomer, racemate, or mixture of stereoisomers thereof, wherein:

—$R_1$—N—$R_2$— form a saturated or unsaturated substituted or unsubstituted heterocycloalkyl ring, substituted or unsubstituted heteroaryl ring, wherein, if present, the substituent is at least one substituted or unsubstituted lower alkyl, substituted or unsubstituted lower alkoxy, amides, sulfonamides, esters, hydroxy, halide, substituted or unsubstituted aryl, substituted or unsubstituted cycloalkyl, substituted or unsubstituted heterocycloalkyl, substituted or unsubstituted heterocycloaryl or substituted or unsubstituted heteroaryl; wherein, if present, the substituent is at least one alkanoyl, imide, alkyl, hydroxy. halide, methoxy, ethoxy, carboxylic acid, cyano, carbonyl, nitro, acetal, acetylene, aminal, amino acid, amino acid ester, azo, diazo, azide, carbamate, carboxylic acid ester, carboalkoxy ester, cyanohydrin, diazonium salt, glucoside, glucuronide, halocarbon, polyhalocarbon, halocarbonoxy, polyhalocarbonoxy, hydroxylamine, ketone, lactone, nitrile, nitrile oxide, N-oxides, nucleoside linked, oxime, phosphate, phosphinate, phosphonate, phosphonic acid, quaternary ammonium salt, sulfoxide, sulfone, sulfonate ester, sulfinate ester, sulfonic acid, thioacetal, thiocarboxylic acid, thiol, or thioaryl;

preferably, —$R_1$—N—$R_2$— form a saturated or unsaturated, substituted or unsubstituted 3 to 7 membered cycloalkyl, substituted or unsubstituted 3 to 7 membered heterocycloalkyl, substituted or unsubstituted 3 to 7 membered heteroaryl, wherein, if present, the substituent is at least one substituted or unsubstituted $C_1$–$C_4$ alkyl, substituted or unsubstituted $C_1$–$C_4$ alkoxy, $C_1$–$C_4$ esters, hydroxy, fluoride, chloride, bromide, substituted or unsubstituted 3 to 8 membered aryl, substituted or unsubstituted 4 to 6 membered cycloalkyl, substituted or unsubstituted 3 to 8 membered heterocycloalkyl, carbonyl, or nitro;

more preferably, —$R_1$—N—$R_2$— form a 5, 6, or 8 membered having at least one nitrogen atom, such as pyrrolidinyl, piperidinyl, optionally having a second atom which is nitrogen, oxygen, or sulfur atom, or at least one unsaturation, such as pyrrolyl, imidazolyl, pyridinyl, pyrimidinyl, piperazinyl, quinolinyl, acridinyl, thiazole, morpholinyl, and substituted with at least one methyl, ethyl, ester, methanol, 2-ethanol, aldehyde, substituted or unsubstituted aryl; and most preferably, —$R_1$—N—$R_2$— form a cyclic structure such as 2,5-dihydropyrrolyl, 3,5-dimethylpyrrolidinyl, 2-hydroxymethylpyrrolidinyl, 2-(2-hydroxyethyl)piperidinyl, N-carbaldehydepiperazinyl, N-(3-trifluoromethylphenyl)piperazinyl, N-(4-hydroxyphenyl)piperazinyl, N-(benzylcarbate)piperazinyl, tetrahydrothiazolyl, N-(4-acetylphenyl)piperazinyl, and cyclooctazanyl.

$R_4$, $R_{4'}$, $R_5$, $R_{5'}$, $R_6$, $R_8$, $R_{8'}$, $R_9$, and $R_{9'}$ are as defined above for Formula III.

In another embodiment of the compounds of Formula IV, $R_{4'}$, $R_{5'}$, $R_{8'}$, and $R_{9'}$ are hydrogen. In another embodiment of the compounds of Formula IV, at least two of $R_4$, $R_{4'}$, $R_8$, and $R_{8'}$ are not hydrogen. In another embodiment of the compounds of Formula IV, at least one of $R_4$, $R_{4'}$, $R_8$, and $R_{8'}$ is not hydrogen. In another embodiment of the compounds of Formula IV, at least three of $R_4$, $R_{4'}$, $R_8$, and $R_{8'}$ are not hydrogen. In another embodiment of the compounds of Formula IV, $R_5$, $R_{5'}$, $R_9$, and $R_{9'}$ are hydrogen. In another embodiment of the compounds of Formula IV, at least one of $R_5$, $R_{5'}$, $R_9$, and $R_{9'}$ is not hydrogen. In another embodiment of the compounds of Formula IV, at least two of $R_5$, $R_{5'}$, $R_9$, and $R_{9'}$ are not hydrogen. In another embodiment of the compounds of Formula IV, at least three of $R_5$, $R_{5'}$, $R_9$, and $R_{9'}$ are not hydrogen. In another embodiment of the compounds of Formula IV, $R_6$ is hydrogen.

The compounds of the invention encompassed by Formula IV include compounds of formulas XIII and XIV described in the formula of the header of Tables 7 and 8, additional non-limiting specific compounds are contained within the table. The specific compounds are for illustration and not limitation. Each compound in Tables 7 and 8 has been prepared, isolated, purified, and tested for antiviral activity and cytotoxicity as discussed below. For illustration purposes only, in Table 7, $R_1$ and $R_2$ represent bonds, for example, $R_1$—$CH_2CH_2CH_2$—$R_2$ represents a 4 membered including one nitrogen atom. In Table 8, $R_1$ and $R_2$ are taken together to form a morpholine ring.

TABLE 7
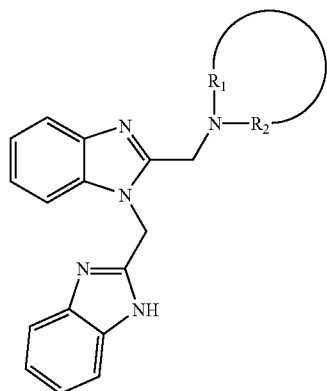
Formula XIII
| Cmpd. # | R₁ and R₂ | PRA (IC$_{50}$) µg/mL | XTT (CC$_{50}$) µg/mL | Selective Index |
|---|---|---|---|---|
| 195[a] | R₁, R₂ (morpholine-like ring with O) | 0.01 | 100 | 10000 |
| 196[b] | R₁, R₂ with N-pyridyl-CF₃ | 0.01 | 78 | 7600 |
| 197[c] | R₁, R₂ with N-phenyl-OCH₃ | 0.03 | 100 | 3000 |
| 198[d] | R₁, R₂ with N-C(O)-furyl | 0.03 | 100 | 3300 |
| 199[e] | R₁—CH₂CH₂CH₂CH₂—R₂ | 0.01 | 100 | 1000 |
| 200 | R₁—CH₂CH₂CH₂—R₂ | 0.14 | 7.6 | 54.3 |
| 201[f] | R₁—CH₂CH=CHCH₂—R₂ | 0.07 | 19 | 292.3 |
| 202 | R₁—CH₂CH₂CH=CHCH₂—R₂ | 0.8 | 100 | 125 |
| 203 | (cycloheptane with ethyl ester) | 0.57 | 100 | 175.4 |
| 204 | (benzyl imine structure) | 1.7 | 100 | 58.8 |

TABLE 7-continued
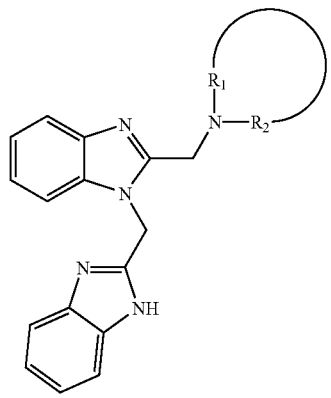
Formula XIII
| Cmpd. # | R₁ and R₂ | PRA (IC$_{50}$) µg/mL | XTT (CC$_{50}$) µg/mL | Selective Index |
|---|---|---|---|---|
| 205 | | 0.1 | 100 | 1000 |
| 206 | | 2.8 | 100 | 35.7 |
| 207 | | 0.19 | 100 | 526.3 |
| 208 | | 0.12 | 100 | 833.3 |
| 209 | | 0.01 | 100 | 10000 |
| 210 | | 0.25 | 8 | 32 |
| 211 | | 0.21 | 32 | 152.4 |

TABLE 7-continued
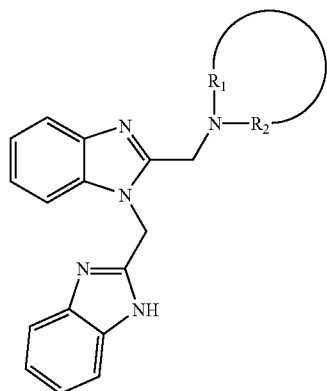
Formula XIII
| Cmpd. # | R₁ and R₂ | PRA (IC$_{50}$) μg/mL | XTT (CC$_{50}$) μg/mL | Selective Index |
|---|---|---|---|---|
| 213 | R₁, R₂—(CH chain)—OH | 0.02 | 100 | 5882.4 |
| 214 | R₁, R₂ on cyclohexane | 8 | 100 | 12.5 |
| 215 | R₁, R₂—N(azepane)—pyridine(CF₃)(Cl) | 1.5 | 100 | 66.7 |
| 216 | R₁, R₂—N—CH₂CH₂—O—CH₂CH₂—OH | 1.9 | 9 | 47 |
| 217 | R₁, R₂—(piperidine)—piperidine-N | 7.1 | 100 | 14.1 |
| 218 | R₁, R₂—N—CHO | 0.1 | 100 | 1000 |
| 219 | R₁, R₂—N—phenyl-CF₃ | 0.13 | 100 | 769.2 |
| 220 | R₁, R₂—N—phenyl-OH | 0.15 | 100 | 666.7 |

TABLE 7-continued
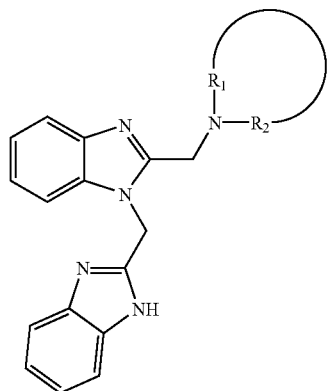
Formula XIII
| Cmpd. # | R₁ and R₂ | PRA (IC$_{50}$) µg/mL | XTT (CC$_{50}$) µg/mL | Selective Index |
|---|---|---|---|---|
| 221 | R₁–⌒–N(C(=O)O–CH₂–Ph)–⌒–R₂ | 0.02 | 100 | 4347.8 |
| 222 | R₁–CH₂CH₂–S–CH₂–R₂ | 0.15 | 100 | 666.7 |
| 223 | (3,4-dimethoxyphenyl with CH₂CN and CH₂CH₂, R₁ R₂) | 4.1 | 100 | 24.4 |
| 224 | R₁–C(=O)–(CH₂)₃–C(=O)–R₂ | 8 | 100 | 12.5 |
| 225 | R₁–C(=O)–(CH₂)₂–C(=O)–R₂ | 8 | 100 | 12.5 |
| 226 | R₁–C(=O)–(o-C₆H₄)–C(=O)–R₂ | 8 | 50 | 6.3 |

TABLE 7-continued
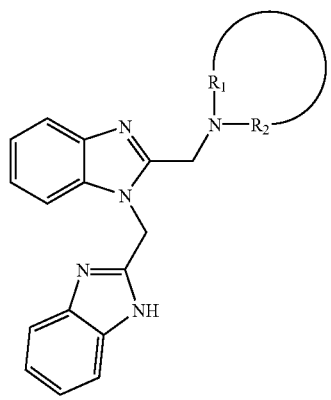
Formula XIII
| Cmpd. # | $R_1$ and $R_2$ | PRA (IC$_{50}$) µg/mL | XTT (CC$_{50}$) µg/mL | Selective Index |
|---|---|---|---|---|
| 227 | | 7.8 | 100 | 12.8 |
| 228 | | 1.3 | 60 | 46.2 |
| 229 | | 0.36 | 100 | 277.8 |
| 230 | | 4.8 | 100 | 20.8 |
| 231 | | 2.1 | 15 | 7.1 |
| 232 | | 0.81 | 100 | 123.5 |
| 233 | | 0.02 | 100 | 6250 |

TABLE 7-continued
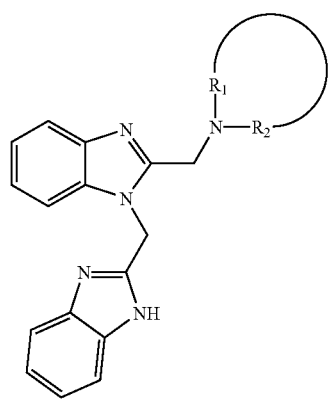
Formula XIII
| Cmpd. # | R$_1$ and R$_2$ | PRA (IC$_{50}$) μg/mL | XTT (CC$_{50}$) μg/mL | Selective Index |
|---|---|---|---|---|
| 234 | cyclohexane with R$_1$-CH$_2$ and R$_2$-CH$_2$CH$_2$ substituents | 0.4 | 24 | 60 |
| 235 | 5-Br phenyl with R$_1$ ortho and R$_2$-C(O)C(O)- | 5.4 | 100 | 18.5 |
| 236 | 5-NO$_2$ phenyl with R$_1$ ortho and R$_2$-C(O)C(O)- | 8 | 100 | 12.5 |
| 237 | 5-F phenyl with R$_1$ ortho and R$_2$-C(O)C(O)- | 5.7 | 65 | 11.4 |

TABLE 7-continued

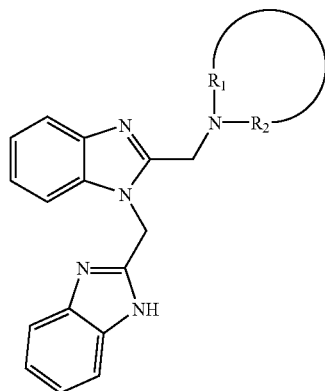

Formula XIII

| Cmpd. # | $R_1$ and $R_2$ | PRA (IC$_{50}$) μg/mL | XTT (CC$_{50}$) μg/mL | Selective Index |
|---|---|---|---|---|
| 238 | (2-R$_1$, 5-I, R$_2$-C(O)C(O)- substituted phenyl) | 5.2 | 25 | 4.8 |

[a] $^1$H NMR (d$_6$-DMSO) δ ppm: 7.6 (d, 1H); 7.52 (m, 2H); 7.43 (m, 1H); 7.2 (m, 2H); 7.15 (m, 2H); 5.9 (s, 2H); 3.9 (s, 2H); 3.3 (br s, 4H); 2.1 (br s, 4H). MS (M$^+$): 348.198. HPLC Purity 98.5%.
[b] $^1$H NMR (d$_6$-DMSO) δ ppm: 8.5 (s, 1H); 7.95 (dd, 1H); 7.78 (t, 2H); 7.6 (m, 2H); 7.35 (q, 2H); 7.25 (m, 2H); 7.05 (d, 1H); 6.0 (s, 2H); 4.8 (s, 2H); 3.85 (br s, 4H); 3.4 (br s, 4H).
[c] $^1$H NMR (d$_6$-DMSO) δ ppm: 7.75 (t, 2H); 7.59 (m, 2H); 7.35 (q, 2H); 7.2 (m, 2H); 6.95 (d, 2H); 6.85 (d, 2H); 5.9 (s, 2H); 4.9 (s, 2H); 3.5 (br s, 4H); 3.2 (br s, 4H).
[d] $^1$H NMR (d$_6$-DMSO) δ ppm: 7.90 (d, 1H); 7.75 (m, 2H); 7.6 (m, 2H); 7.38 (q, 2H); 7.25 (m, 2H); 7.05 (d, 1H); 6.6 (d, 1H); 5.98 (s, 2H); 4.62 (s, 2H); 3.8 (br s, 4H); 3.2 (br s, 4H).
[e] $^1$H NMR (d$_6$-DMSO) δ ppm: 7.75 (m, 2H); 7.59 (m, 2H); 7.3 (m, 2H); 7.25 (m, 2H); 5.9 (s, 2H); 5.0 (s, 2H); 3.5 (br s, 4H); 2.0 (br s, 4H).
[f] $^1$H NMR (d$_6$-DMSO) δ ppm: 7.75 (dd, 2H); 7.5 (m, 2H); 7.3 (q, 2H); 7.2 (m, 2H); 6.02 (s, 2H); 5.85 (s, 2H); 5.1 (s, 2H); 4.3 (s 4H).

TABLE 8

Formula XIV

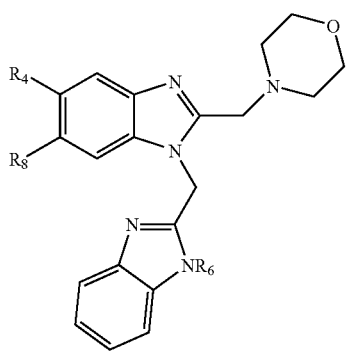

| Cmpd. # | $R_4$ | $R_8$ | PRA (IC$_{50}$) μg/mL | SI | Analytical Data |
|---|---|---|---|---|---|
| 239 | —CH$_2$OCH$_3$ | —H | 0.3 | 500 | HCl salt 300 |

TABLE 8-continued

Formula XIV

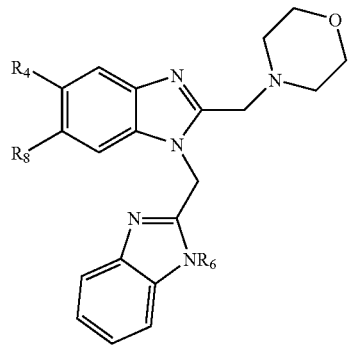

| Cmpd. # | R$_4$ | R$_8$ | PRA (IC$_{50}$) μg/mL | SI | Analytical Data |
|---|---|---|---|---|---|
| | | | | | ° C.decomp. $^1$H NMR (d$_6$-DMSO) 7.61 (s, 1H); 7.59 (d, 3H); 7.21 (m, 3H); 5.6 (s, 2H); 4.55 (s, 2H); 3.85 (br s, 4H); 3.39 (s, 3H); 2.8 (br s, 4H). MS (MH+) 341 HPLC >95% |
| 240 | —CH$_2$Cl | —H | 1.8 | 56 | MS (MH+) 468.243 HPLC >85% |
| 241 | —CH$_2$N(CH$_3$)$_2$ | —H | 4 | 26 | MS (MH+) 405 HPLC 97% |
| 242 | —CH$_2$N(isopropyl)$_2$ | —H | 8 | 13 | MS (MH+) 461 HPLC 97% |
| 243 | —CH$_2$OH | —H | 0.6 | 170 | 285° C. mp Free Base $^1$H NMR (d$_6$-DMSO) 12.5 (br s, 1H); 7.5 (s, 1H): 7.41 (d, 3H); 7.2 (d, 1H); 7.1 (br s, 2H); 5.8 (s, 2H); 4.59 (d, 2H); 3.81 (s, 2H); 3.3 (br s,. 4H); 2.4 (br s, 4H). MS (MH+) 378.196 HPLC >95% |
| 244 | —CH$_2$N(C$_8$H$_{17}$)$_2$ | —H | 2.4 | 1.4 | 69.4° C. mp TFA salt MS (MH+) 601.465 HPLC 95% |
| 245 | —CH$_2$COO(PEG1000) | —H | 8 | 13 | MS (MH+) 1476 HPLC >95% |
| 246 | —CH$_2$CN | —H | 0.3 | 330 | |
| 247 | —CONH$_2$ | —H | 2.3 | 45 | |
| 248 | —CONH(NH$_2$) | —H | 8 | 13 | |
| 249 | —COOCH3 | —H | 0.15 | 650 | 270.4° C. mp HCl salt $^1$H NMR (d$_6$-DMSO) 12.5 (br s, 1H); 8.25 (s, 1H): 7.9 (d, 1H); 7.7 (d, 1H); 7.45 (br s, 2H); 7.15 (br s, 2H); 5.95 (s, 2H); 3.9 (s, 2H); 3.85 (s, 3H); 3.2 (br s,. 4H); 2.35 (br s, 4H). MS (MH+) 406.193 HPLC >95% |
| 250 | 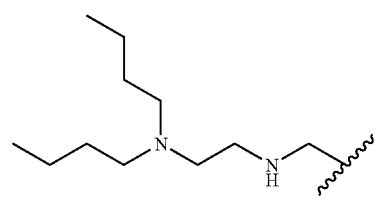 | —H | 8 | 13 | MS (MH+) 532 HPLC 97% |

TABLE 8-continued

Formula XIV

| Cmpd. # | R4 | R8 | PRA (IC50) μg/mL | SI | Analytical Data |
|---|---|---|---|---|---|
| 251 | methoxyethyl(methyl)amino- | —H | 8 | 13 | MS (MH+) 449<br>HPLC 94% |
| 252 | 1,3,4-oxadiazol-2-ylmethyl- | —H | 0.09 | 1000 | MS (MH+) 415.49<br>HPLC >95% |
| 253 | H3C-O-CH2CH2-O-CH2CH2-O-CH2CH2-O- | —H | 8 | 13 | MS (MH+) 524.307<br>HPLC >95% |
| 254 | isoindolin-2-yl- | —H | 0.1 | 600 | MS (MH+) 479<br>HPLC 97% |
| 255 | 4-(2-chlorophenyl)piperazin-1-yl- | —H | 1.6 | 47 | 167.6° C. mp TFA salt<br>MS (MH+) 556<br>HPLC 98% |
| 256 | 4-(furan-2-carbonyl)piperazin-1-yl- | —H | 1.4 | 71 | 175.1° C. mp TFA salt<br>MS (MH+) 540<br>HPLC 97% |
| 257 | 4-phenylpiperazin-1-yl- | —H | 8 | 13 | 195.5° C. mp TFA salt<br>MS (MH+) 552<br>HPLC 99% |

TABLE 8-continued

Formula XIV

| Cmpd. # | R$_4$ | R$_8$ | PRA (IC$_{50}$) μg/mL | SI | Analytical Data |
|---|---|---|---|---|---|
| 258 | N-methylpiperazinyl-CH$_2$- | —H | 8 | 13 | MS (MH+) 460.279<br>HPLC >95% |
| 259 | benzyl(methyl)amino-CH$_2$- | —H | 8 | 13 | MS (MH+) 481.258<br>HPLC >95% |
| 260 | morpholino-CH$_2$- | —H | 8 | 13 | 103.8° C. mp TFA salt<br>MS (MH+) 447.238<br>HPLC >95% |
| 261 | piperidino-CH$_2$- | —H | 8 | 13 | 59.6° C. mp TFA salt<br>MS (MH+) 445.267<br>HPLC >95% |
| 262 | 2-amino-1,3,4-thiadiazol-5-yl-CH$_2$- | —H | 0.11 | 900 | |
| 263 | 2-methylamino-1,3,4-thiadiazol-5-yl-CH$_2$- | —H | 0.19 | 550 | |
| 264 | 2-amino-1,3,4-oxadiazol-5-yl-CH$_2$- | —H | 0.4 | 250 | MS (MH+) 430.3<br>HPLC 98% |
| 265 | 2-methyl-1,3,4-oxadiazol-5-yl-CH$_2$- | —H | 0.4 | 250 | MS (MH+) 429.915<br>HPLC >98% |
| 266 | 1,3,4-oxadiazol-2-yl-CH$_2$- | —H | 0.9 | 1000 | |

TABLE 8-continued
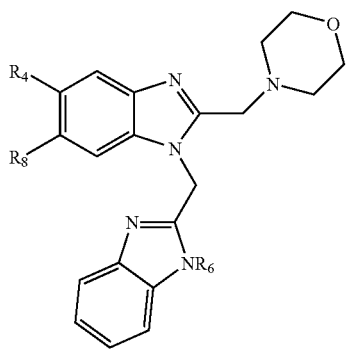
Formula XIV
| Cmpd. # | R$_4$ | R$_8$ | PRA (IC$_{50}$) μg/mL | SI | Analytical Data |
|---|---|---|---|---|---|
| 267 | H$_2$N-C(O)-CH$_2$-NH-C(O)-~ | —H | 8 | 13 | |
| 268 | HC≡C-CH$_2$-N(CH$_3$)-~ | —H | 2 | 50 | MS (MH+) 429<br>HPLC 91% |
| 269 | —H | —COOH | 3 | 30 | MS (MH+) 392.209<br>HPLC >95% |
| 270 | —H | —COOCH$_3$ | 0.01 | 10000 | 184° C. mp HCl salt<br>$^1$H NMR (d$_6$-DMSO)<br>12.5 (br s, 1H), 8.21 (s, 1H): 7.81 (d, 1H); 7.7 (d, 1H); 7.5 (d, 2H); 7.15 (m, 2H); 5.9 (s, 2H); 3.9(s, 2H); 3.85 (s, 3H); 3.2 (br s,. 4H); 2.3 (br s, 4H).<br>MS (MH+) 406.288<br>HPLC >95% |
| 271 | —H | morpholine-N-C(O)-~ | 8 | 13 | |

In another embodiment, with reference to Formula III, $R_2$ is a substituted or unsubstituted benzimidazole moiety; thus, the present invention encompasses compounds having the general Formula V:

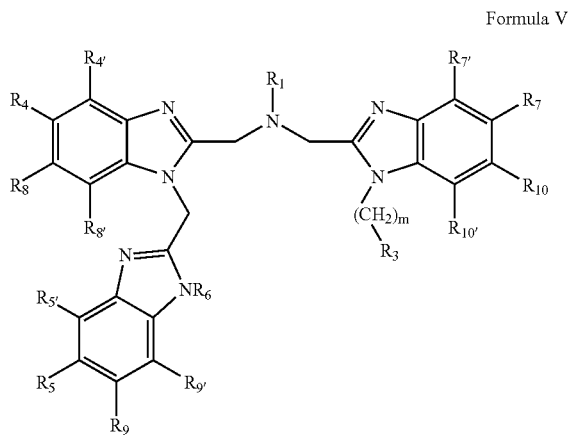

Formula V or a pharmaceutically-acceptable prodrug, salt, solvate including hydrate, clathrate, enantiomer, diastereomer, racemate, or mixture of stereoisomers thereof, wherein:

$R_1$ is hydrogen, saturated or unsaturated straight or branched substituted or unsubstituted alkyl, substituted or unsubstituted alkoxy, substituted or unsubstituted alkylamino, substituted or unsubstituted cycloalkyl, substituted or unsubstituted heterocycloalkyl, substituted or unsubstituted aryl, substituted or unsubstituted arylalkyl, substituted or unsubstituted heterocycloaryl or substituted or unsubstituted heteroaryl; wherein, if present, the substituent is at least one alkanoyl, imide, alkyl, hydroxy, halide, methoxy, ethoxy, carboxylic acid, cyano, nitro, alkanoyl, imide, acetal, acetylene, aminal, amino acid, amino acid ester, azo, diazo, azide, carbamate, carboxylic acid ester, carboalkoxy ester, cyanohydrin, diazonium salt, glucoside, glucuronide, halocarbon, polyhalocarbon, halocarbonoxy, polyhalocarbonoxy, hydroxylamine, ketone, lactone, nitrile, nitrile oxide, N-oxides, nucleoside linked, oxime, phosphate, phosphinate, phosphonate, phosphonic acid, quaternary ammonium salt, sulfoxide, sulfone, sulfonate ester, sulfinate ester, sulfonic acid, thioacetal, thiocarboxylic acid, thiol, or thioaryl.

preferably, $R_1$ is straight chain or branched, substitute or unsubstituted $C_1$–$C_{11}$ alkyl or unsaturated alkyl, $C_1$–$C_{12}$ alkoxy, substituted or unsubstituted $C_1$–$C_{11}$ alkylamino, substituted or unsubstituted 3 to 10 membered cycloalkyl, substituted or unsubstituted 3 to 10 membered heterocycloalkyl, substituted or unsubstituted 5 to 12 membered aryl, substituted or unsubstituted 5 to 12 membered arylalkyl, substituted or unsubstituted 4 to 13 membered heteroaryl, alkanoyl, or imide, wherein if present the substituent is at least one $C_1$–$C_4$ alkyl, cyano, fluoride, chloride, bromide, hydroxy, nitro, or thiol;

more preferably, $R_1$ is straight chain or branched, substitute or unsubstituted $C_1$–$C_8$ alkyl or unsaturated alkyl, $C_1$–$C_4$ alkoxy, substituted or unsubstituted $C_2$–$C_6$ alkylamino, substituted or unsubstituted 3 to 6 membered cycloalkyl, substituted or unsubstituted 4 to 6 membered heterocycloalkyl having at least one oxygen, nitrogen, or sulfur atom within the ring, substituted or unsubstituted 5 to 16 membered aryl, substituted or unsubstituted, 5 to 10 membered arylalkyl, substituted or unsubstituted 4 to 6 membered heteroaryl having at least one oxygen, nitrogen, or sulfur atom within the ring, $C_1$–$C_4$ alkanoyl, or imide, wherein substituent is at least one $C_1$–$C_4$ alkyl, cyano, fluoride, chloride, bromide, hydroxy, nitro, or thiol; and most preferably, $R_1$ is hydrogen, methyl, ethyl, propyl, isopropyl, sec-butyl, 3-methylbutyl, 2-methyl-2-propenyl, 2-propynyl, pentyl, hexyl, 2-butylyl, 2-hydroxy-2-(4-hydroxyphenyl)ethyl, 2-(2-pyridinyl)ethyl, 2-hydroxy-2-(3,4-dihydroxyphenyl)ethyl, 3-pyridinylmethyl, 2,5-difluorobenzyl, 4-trifluoromethoxyphenylmethyl, 3-methoxypropyl, 2-hydroxyethyl, 4-phenylbutyl, 2-phosphonatethyl, 3-(2-methyl)ethoxypropyl, 2-(2-thiophenyl)ethyl, N-benzyl-4-piperidinyl, 3-(1-pyrrolidinyl)propyl, 2-(N,N-diethyl)ethyl, tetrahydrofuranylmethyl, cyclopentyl, or cyclohexyl.

$R_3$ is hydrogen, halide, saturated or unsaturated straight or branched substituted or unsubstituted alkyl, hydroxy, substituted or unsubstituted alkoxy, substituted or unsubstituted aryl, substituted or unsubstituted arylalkyl, substituted or unsubstituted heterocycloalkyl, substituted or unsubstituted heterocycloaryl or substituted or unsubstituted heteroaryl; wherein, if present, the substituent is at least one alkanoyl, imide, alkyl, hydroxy, halide, methoxy, ethoxy, carboxylic acid, cyano, amine, alkylamine, amide, acetal, acetylene, aminal, amino acid, amino acid ester, azo, diazo, azide, carbamate, carboxylic acid ester, carboalkoxy ester, cyanohydrin, diazonium salt, glucoside, glucuronide, halocarbon, polyhalocarbon, halocarbonoxy, polyhalocarbonoxy, hydroxylamine, ketone, lactone, nitrile, nitrile oxide, N-oxides, nucleoside linked, oxime, phosphate, phosphinate, phosphonate, phosphonic acid, quaternary ammonium salt, sulfoxide, sulfone, sulfonate ester, sulfinate ester, sulfonic acid, thioacetal, thiocarboxylic acid, thiol, or thioaryl;

preferably, $R_3$ is hydrogen, $C_1$–$C_8$ straight chain or branched substituted or unsubstituted alkyl or unsaturated alkyl, substituted or unsubstituted 3 to 8 membered cycloalkyl, substituted or unsubstituted 5 to 16 membered aryl, substituted or unsubstituted 5 to 10 membered arylalkyl, or 4 to 12 membered heterocycloalkyl or heteroaryl with at least one oxygen, sulfur, or nitrogen atom within the ring, wherein, if present, the substituent is at least one hydroxy, halide, $C_1$–$C_4$ alkyl, $C_1$–$C_4$ alkoxy, $C_1$–$C_4$ sulfide, $C_1$–$C_4$ sulfonyl, nitro, carboxylic acid, ester, amine, or $C_1$–$C_4$ alkylamine;

more preferably, $R_3$ is $C_1$–$C_4$ straight chain or branched alkyl or unsaturated alkyl, substituted or unsubstituted 3 to 6 membered cycloalkyl, substituted or unsubstituted 5 to 12 membered aryl, substituted or unsubstituted 5 to 12 membered arylalkyl, or 4 to 12 membered heterocycloalkyl or heteroaryl with at least one oxygen, sulfur, or nitrogen within the ring, wherein, if present, the substituent is at least one hydroxy, fluoride, chloride, bromide, $C_1$–$C_4$ alkyl, $C_1$–$C_4$ alkoxy, $C_1$–$C_4$ sulfide, $C_1$–$C_4$ sulfonyl, nitro, carboxylic acid, ester, amine, or $C_1$–$C_4$ alkylamine; and most preferably, $R_3$ is a substituted or unsubstituted phenyl, substituted or unsubstituted pyrrolidinyl, substituted or unsubstituted pyrrolyl, substituted or unsubstituted piperidinyl, substituted or unsubstituted pyridinyl, substituted or unsubstituted quinolinyl, substituted or unsubstituted acridinyl, substituted or unsubstituted thiazolyl, substituted or unsubstituted benzodioxanyl, substituted or unsubstituted benzimidazolyl, substituted or unsubstituted phenylphenolyl, wherein, if present, the substituents are at least one $C_1$–$C_4$ alkyl, $C_1$–$C_4$ alkoxy, $C_1$–$C_4$ sulfide, $C_1$–$C_4$ sulfonyl, nitro, fluoride, chloride, or bromide.

$R_4$, $R_{4'}$, $R_5$, $R_{5'}$, $R_6$, $R_8$, $R_{8'}$, $R_9$, and $R_{9'}$ are as defined above for Formula III.

$R_7$, $R_{7'}$, $R_{10}$, and $R_{10'}$ each independently is defined as $R_4$ as defined for Formula III.

The letter "m" is an integer from 0 to about 4; preferably from 0 to 1; and more preferably, m is an integer of 1.

In another embodiment of the compounds of Formula V, $R_{4'}$, $R_{5'}$, $R_{7'}$, $R_{8'}$, $R_{9'}$, and $R_{10'}$ are hydrogen. In another embodiment of the compounds of Formula V, $R_1$ is hydrogen. In another embodiment of the compounds of Formula V, at least one $R_4$, $R_{4'}$, $R_8$, or $R_{8'}$, is not hydrogen. In another embodiment of the compounds of Formula V, at least two $R_4$, $R_{4'}$, $R_8$, and $R_{8'}$, are not hydrogen. In another embodiment of the compounds of Formula V, at least three $R_4$, $R_{4'}$, $R_8$, and $R_{8'}$, are not hydrogen. In another embodiment of the compounds of Formula V, at least one $R_5$, $R_{5'}$, $R_9$, or $R_{9'}$, is not hydrogen. In another embodiment of the compounds of Formula V, at least two $R_5$, $R_{5'}$, $R_9$, and $R_{9'}$, are not hydrogen. In another embodiment of the compounds of Formula V, at least three $R_5$, $R_{5'}$, $R_9$, and $R_{9'}$, are not hydrogen. In another embodiment of the compounds of Formula V, at least one $R_7$, $R_{7'}$, $R_{10}$, or $R_{10'}$ is not hydrogen. In another embodiment of the compounds of Formula V, at least two $R_7$, $R_{7'}$, $R_{10}$, and $R_{10'}$ are not hydrogen. In another embodiment of the compounds of Formula V, at least three $R_7$, $R_{7'}$, $R_{10}$, and $R_{10'}$ are not hydrogen.

In another embodiment, the 2-position of the benzimidazole ring is substituted with an amino group, with reference to Formula I, $R_3$ is a substituted or unsubstituted benzimidazolyl, X is a bond, Y is nitrogen, and n is 0, thus, the present invention encompasses compounds of the general Formula VI:

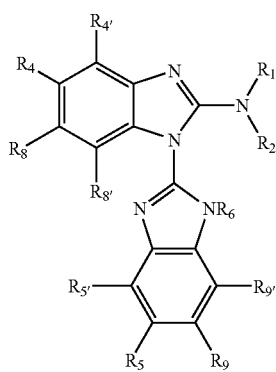

Formula VI or a pharmaceutically-acceptable prodrug, salt, solvate including hydrate, clathrate, enantiomer, diastereomer, racemate, or mixture of stereoisomers thereof, wherein:

$R_1$ and $R_2$ are each independently: hydrogen, a straight or branched substituted or unsubstituted alkyl or unsaturated alkyl, substituted or unsubstituted cycloalkyl, substituted or unsubstituted heterocycloalkyl, substituted or unsubstituted aryl, substituted or unsubstituted heteroaryl, substituted or unsubstituted arylalkyl, or acetal, acetylene, aminal, amino acid, amino acid ester, azo, diazo, azide, carbamate, carboxylic acid ester, carboalkoxy ester, cyanohydrin, diazonium salt, glucoside, glucuronide, halocarbon, polyhalocarbon, halocarbonoxy, polyhalocarbonoxy, hydroxylamine, lactone, nitrile, nitrile oxide, N-oxides, nucleoside linked, oxime, quaternary ammonium salt, sulfoxide, sulfone, sulfonate ester, sulfinate ester, sulfonic acid, thioacetal, thiocarboxylic acid, thiol, thioaryl, or $R_1$ and $R_2$ may be joined to form a ring including a cycloalkyl, aryl, heterocycloalkyl or heteroaryl group;

preferably, $R_1$ and $R_2$ are each independently: $C_1$–$C_8$ straight chain or branched alkyl or substituted alkyl or unsaturated alkyl, substituted or unsubstituted 3 to 8 membered cycloalkyl, substituted or unsubstituted 5 to 16 membered aryl, substituted or unsubstituted 5 to 10 membered arylalkyl, 4 to 12 membered heterocycloalkyl or heteroaryl with at least one oxygen, sulfur, or nitrogen atom within the ring, wherein, if present, the substituent is at least one $C_1$–$C_4$ alkyl, hydroxy, halide, methoxy, ethoxy, carboxylic acid, ester, amine, or alkylamine;

more preferably, $R_1$ and $R_2$ are each independently: $C_1$–$C_4$ straight chain or branched alkyl or unsaturated alkyl, substituted or unsubstituted 3 to 6 membered cycloalkyl, substituted or unsubstituted 5 to 6 membered aryl, substituted or unsubstituted 5 to 8 membered arylalkyl, or 4 to 8 membered heterocycloalkyl or heteroaryl with at least one oxygen, sulfur, or nitrogen atom within the ring, wherein, if present, the substituent is at least one $C_1$–$C_4$ alkyl, hydroxy, fluoride, chloride, bromide, methoxy, ethoxy, carboxylic acid, ester, amine, or $C_1$–$C_4$ alkylamine; and most preferably, $R_1$ and $R_2$ are each independently: benzyl, cyclopentyl, cyclohexyl, isopropyl, propyl, butyl, methylene cyclopropyl, methylene cyclobutyl, or $R_1$ and $R_2$ are attached to form a pyrrolidinyl or piperidinyl ring.

$R_4$, $R_{4'}$, $R_5$, $R_{5'}$, $R_8$, $R_{8'}$, $R_9$, and $R_{9'}$ are each independently: hydrogen, halide, straight chained or branched substituted or unsubstituted alkyl or unsaturated alkyl, hydroxy, substituted or unsubstituted alkoxy, substituted or unsubstituted cycloalkyl, substituted or unsubstituted aryl, substituted or unsubstituted arylalkyl, substituted or unsubstituted heterocycloalkyl, or substituted or unsubstituted heteroaryl, amine, alkylamine, amide, carboxylic acid, ester, nitro, sulfide, sulfonyl, or sulfonamide;

preferably, $R_4$, $R_{4'}$, $R_5$, $R_{5'}$, $R_8$, $R_{8'}$, $R_9$, and $R_{9'}$ are each independently: hydrogen, $C_1$–$C_4$ alkyl, $C_1$–$C_4$ alkoxy, amine, $C_1$–$C_4$ alkylamine, $C_1$–$C_4$ amide, carboxylic acid, ester, halide, hydroxy, nitro, $C_1$–$C_4$ sulfide, $C_1$–$C_4$ sulfonyl, or sulfonamide;

more preferably, $R_4$, $R_5$, $R_8$, and $R_9$ are each independently: hydrogen, $C_1$–$C_2$ alkyl, $C_1$–$C_2$ alkoxy, amine, $C_1$–$C_2$ alkylamine, fluoride, chloride, bromide, hydroxy, nitro, $C_1$–$C_2$ sulfide, or $C_1$–$C_2$ sulfonyl;

more preferably, $R_{4'}$, $R_{5'}$, $R_{8'}$, and $R_{9'}$ are each independently, hydrogen, $C_1$–$C_2$ alkyl, $C_1$–$C_2$ alkoxy, amine, $C_1$–$C_2$ alkylamine, $C_1$–$C_2$ amide, carboxylic acid, $C_2$–$C_4$ ester, or sulfonamide;

most preferably, $R_4$, $R_5$, $R_8$, and $R_9$ are each independently: hydrogen, methyl, methoxy, thiomethyl, fluorine, chlorine, nitro, or methylsulfonyl; and most preferably, $R_{4'}$, $R_{5'}$, $R_{8'}$, and $R_{9'}$ are each independently, hydrogen, methyl, methyl ester, ethyl ester, $C_1$–$C_2$ amide, carboxylic acid, methoxy, or sulfonamide.

$R_6$ is hydrogen, halide, straight chained or branched substituted or unsubstituted alkyl or unsaturated alkyl, hydroxy, substituted or unsubstituted alkoxy, substituted or unsubstituted cycloalkyl, substituted or unsubstituted aryl, substituted or unsubstituted arylalkyl, substituted or unsubstituted heterocycloalkyl, or substituted or unsubstituted heteroaryl, acetal, acetylene, aminal, amino acid, amino acid ester, azo, diazo, azide, carbamate, carboxylic acid ester, carboalkoxy ester, cyanohydrin, diazonium salt, glucoside, glucuronide, halocarbon, polyhalocarbon, halocarbonoxy, polyhalocarbonoxy, hydroxylamine, ketone, lactone, nitrile, nitrile oxide, N-oxides, nucleoside linked, oxime, phosphate, phosphinate, phosphonate, phosphonic acid, quaternary ammonium salt, sulfoxide, sulfone, sulfonate ester, sulfinate ester, sulfonic acid, thioacetal, thiocarboxylic acid, thiol or thioaryl;

preferably, $R_6$ is hydrogen, $C_1$–$C_8$ straight chain or branched substituted or unsubstituted alkyl or unsaturated alkyl, substituted or unsubstituted 3 to 8 membered cycloalkyl, substituted or unsubstituted 5 to 16 membered aryl, substituted or unsubstituted 5 to 10 membered arylalkyl, substituted or unsubstituted 4 to 12 membered heterocycloalkyl or heteroaryl with at least one oxygen, sulfur, or nitrogen atom within the ring, wherein, if present, the substituent is at least one hydroxy, halide, $C_1$–$C_4$ alkyl, $C_1$–$C_4$ alkoxy, $C_1$–$C_4$ sulfide, $C_1$–$C_4$ sulfonyl, nitro, carboxylic acid, ester, amine, or $C_1$–$C_4$ alkylamine;

more preferably, $R_6$ is $C_1$–$C_4$ straight chain or branched alkyl, substituted or unsubstituted 3 to 6 membered cycloalkyl, substituted or unsubstituted 5 to 12 membered aryl, substituted or unsubstituted 5 to 12 membered arylalkyl, or 4 to 12 membered heterocycloalkyl or heteroaryl with at least one oxygen, sulfur, or nitrogen atom within the ring, wherein, if present, the substituent is at least one hydroxy, fluoride, chloride, bromide, iodide, $C_1$–$C_4$ alkyl, $C_1$–$C_4$ alkoxy, $C_1$–$C_4$ sulfide, $C_1$–$C_4$ sulfonyl, nitro, carboxylic acid, ester, amine, or $C_1$–$C_4$ alkylamine; and most preferably, $R_6$ is a substituted or unsubstituted phenyl, substituted or unsubstituted pyrrolidinyl, substituted or unsubstituted pyrrolyl, substituted or unsubstituted piperidinyl, substituted or unsubstituted pyridinyl, substituted or unsubstituted quinolinyl, substituted or unsubstituted acridinyl, substituted or unsubstituted thiazolyl, substituted or unsubstituted benzodioxanyl, substituted or unsubstituted benzimidazolyl, substituted or unsubstituted phenylphenolyl, wherein, if present, the substituent is at least one $C_1$–$C_4$ alkyl, $C_1$–$C_4$ alkoxy, $C_1$–$C_4$ sulfide, $C_1$–$C_4$ sulfonyl, nitro, fluorine, chlorine, bromine, or iodine.

With the proviso that compounds of Formula VI do not include a compound where $R_1$, $R_2$, $R_4$, $R_{4'}$, $R_5$, $R_{5'}$, $R_6$, $R_8$, $R_{8'}$, $R_9$, $R_{9'}$ are hydrogen; or a compound where $R_4$, $R_{4'}$, $R_5$, $R_{5'}$, $R_8$, $R_{8'}$, $R_9$, and $R_{9'}$ are hydrogen, one of $R_1$ or $R_2$ is a hydrogen, and the other is a 4-piperidinyl or N-substituted 4-piperidinyl.

In another embodiment of the compounds of Formula VI, $R_{4'}$, $R_{5'}$, $R_{8'}$, and $R_{9'}$ are hydrogen. In another embodiment of the compounds of Formula VI, $R_6$ is hydrogen. In another embodiment of the compounds of Formula VI, at least two of $R_4$, $R_{4'}$, $R_8$, and $R_{8'}$ are not hydrogen. In another embodiment of the compounds of Formula VI, at least three of $R_4$, $R_{4'}$, $R_8$, and $R_{8'}$ are not hydrogen. In another embodiment of the compounds of Formula VI, at least two of $R_5$, $R_{5'}$, $R_9$, and $R_{9'}$ are not hydrogen. In another embodiment of the compounds of Formula VI, at least three of $R_5$, $R_{5'}$, $R_9$, and $R_{9'}$ are not hydrogen.

Other illustrative specific compounds encompassed by the invention include:

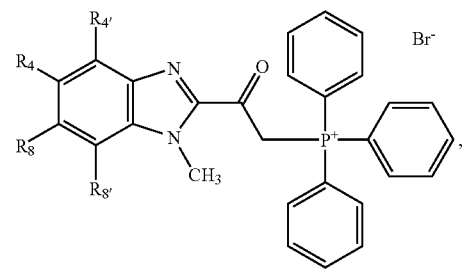

272

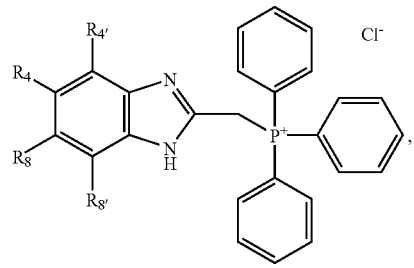

273

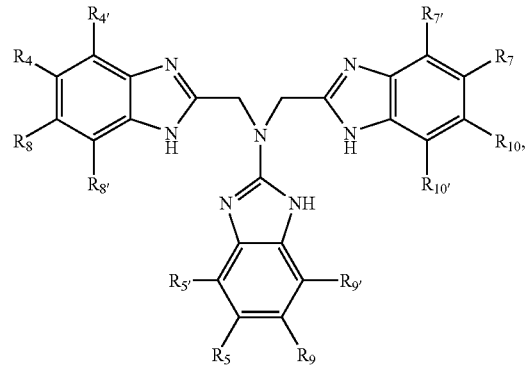

274

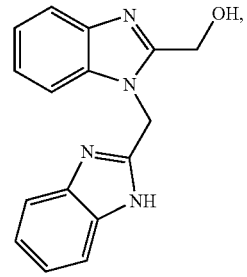

275

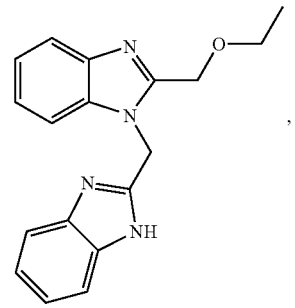

276

-continued

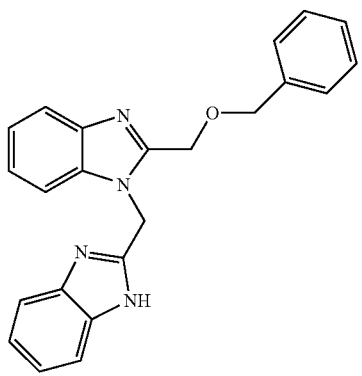

277 and

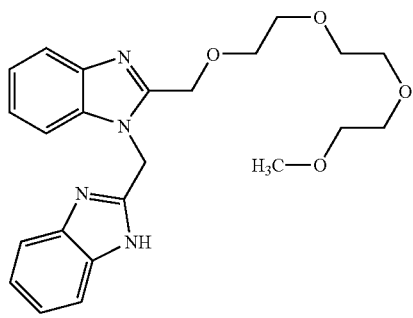

278 wherein $R_4$, $R_{4'}$, $R_5$, $R_{5'}$, $R_7$, $R_{7'}$, $R_8$, $R_{8'}$, $R_9$, $R_{9'}$, $R_{10}$, and $R_{10'}$ are as defined above for Formula V.

The compounds of the invention can contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass all of the corresponding enantiomers and stereoisomers, that is, both the stereomerically pure form (e.g., geometrically pure, enantiomerically pure, or diastereomerically pure) and enantiomeric and stereoisomeric mixtures.

A compound of the invention is considered optically active or enantiomerically pure (i.e., substantially the R-form or substantially the S-form) with respect to a chiral center when the compound is about 90% ee (enantiomeric excess) or greater, preferably, equal to or greater than 95% ee with respect to a particular chiral center. A compound of the invention is considered to be in enantiomerically-enriched form when the compound has an enantiomeric excess of greater than about 1% ee, preferably greater than about 5% ee, more preferably, greater than about 10% ee with respect to a particular chiral center. As used herein, a racemic mixture means about 50% of one enantiomer and about 50% of is corresponding enantiomer relative to all chiral centers in the molecule. Thus, the invention encompasses all enantiomerically-pure, enantiomerically-enriched, and racemic mixtures of compounds of Formulas I through XIV.

Enantiomeric and stereoisomeric mixtures of compounds of the invention can be resolved into their component enantiomers or stereoisomers by well-known methods. Examples include, but are not limited to, the formation of chiral salts and the use of chiral or high performance liquid chromatography "HPLC" and the formation and crystallization of chiral salts. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); Wilen, S. H., *Tables of Resolving Agents and Optical Resolutions* p. 268 (E. L. Eliel, Ed., Univ. of Notre Dame Press, Notre Dame, Ind., 1972); *Stereochemistry of Organic Compounds*, Ernest L. Eliel, Samuel H. Wilen and Lewis N. Manda (1994 John Wiley & Sons, Inc.), and *Stereoselective Synthesis A Practical Approach*, Mihály Nógrádi (1995 VCH Publishers, Inc., NY, N.Y.). Enantiomers and stereoisomers can also be obtained from stereomerically- or enantiomerically-pure intermediates, reagents, and catalysts by well-known asymmetric synthetic methods.

4.2 General Synthetic Methodology

The compounds of the invention can be obtained via standard, well-known synthetic methodology. Some convenient methods are illustrated in Schemes 1–8. These schemes are merely meant to be illustrative of one synthetic pathway, however, these synthetic pathways can be modified in ways that will be obvious to those skilled in the art to create a variety of benzimidazole compounds. Starting materials useful for preparing the compounds of the invention and intermediates therefore, are commercially available or can be prepared from commercially available materials using known synthetic methods and reagents. Such starting materials include, but are not limited to, 2-(chloromethyl)benzimidazole, 2-chlorobenzimidazole, 3,4-diaminobenzoic acid, 1-fluoro-2-nitrobenzene, and 3-fluoro-4-nitrotoluene, and amines. Amines include, but are not limited to, diisopropylamine, pyrrolidin-2-ylmethanol, 1-(3-trifluoromethylphenyl)-piperazine, piperidin-3-ylmethanol, morpholine, cyclohexyl-ethylamine, 1-(1H-pyrrol-2-yl)piperazine, and 1-(3-trifluoromethylphenyl)piperazine. Compounds used in the syntheses are commercially available from Aldrich Chemical Co. (Milwaukee, Wis.), Sigma® (St. Louis, Mo.), Fluka (Milwaukee, Wis.), and Maybridge (Cornwall, England).

Methods of synthesizing the compounds of the present invention are illustrated in the following schemes. Because of possible discrepancies in using chemical nomenclature where structures are provided for compounds or moieties the structure controls the definition of the compound or moiety, and not the chemical name. Representative synthetic schemes for the compounds of Tables 1–7 are shown below.

4.2.1 Synthesis of 1-MethylAlkyl/Aryl Substituted 2-MethylTertiary-Amine Benzimidazoles Benzimidazole compounds of Table 1 are synthesized by allowing 2-(chloromethyl)benzimidazole to react with one equivalent of a secondary amine in the presence of a base to obtain a tertiary amine. The secondary amine may be either purchased from commercial vendor, such as Aldrich Chemical Co. (Milwaukee, Wis.) or can readily be synthesized from known starting materials. A general method for synthesizing secondary amines is to allow a primary amine (1 eq.) to react with a halide in the presence of a base. Scheme 1 illustrates a method commonly known in the art to synthesize secondary amines.

Scheme 1

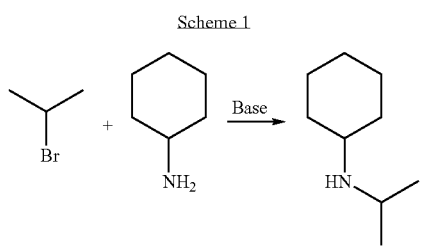

Scheme 2 illustrates a synthetic scheme for compounds of Tables 1–5. 2-(Chloromethyl)benzimidazole is allowed to react with a secondary amine (1 eq.) in the presence of a base to form a tertiary amine benzimidazole compound. Subsequently, either sequentially or stepwise, the ring nitrogen at the 1 position of the benzimidazole is deprotonated with a base and allowed to react with an alkyl, aryl, or alkylaryl halide to form compounds of the present invention. Optionally, the compounds are isolated by methods commonly used in the art, such as column chromatography, liquid chromatography, high pressure chromatography, among others. The compounds of the invention are solids or can be solidified by the formation of pharmaceutically acceptable salts by methods commonly used in the art.

An alternative method to synthesize the compounds of Tables 1–5 is shown in Scheme 3. 3,4-Diaminobenzene is allowed to react with chloroacetic acid to form 2-(chloromethyl)benzimidazole. Subsequently, 2-(chloromethyl)benzimidazole is allowed to react with a secondary amine (1 eq) in the presence of a base to form a tertiary amino benzimidazole compound. Finally, the tertiary amino benzimidizole compound is reacted with a substituted methylene bromide to form a methylbenzimidizole compound. If necessary, any functional group within the molecule can be protected using methods commonly known to the skilled artisan. Also, a chemical functional group can be converted into another chemical functional group, such as an aldehyde, ketone, ester, nitro, amine, etc. using methodology that is well known in the art. Optionally, the compounds are isolated by methods commonly used in the art, such as column chromatography, liquid chromatography, high pressure chromatography, among others.

Scheme 2

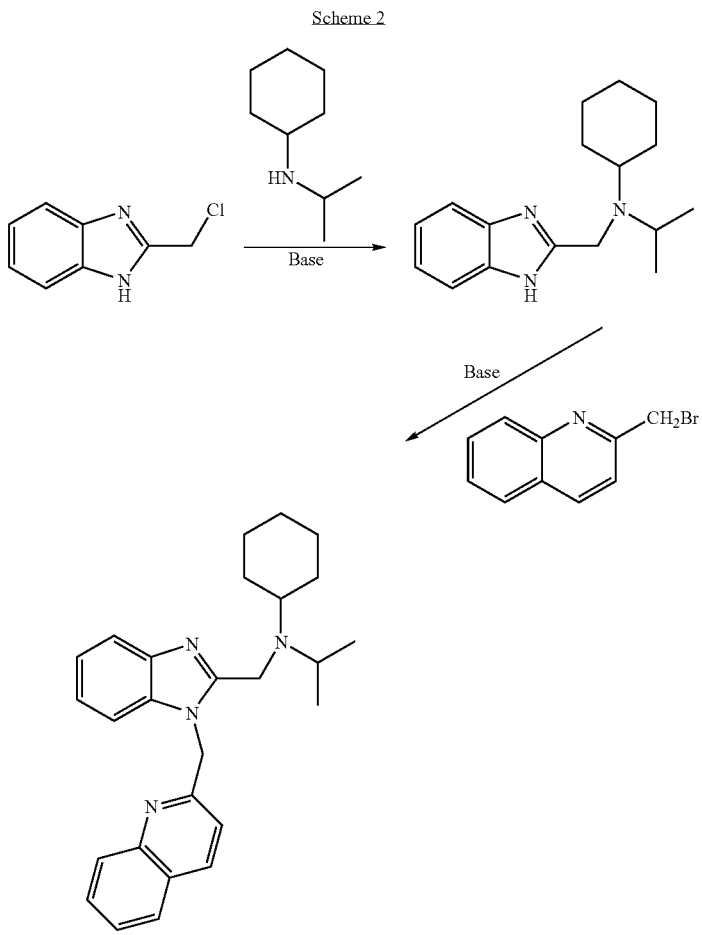

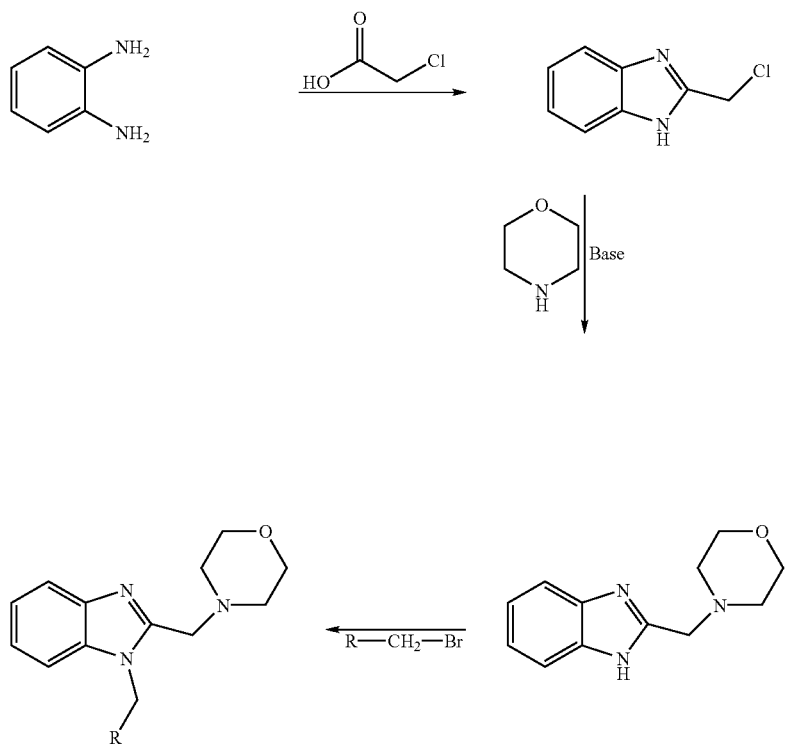

4.2.2 Synthesis of 1-methylbenzimidazole substituted Benzimidazoles

Representative examples of the compounds of Formula III are shown in Table 6, these examples are not meant to be limiting but are for illustrative purposes only. Scheme 4 illustrates a synthetic scheme for the compounds of Table 6.

One method to synthesize the benzimidazole compounds of Table 6 is to allow 2-(chloromethyl)benzimidazole to react in the presence of a base to form 1-benzimidazolyl-2-(chloromethyl)benzimidazole. Optionally, the ring nitrogen of the benzimidazole can be protected using protecting groups commonly known in the art, such as t-Boc. Thereafter, the 1-benzimidazolyl-2-(chloromethyl)benzimidazole is allowed to react with a secondary amine, such as those synthesized using Scheme 1, in the presence of a base to obtain the compounds of Table 6. Optionally, the compounds are isolated by methods commonly used in the art, such as column chromatography, liquid chromatography, high pressure chromatography, among others.

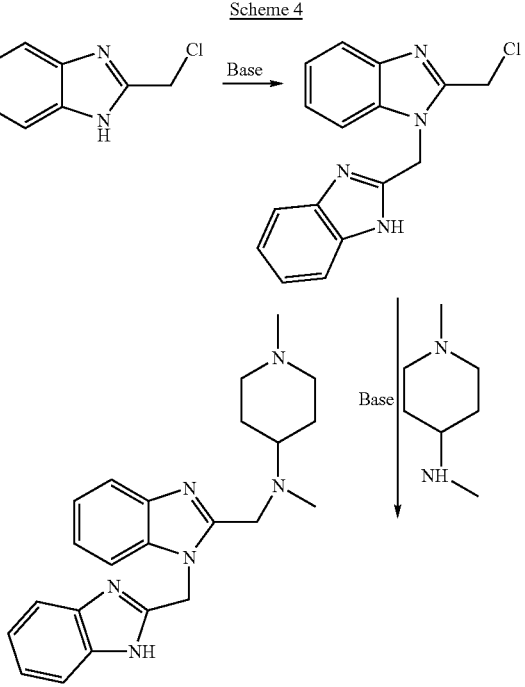

Optionally, depending upon the reaction conditions, the nitrogen at the 1-position of substituted or unsubstituted benzimidazole compounds can be protected from further reacting prior to allowing the benzimidazole compound with other reagents. Scheme 5 illustrates one method to protect the secondary nitrogen of benzimidazole, wherein 2-(chloromethyl)benzimidazole is allowed to react with t-BOC anhydride under basic conditions. It is understood that a skilled artisan can easily determine other methods within the scope of the invention to protect the nitrogen atom or other functional groups within the molecule as is necessary.

Scheme 6 illustrates another synthetic scheme for compounds of Table 8. Benzimidazole compounds of Table 8 are synthesized by allowing 4-aminomethylbenzimidazole-3-nitro benzoic acid methylester (3)to react with Chloromethyl-ethylimidate hydrochloride, after reduction to form 1-methylbenzimidazole-2-chloromethyl-5-methylcarboxylate benzimidazole (5). This intermediate can then be reacted with a nucleophile to yield 1-methylbenzimidazole-2-morpholinomethyl-5-methylcarboxylate benzimidazole, which after hydrolysis gives the resulting carboxylic acid (7), 1-methylbenzimidazole-2-morpholinomethyl-5-benzimidazole carboxylic acid (7). The carboxylic acid can then be converted to amides, ketones, or heterocyclic functionaries. Either the ester (6) or the acid (7) can also be reduced with Lithium aluminum hydride to give the benzylic alcohol which upon further manipulation, through well known methods in the art, can be converted to the alkyl halide, tosylate, and or mesylate. This resulting activated intermediate can be reacted with nucleophiles to give benzylic amines, ethers or any other chemical functional group using common methods know in the art.

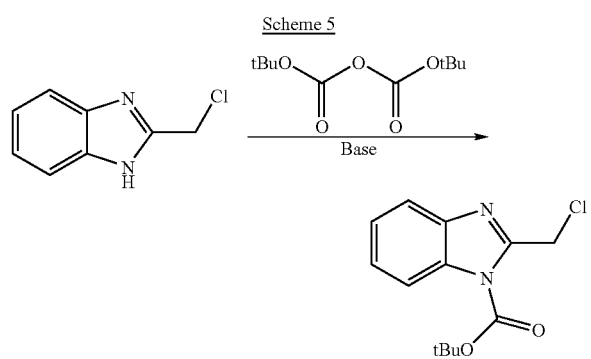

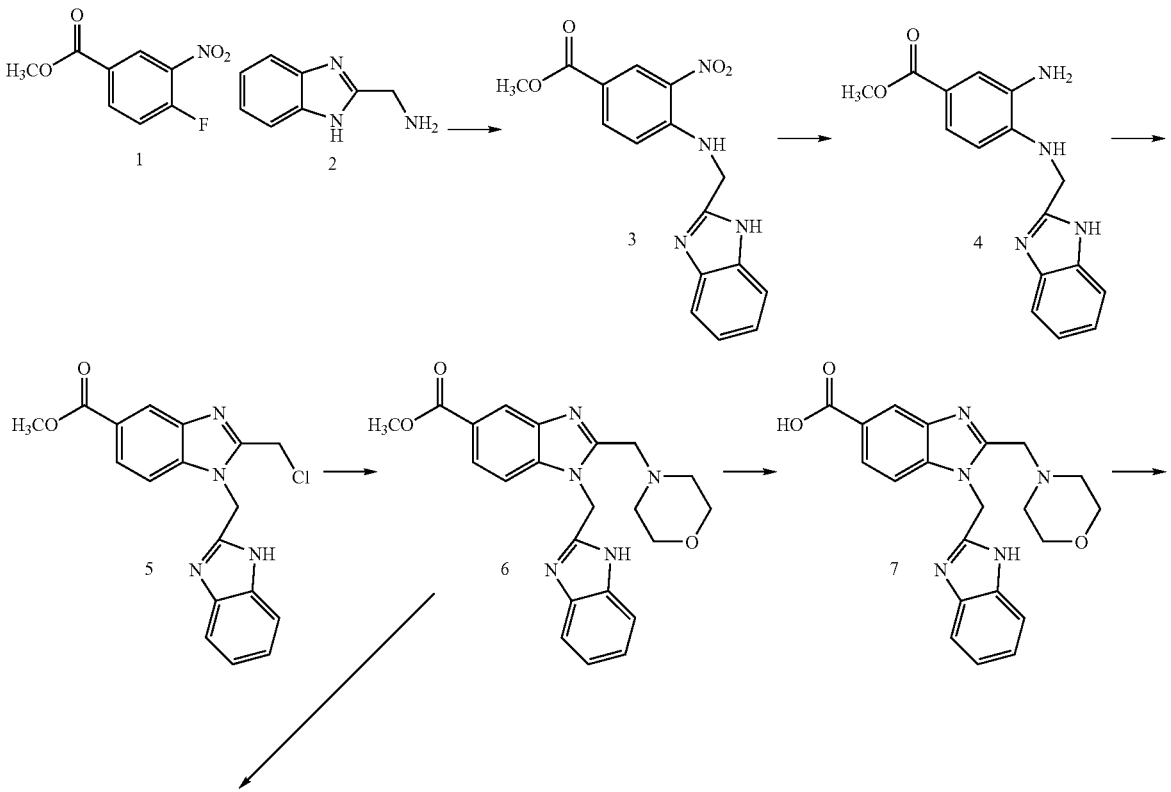

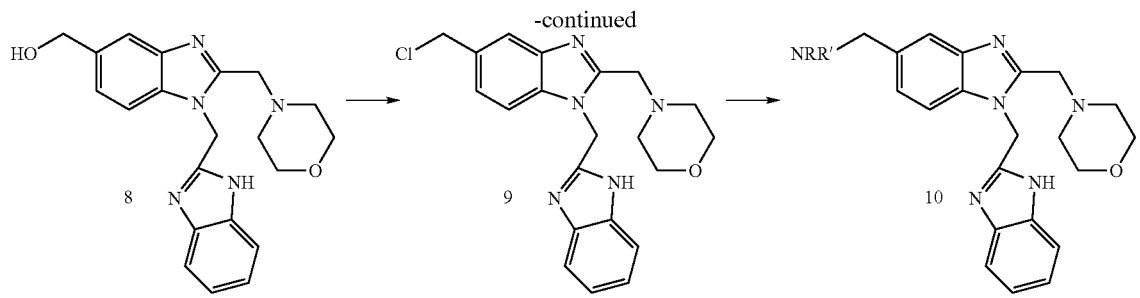

4.2.3 Synthesis of 2-Methylcycloalkyl and/or Aryl Substituted Benzimidazoles Representative examples of the compounds of Formula IV are shown in Table 7. The compounds of Formula IV can be synthesized according to Scheme 7. This scheme is not meant to be limiting but is for illustrative purposes only.

1-(N-t-BOC)-benzimidazolyl-2-(chloromethyl)benzimidazole, prepared using methodology described above, is allowed to react with a secondary amine, optionally a the secondary amine is a cyclic amine in the presence of a base to obtain the compounds of Table 7, after deprotection of the ring nitrogen. Optionally, the compounds are isolated by methods commonly used in the art, such as column chromatography, liquid chromatography, high pressure chromatography, among others.

4.2.4 Synthesis of 1-Methylbenzimidazolyl-2-methylamino(N-methylbenzimidazole)benzimidazole Compounds The compounds of Formula V can be synthesized according to Scheme 8. This scheme is not meant to be limiting but is for illustrative purposes only.

Scheme 8 illustrates a method commonly known in the art to synthesize the compounds of Formula V. 1-(N-t-BOC)-benzimidazolyl-2-(chloromethyl)benzimidazole is allowed to react in the presence of a base to form a 1-(N-t-BOC)-benzimidazolyl-2-(chloromethyl)benzimidazole, using methodology described above. Thereafter, the 1-benzimidazolyl-2-(chloromethyl)benzimidazole is allowed to react with N-methyl-1-t-BOC-2-(aminomethyl)benzimidazole in the presence of a base to obtain the compounds of Formula V, after deprotection of the ring nitrogen. Optionally, the compounds are isolated by methods commonly used in the art, such as column chromatography, liquid chromatography, high pressure chromatography, among others.

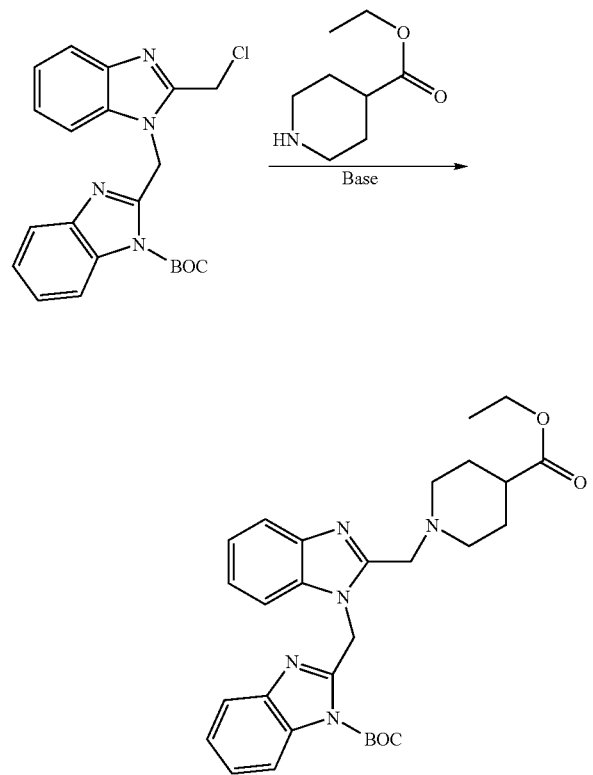

Scheme 7

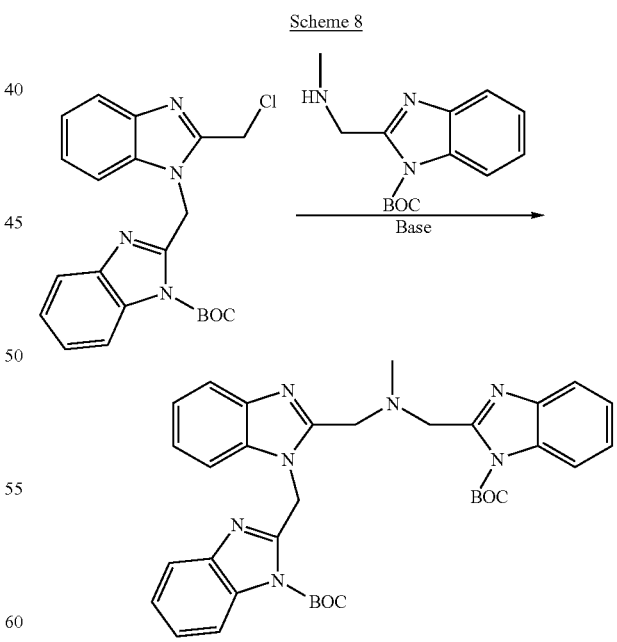

Scheme 8

4.3. Prophylactic and Therapeutic Uses

The invention encompasses the discovery of a novel benzimidazoles that are potent and selective antivirals. In particular, the compounds of the invention are selective for virally infected cells and thus have little or no cytotoxicity for healthy cells. As described in Section 6, the compounds within the invention were tested for both inhibitory concentrations (e.g., $IC_{50}$) and cytotoxicity concentration (e.g., $CC_{50}$) to demonstrate their unique selectivity (SI). Clearly, such compounds are particularly useful in vivo for the treatment or prevention of viral-mediated diseases or infections, particularly for RSV infections.

The $IC_{50}$ data is the concentration (μM) of the compounds that inhibits viral replication by about 50% relative to viral replication in the absence of the benzimidazole compound of the invention. The $CC_{50}$ data is the concentration (μM) of the compound that kills 50% of the healthy cells relative to amount of healthy cell death in the absence of the benzimidazole compound of the invention. The selective index (SI) is the ratio of the $CC_{50}/IC_{50}$.

In one embodiment, the benzimidazole compound has an $IC_{50}$ less than 1.0 μM. In preferred embodiments, the benzimidazole compound has an $IC_{50}$ of less than 1.0 μM, less than 0.9 μM, less than 0.8 μM, less than 0.7 μM, less than 0.6 μM, less than 0.5 μM, less than 0.4 μM, less than 0.3 μM, less than 0.2 μM, less than 0.1 μM, less than 0.09 μM, less than 0.08 μM, less than 0.07 μM, less than 0.06 μM, less than 0.05 μM, less than 0.04 μM, less than 0.03 μM, less than 0.02 μM, less than 0.01 μM, less than 0.005, or less than 0.0001. In one embodiment of the invention, the benzimidazole compound has an $IC_{50}$ from about 0.1 μM to about 0.5 μM, preferably from about 0.5 μM to about 0.01 μM, and most preferably from about 0.005 μM to about 0.01 μM. In other preferred embodiments, the $IC_{50}$ of the benzimidazole compound is no greater than 10 μM, preferably no greater than 8 μM, more preferably no greater than 5 μM, most preferably no greater than 3 μM.

In another embodiment, the benzimidazole compound has a $CC_{50}$ greater than 10 μM. In certain embodiments of the invention, the benzimidazole compound has a $CC_{50}$ greater than 20 μM, greater than 30 μM, greater than 35 μM, greater than 40 μM, greater than 45 μM, greater than 50 μM, greater than 55 μM, greater than 60 μM, greater than 65 μM, greater than 70 μM, greater than 75 μM, greater than 80 μM, greater than 85 μM, greater than 90 μM, greater than 95 μM, greater than 100 μM, greater than 110 μM, greater than 120 μM, greater than 130 μM, greater than 140 μM, greater than 150 μM, and greater than 200 μM. In one embodiment of the invention, the benzimidazole compound has a $CC_{50}$ from about 20 μM to about 50 μM, preferably from about 50 μM to about 100 μM, and most preferably from about 100 μM to about 150 μM.

The compounds of the invention are useful, particularly useful are the selective compounds, most particularly useful are the compounds with an SI above 20, preferably above 50, including compounds with SI's greater than 10,000. In one embodiment, the benzimidazole compound has an SI from about 50 to 6000, preferably greater than 100, and more preferably greater than 500, and most preferably greater than 1000.

The present invention encompasses methods for treating, ameliorating or preventing one or more symptoms associated with a viral infection, comprising the administration to a subject (e.g., a mammal, preferably a human) in need of such treatment or prevention a therapeutically or prophylactically effective amount of a benzimidazole compound of the invention. In various embodiments, a subject is administered a therapeutically or prophylactically effective amount of a benzimidazole compound of the invention or a pharmaceutically acceptable prodrug, salt, solvate, hydrate or clathrate thereof.

The present invention also encompasses methods for treating, ameliorating or preventing one or more symptoms associated with a viral infection by inhibiting viral membrane fusion associated events, comprising the administration of a therapeutically or prophylactically effective amount of a benzimidazole compound of the invention. In certain embodiments, a benzimidazole compound prevents a virus from fusing, attaching or inserting into its host cell's membrane. In other embodiments, a combination of benzimidazole compounds prevent a virus from fusing, attaching or inserting into its host cell's membrane.

The antifusogenic capability of the benzimidazole compounds of the invention may additionally be utilized to inhibit or treat/ameliorate symptoms caused by processes; involving membrane fusion events. Such events may include, for example, virus transmission via cell-cell fusion and abnormal neurotransmitter exchange via cell-fusion. In preferred embodiments, the benzimidazole compounds of the invention may be used to inhibit free viral transmission to uninfected cells wherein such viral infection involves membrane fusion events or involves fusion of a viral structure with a cell membrane.

In alternative embodiments, a benzimidazole compound of the present invention inhibits or downregulates viral replication. The benzimidazole compound inhibits or downregulates viral replication by at least 99%, at least 95%, at least 90%, at least 85%, at least 80%, at least 75%, at least 70%, at least 60%, at least 50%, at least 45%, at least 40%, at least 35%, at least 30%, at least 25%, at least 20%, or at least 10% relative to viral replication in the absence of said benzimidazole compounds. In other embodiments, a combination of benzimidazole compounds inhibit or downregulate viral replication. Viral replication is inhibited or downregulated by at least 99%, at least 95%, at least 90%, at least 85%, at least 80%, at least 75%, at least 70%, at least 60%, at least 50%, at least 45%, at least 40%, at least 35%, at least 30%, at least 25%, at least 20%, or at least 10% relative to viral replication in the absence of said benzimidazole compounds. The ability of one or more benzimidazoles of the invention to inhibit or downregulate viral replication may be determined by techniques described herein or otherwise known in the art. For example, the inhibition or downregulation of viral replication can be determined by detecting the viral titer in the tissues or body fluids of a subject.

In another embodiment, a subject is administered one or more benzimidazole compounds of the present invention for the treatment, prevention or amelioration of one or more symptoms associated with a viral infection in an amount effective for decreasing viral titers. In yet another embodiment, a subject is administered a dose of a benzimidazole compound of the present invention for the treatment or amelioration of one or more symptoms associated with a viral infection in an amount effective to reduce the severity or length of the viral infection or the dose effectively administered to a cotton rat that results in a viral titer in the rat 5 days after challenge with $10^5$ pfu of virus that is 99% lower than the viral titer 5 days after challenge with $10^5$ pfu of virus in a cotton rat not administered the dose prior to challenge.

In yet other embodiments, the compounds of the invention are administered to decrease viral load. One or more benzimidazole compounds reduces viral load by at least 99%, at least 95%, at least 90%, at least 85%, at least 80%, at least 75%, at least 70%, at least 60%, at least 50%, at least 45%, at least 40%, at least 35%, at least 30%, at least 25%, at least 20%, or at least 10% relative to viral load in the absence of said benzimidazole compounds. The ability of one or more benzimidazoles of the invention to reduce viral load may be determined by techniques described herein or otherwise known in the art. For example, the reduction in viral load can be determined by detecting the change in viral titer in the tissues or body fluids of a subject.

With respect to antiviral activity, the compounds of the invention inhibit the transmission of RSV. Accordingly, in a preferred embodiment, the present invention encompasses the administration of compounds of the invention for the inhibition of RSV transmission. The compounds of the invention also inhibit HPIV and influenza viruses. Accordingly, in other preferred embodiments, the present invention encompasses the administration of compounds of the invention for the inhibition of HPIV transmission and influenza virus transmission.

Also encompassed by the invention is the administration of compounds of the invention with antiviral activity against human retroviruses, such as but not limited to the human T-lymphocyte viruses (HTLV-I and II), and non-human retroviruses such as but not limited to, bovine leukosis virus, feline sarcoma and leukemia viruses, sarcoma and leukemia viruses, and sheep progress pneumonia viruses. Also encompassed is the administration of the compounds of the invention with antiviral activity against non-retroviral viruses such as but not limited to human respiratory syncytial virus, canine distemper virus, newcastle disease virus, human parainfluenza virus, influenza viruses, measles viruses, Epstein-Barr viruses, hepatitis B viruses, ebola virus and simian Mason-Pfizer viruses. Further encompassed by the invention is the administration of the compounds of the invention with antiviral activity against non-enveloped viruses including but are not limited to picornaviruses such as polio viruses, hepatitis A virus, enterovirus, echoviruses and coxsackie viruses, papovaviruses such as papilloma virus, parvoviruses, adenoviruses and reoviruses.

In specific embodiments, the present invention is directed to therapies which involve administering benzimidazole compounds of the invention to a subject, for preventing, treating, or ameliorating one or more symptoms associated with a RSV infection. In particular, the invention encompasses methods for treating, preventing or ameliorating symptoms associated with infections of the upper and/or lower respiratory tract, particularly those caused by RSV infection. Symptoms include but are not limited to influenza-like illnesses, persistent cold-like symptoms, cough, rhinities, mild fever, wheezing, severe cough, increased respiratory rate, symptoms associated with bronchiolitis and/or pneumonia, infection of the lungs, and exacerbation of other lung pathologies such as asthma and otitis media.

In other specific embodiments, the present invention is directed to therapies which involve administering benzimidazole compounds of the invention to a subject, for preventing, treating, or ameliorating one or more symptoms associated with a HPIV infection. In particular, the invention encompasses methods for treating, preventing or ameliorating symptoms associated with infections of the upper and/or lower respiratory tract, particularly those caused by HPIV infection. Symptoms include but are not limited to influenza-like illnesses, symptoms associated with bronchitis, bronchiolitis and/or pneumonia, infection of the lungs, and exacerbation of other lung pathologies such as asthma. In yet other embodiments, the present invention is directed to therapies which involve administering benzimidazole compounds of the invention to a subject, for preventing, treating, or ameliorating one or more symptoms associated with influenza.

Benzimidazole compounds of the present invention that function as inhibitors of membrane fusion can be administered to a subject, to treat, prevent or ameliorate one or more symptoms associated with a RSV infection. For example, benzimidazole compounds which disrupt or prevent the fusion a RSV virus and its host cell may be administered to a subject, to treat, prevent or ameliorate one or more symptoms associated with a RSV infection.

In a specific embodiment, a benzimidazole compound prevents RSV from fusing, attaching or inserting into its host cell's membrane. In another embodiment, a combination of benzimidazole compounds prevents RSV from fusing, attaching or inserting into its host cell's membrane.

Also contemplated by the invention is the administration of one or more benzimidazole compounds of the invention that function as inhibitors of membrane fusion to a subject to treat, prevent or ameliorate one or more symptoms associated with an HPIV infection or influenza.

In a specific embodiment, a benzimidazole compound prevents HPIV or influenza virus from fusing, attaching or inserting into its host cell's membrane. Thus, one or more benzimidazole compounds of the invention can be used to simultaneously treat or prevent HPIV, influenza virus or RSV infection in a patient in need thereof. In another embodiment, a combination of benzimidazole compounds prevents HPIV or influenza virus from fusing, attaching or inserting into its host cell's membrane.

In other specific embodiments, a benzimidazole compound of the present invention inhibits or downregulates RSV replication. RSV replication is inhibited or downregulated by at least 99%, at least 95%, at least 90%, at least 85%, at least 80%, at least 75%, at least 70%, at least 60%, at least 50%, at least 45%, at least 40%, at least 35%, at least 30%, at least 25%, at least 20%, or at least 10% relative to RSV replication in the absence of said benzimidazole compounds. In another embodiment, a combination of benzimidazole compounds inhibit or downregulate RSV replication. RSV replication is inhibited or downregulated by at least 99%, at least 95%, at least 90%, at least 85%, at least 80%, at least 75%, at least 70%, at least 60%, at least 50%, at least 45%, at least 40%, at least 35%, at least 30%, at least 25%, at least 20%, or at least 10% relative to RSV replication in the absence of said benzimidazole compounds. The ability of one or more benzimidazoles of the invention to inhibit or downregulate RSV replication may be determined by techniques described herein or otherwise known in the art. For example, the inhibition or downregulation of viral replication can be determined by detecting the RSV titer in the lungs of a subject.

In yet other specific embodiments, a benzimidazole compound of the present invention inhibits or downregulates HPIV or influenza virus replication. HPIV or influenza virus replication is inhibited or downregulated by at least 99%, at least 95%, at least 90%, at least 85%, at least 80%, at least 75%, at least 70%, at least 60%, at least 50%, at least 45%, at least 40%, at least 35%, at least 30%, at least 25%, at least 20%, or at least 10% relative to viral replication in the absence of said benzimidazole compounds. In another embodiment, a combination of benzimidazole compounds inhibit or downregulate HPIV or influenza virus replication. HPIV or influenza virus replication is inhibited or downregulated by at least 99%, at least 95%, at least 90%, at least 85%, at least 80%, at least 75%, at least 70%, at least 60%, at least 50%, at least 45%, at least 40%, at least 35%, at least 30%, at least 25%, at least 20%, or at least 10% relative to viral replication in the absence of said benzimidazole compounds. The ability of one or more benzimidazoles of the invention to inhibit or downregulate HPIV or influenza virus replication may be determined by techniques described herein or otherwise known in the art. For example, the inhibition or downregulation of viral replication can be determined by detecting the viral titer in the lungs of a subject.

In a preferred embodiment, one or more benzimidazole compounds of the invention are administered to a immunocompromised subject to treat, prevent or ameliorate one or more symptoms associated with RSV infection. In specific embodiments, one or more benzimidazole compounds of the invention are administered to a human with cystic fibrosis, bronchopulmonary dysplasia, congenital heart disease, congenital immunodeficiency or acquired immunodeficiency, or to a human who has had a bone marrow transplant to treat, prevent or ameliorate one or more symptoms associated with RSV infection. In other embodiments, one or more benzimidazole compounds of the invention are administered to a human undergoing cardiac, renal and lung transplants or to a human with leukemia. In other embodiments, one or more benzimidazole compounds of the invention are administered to a human infant, preferably a human infant born prematurely or a human infant at risk of hospitalization for RSV infection to treat, prevent or ameliorate one or more symptoms associated with RSV infection. In yet other embodiments, one or more benzimidazole compounds of the invention are administered to the elderly or people institutionalized or in group homes (e.g., nursing homes or rehabilitation centers).

In other preferred embodiments, one or more benzimidazole compounds of the invention are administered to a subject with symptoms common to RSV, HPIV or influenza virus infections. In particular, where there is difficulty diagnosing the viral infection causing the respiratory symptoms, one or more benzimidazole compounds of the invention are administered to a subject in need of such treatment.

In a specific embodiment, a subject is administered one or more benzimidazole compounds of the present invention for the treatment, prevention or amelioration of one or more symptoms associated with a RSV infection in an amount effective for decreasing RSV titers. In accordance with this embodiment, an effective amount of one or more benzimidazole compounds reduces the RSV titers in the lung as measured, for example, by the concentration of RSV in sputum samples or a lavage from the lungs from the subject in need of such treatment.

In yet another embodiment, a subject is administered a dose of a benzimidazole compound of the present invention for the treatment or amelioration of one or more symptoms associated with a RSV infection in an amount effective to reduce the severity or length of RSV infection or the dose effectively administered to a cotton rat that results in a RSV titer in the rat 5 days after challenge with $10^5$ pfu RSV that is 99% lower than the RSV titer 5 days after challenge with $10^5$ pfu of RSV in a cotton rat not administered the dose prior to challenge.

In another embodiment, a subject is administered a dose of a benzimidazole compound of the present invention for the treatment or amelioration of one or more symptoms associated with a RSV infection in an amount effective to reduce the viral load of the subject. In yet another embodiment a subject is administered a dose of a benzimidazole compound of the present invention for the treatment or amelioration of one or more symptoms associated with a HPIV infection or influenza in an amount effective to reduce the viral load of the subject.

Preferably, the dose of the benzimidazole compound of the present invention is 5 to 50 mg/kg/day, more preferably 10 to 40 mg/kg/day, most preferably 15 to 30 mg/kg/day. Administration may be made daily in either single or divided doses and the administration may be chronic or acute depending upon the use or disease to be treated or prevented.

Benzimidazole compounds of the invention may be provided in pharmaceutically acceptable compositions as known in the art or as described herein below. In various embodiments, therapeutic or pharmaceutical compositions comprising benzimidazole compounds of the invention are administered to a subject, to treat, prevent or ameliorate one or more symptoms associated with a viral infection. In preferred embodiments, the symptoms are associated with RSV infection.

In specific embodiments, therapeutic or pharmaceutical compositions comprising benzimidazole compounds of the invention are administered to a human with cystic fibrosis, bronchopulmonary dysplasia, congenital heart disease, congenital immunodeficiency or acquired immunodeficiency, or to a human who has had a bone marrow transplant to treat, prevent or ameliorate one or more symptoms associated with RSV infection. In other embodiments, therapeutic or pharmaceutical compositions comprising benzimidazole compounds of the invention are administered to a human infant, preferably a human infant born prematurely or a human infant at risk of hospitalization for RSV infection to treat, prevent or ameliorate one or more symptoms associated with. RSV infection. In yet other embodiments, therapeutic or pharmaceutical compositions comprising benzimidazole compounds of the invention are administered to the elderly or people in group homes (e.g., nursing homes or rehabilitation centers).

In a specific embodiment, a subject is administered a therapeutic or pharmaceutical composition comprising one or more benzimidazole compounds of the present invention for the treatment, prevention or amelioration of one or more symptoms associated with a RSV infection in an amount effective for decreasing RSV titers. In accordance with this embodiment, an effective amount of a pharmaceutical composition of the invention reduces the RSV titers in the lung as measured, for example, by the concentration of RSV in sputum samples or a lavage from the lungs from a subject.

4.3.1 Effective Dose

Toxicity and therapeutic efficacy of the compounds of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED$_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC$_{50}$ (i.e., the concentration of the test compound that achieves a half-maximal inhibition of symptoms, e.g., fusogenic events or viral infection, relative to the amount of the symptoms in the absence of the test compound) as determined in cell culture. Such information can be used to more accurately determine useful doses in humans. Levels in plasma may be measured, for example, by high performance liquid chromatography (HPLC).

4.4. Methods of Administration of Benzimidazole Compounds

The invention provides any method of administering an effective amount of a novel benzimidazole compound or pharmaceutical composition of the invention for the treatment, prophylaxis, or amelioration of one or more symptoms associated with a viral infection.

In particular embodiments, the invention provides for any method of administrating a novel benzimidazole compound of the invention for the prevention, treatment or amelioration of one or more symptoms associated with a RSV infection. As discussed herein below, novel benzimidazole compounds of the invention can be administered by oral, parenteral (intravenous, intramuscular, subcutaneous, Bolus injection), transdermal, mucosal (rectal, vaginal, buccal, sublingual) administration, preferably by oral or pulmonary administration (inhalation by aerosols or other known methods).

In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers.

In another embodiment, the composition can be delivered in a vesicle, in particular a liposome (see Langer, *Science* 249:1527–1533 (1990); Treat et al., in *Liposomes in the Therapy of Infectious Disease and Cancer*, Lopez-Berestein and Fidler (eds.), Liss, New York, pp. 353–365 (1989); Lopez-Berestein, ibid., pp. 3 17–327; see generally ibid.).

Various delivery systems are known and can be used to administer a benzimidazole compound of the invention, e.g., encapsulation in liposomes, microparticles, microcapsules, receptor-mediated endocytosis (see, e.g., Wu and Wu, *J. Biol. Chem.* 262:4429–4432 (1987)), etc. Methods of administering a benzimidazole compound include, but are not limited to, parenteral administration (e.g., intradermal, intramuscular, intraperitoneal, intravenous and subcutaneous), epidural, and mucosal (e.g., intranasal and oral routes). In a specific embodiment, benzimidazole compounds of the present invention or derivatives thereof, or pharmaceutical compositions are administered intramuscularly, intravenously, or subcutaneously. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

Preferably, pulmonary administration is employed, e.g., by use of an inhaler or nebulizer, and formulation with an aerosolizing agent. See, e.g., U.S. Pat. Nos. 5,985,320, 5,985,309, 5,934,272, 5,874,064, 5,855,913, and 5,290,540; and PCT Publication Nos. WO 92/19244, WO 97/32572, WO 97/44013, WO 98/31346, and WO 99/66903, each of which is incorporated herein by reference their entirety. In a preferred embodiment, an benzimidazole compound of the invention or composition of the invention is administered using Alkermes AIR™ pulmonary drug delivery technology (Alkermes, Inc., Cambridge, Mass.).

In other embodiments, the composition can be delivered using a surface active material and instilling or spraying the resulting suspension into the airway of a subject as described in U.S. Pat. No. 4,397,839 which is incorporated by reference in its entirety.

In yet another embodiment, the composition can be delivered in a controlled release or sustained release system. In one embodiment, a pump may be used to achieve controlled or sustained release (see Langer, supra; Sefton, 1987, *CRC Crit. Ref. Biomed. Eng.* 14:20; Buchwald et al., 1980, *Surgery* 88:507; Saudek et al., 1989, *N. Engl. J. Med.* 321:574). In another embodiment, polymeric materials can be used to achieve controlled or sustained release of the benzimidazole compounds of the invention or derivatives thereof (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J., Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 7 1:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the therapeutic target, i.e., the lungs, thus requiring only a fraction of the systemic dose (see, e.g., Goodson, in Medical Applications of Controlled Release, supra, vol. 2, pp. 115–138 (1984)).

Controlled release systems are discussed in the review by Langer (1990, *Science* 249:1527–1533). Any technique known to one of skill in the art can be used to produce sustained release formulations comprising one or more benzimidazole compounds of the invention and are discussed hereinbelow in Section 4.5 in more detail.

4.5. Pharmaceutical Compositions

Pharmaceutical compositions can be used in the preparation of unit dosage forms. Accordingly, pharmaceutical compositions and dosage forms of the invention comprise one or more of the novel benzimidazole compounds disclosed herein, or a pharmaceutically acceptable prodrug, polymorph, salt, solvate, hydrate, or clathrate thereof. The invention encompasses pharmaceutical compositions and unit dosage forms comprising at least one compound of general Formula I–XIV, preferably a benzimidazole of general Formula III, IV, or VII–XIV or a pharmaceutically acceptable prodrug, polymorph, salt, solvate, hydrate, clathrate, hydrate salt, or solvate salt thereof. Pharmaceutical compositions and dosage forms of the invention typically also comprise one or more pharmaceutically acceptable carriers.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered.

Suitable pharmaceutically acceptable carriers include essentially chemically inert and nontoxic pharmaceutical compositions that do not interfere with the effectiveness of the biological activity of the pharmaceutical composition. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (eg., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, for example, the materials sold as AVICEL-PH-101, AVICEL-PH-103 AVICEL RC-581, and AVICEL-PH-105 (available from FMC Corporation, American Viscose Division, Avicel Sales, Marcus Hook, Pa., U.S.A.). An exemplary suitable binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder/filler in pharmaceutical compositions of the present invention is typically present in about 50 to about 99 weight percent of the pharmaceutical composition.

Disintegrants are used in the compositions of the invention to provide tablets that disintegrate when exposed to an aqueous environment. Too much of a disintegrant will produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) should be used to form the dosage forms of the compounds disclosed herein. The amount of disintegrant used varies based upon the type of formulation and mode of administration, and is readily discernible to those of ordinary skill in the art. Typically, about 0.5 to about 15 weight percent of disintegrant, preferably about 1 to about 5 weight percent of disintegrant, can be used in the pharmaceutical composition.

Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not-limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel (AEROSIL 200, manufactured by W. R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass), or mixtures thereof. A lubricant can optionally be added, typically in an amount of less than about 1 weight percent of the pharmaceutical composition.

Examples of suitable pharmaceutical carriers are described in "Remington's Pharmaceutical Sciences" by E. W. Martin. Such compositions will contain a prophylactically or therapeutically effective amount of a benzimidazole compound of the invention, together with a suitable amount of carrier so as to provide the form for proper administration to the patient. The formulation should suit the mode of administration. For example, oral administration requires enteric coatings to protect the benzimidazole compound(s) from degradation within the gastrointestinal tract. In another example, the compound(s) may be administered in a liposomal formulation to shield the compound from degradative enzymes, facilitate transport, and effect delivery across cell membranes to intracellular sites.

In another embodiment, a pharmaceutical composition comprises a compound of the invention and/or one or more other therapeutic agents; and a pharmaceutically acceptable carrier. In a particular embodiment, the pharmaceutical composition comprises a compound of the invention, an antiviral, anti-inflammatory, anti-parasitic, anti-cancer or antibiotic agents, and a pharmaceutically acceptable carrier.

In one embodiment, a pharmaceutical composition, comprising a compound of the invention, with or without other therapeutic agents; and a pharmaceutically acceptable carrier, is at an effective dose.

Selection of the preferred effective dose can be determined (e.g., via clinical trials) by a skilled artisan based upon the consideration of several factors which will be known to one of ordinary skill in the art. Such factors include the particular benzimidazole compound, the compound's pharmacokinetic parameters such as bioavailability, metabolism, half-life, etc., which is established during the development procedures typically employed in obtaining regulatory approval of a pharmaceutical compound. Further factors in considering the dose include the disease to be treated, the benefit to be achieved in a patient, the patient's body mass, the patient's immune status, the route of administration, whether administration of the benzimidazole compound is acute or chronic, concomitant medications, and other factors known by the skilled artisan to affect the efficacy of administered pharmaceutical agents.

Pharmaceutical compositions can be used in the preparation of unit dosage forms. Examples of dosage forms include, but are not limited to: tablets, caplets, capsules, such as soft elastic gelatin capsules, cachets, troches, lozenges, dispersions, suppositories, ointments cataplasms (poultices), pastes, powders, dressings, creams, plasters, solutions, patches, aerosols (e.g., nasal sprays or inhalers), gels, liquid dosage forms suitable for oral or mucosal administration to a patient, including suspensions (e.g., aqueous or non-aqueous liquid suspensions, oil -in-water emulsions, or a water-in-oil emulsions), solutions, and elixers, liquid dosage forms suitable for parenteral administration to a subject; and sterile solids (e.g., crystalline or amorphous solids) that can be reconstituted to provide liquid dosage forms suitable for parenteral administration to a subject.

In one embodiment, the pharmaceutical composition comprises a compound of the invention at a unit dose of about 1.0 mg and a pharmaceutically acceptable carrier. A recommended dose of a benzimidazole compound of the invention is from about 1 mg to about 500 mg, more preferably from about 100 mg to about 400 mg, and even more preferably from about 200 mg to about 300 mg. For example, each tablet, cachet, or capsule contains from about 1 mg to about 500 mg, preferably from about 100 mg to about 400 mg, and more preferably from about 100 mg to about 300 mg of a benzimidazole.

As other examples of dosage forms, suitable dosage forms for mucosal or transdermal routes include, but are not limited to, transdermal patches, ophthalmic solutions, sprays, and aerosols. A recommended dose of a benzimidazole compound of the invention can be administered as a spray or aerosol at 5 to 40 mg/ml, preferably 10 to 30 mg/ml, and most preferably 15 to 20 mg/ml. Transdermal compositions can also take the form of creams, lotions, and/or emulsions, which can be included in an appropriate adhesive for application to the skin or can be included in a transdermal patch of the matrix or reservoir type as are conventional in the art for this purpose.

A preferred transdermal dosage form is a "reservoir type" or "matrix type" patch, which is applied to the skin and worn for a specific period of time to permit the penetration of a desired amount of active ingredient. For example, a preferred patch is worn for 24 hours and provides a total daily dose of from about 500 mg to about 2000 mg, more preferably from about 800 mg to about 1500 mg, and even more preferably from about 1000 mg to about 1300 mg per day. The patch can be replaced with a fresh patch when necessary to provide constant administration of the active ingredient to the patient.

In a preferred embodiment, the pharmaceutical compositions and dosage forms comprise a solid formulated for oral administration. Because of their ease of administration, tablets and capsules represent the most advantageous oral dosage unit forms, in which case solid pharmaceutical carriers are employed. If desired, tablets can be coated by standard aqueous or nonaqueous techniques. Pharmaceutical compositions of the invention suitable for oral administration can be presented as discrete dosage forms, such as capsules, cachets, or tablets, or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

In another preferred embodiment, the pharmaceutical compositions and dosage forms comprise aerosols suitable for pulmonary administration.

In other embodiments, the dosage form is a sterile, lyophilized powder suitable for reconstitution into a solution suitable for parenteral administration.

The actual amount of any particular compound of the invention administered can also depend on factors, such as, but not limited to, the type of viral infection, the toxicity of the compound to normal cells of the body, the rate of uptake of the compound by cells, the route of administration and the weight and age of the individual to whom the compound is administered. Because of the many factors present in vivo that may interfere with the action or biological activity of the compound, an effective amount of the compound may vary for each individual. Recommended daily doses can be given as a single once-a-day dose in the morning or as divided doses throughout the day.

Another embodiment of the invention encompasses a lactose-free pharmaceutical composition which comprises one or more compounds of the invention or a pharmaceutically acceptable prodrug, salt, solvate, or clathrate thereof and a pharmaceutically acceptable excipient. In a preferred embodiment the excipient is croscarmellose sodium, microcrystalline cellulose, pre-gelatinized starch, or magnesium stearate. In another preferred embodiment, the pharmaceutical compositions and dosage forms comprise a substantially free of mono- or di-saccharides.

In addition to the common dosage forms set out above, a benzimidazole of the invention can also be administered by controlled release means or delivery devices that are well known to those of ordinary skill in the art, such as those described in U.S. Pat. Nos.: 3,845,770; 3,916,899; 3,536, 809; 3,598,123; and 4,008,719, 5,674,533, 5,059,595, 5,591, 767, 5,120,548, 5,073,543, 5,639,476, 5,354,556, and 5,733, 566, the disclosures of which are incorporated herein by reference. These dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Advantages of controlled-release formulations include: 1) extended activity of the drug; 2) reduced dosage frequency; and 3) increased patient compliance. In addition, controlled-release formulations can be used to affect the time of onset of action or other characteristics, such as blood levels of the drug, and thus can affect the occurrence of side effects. Most controlled-release formulations are designed to a drug to maintain a therapeutic effect over an extended period of time. Controlled-release of an active ingredient can be stimulated by various inducers, including, but not limited to, pH, temperature, enzymes, water, or other physiological conditions or compounds.

Lactose-free compositions of the invention can comprise excipients which are well known in the art and are listed in the USP (XXI)/NF (XVI), which is incorporated herein by reference. In general, lactose-free compositions comprise an active ingredient, a binder/filler, and a lubricant in pharmaceutically compatible and pharmaceutically acceptable amounts. Preferred lactose-free dosage forms comprise an active ingredient, microcrystalline cellulose, pre-gelatinized starch, and magnesium stearate.

This invention further encompasses anhydrous pharmaceutical compositions and dosage forms comprising an active ingredient, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379–80. In effect, water and heat accelerate decomposition. Thus the effect of water on a formulation can be of great significance since moisture and/or humidity are commonly encountered during manufacture, handling, packaging, storage, shipment, and use of formulations.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastic or the like, unit dose containers, blister packs, and strip packs.

In this regard, the invention encompasses a method of preparing a solid pharmaceutical formulation comprising an active ingredient which method comprises admixing under anhydrous or low moisture/humidity conditions the active ingredient and an excipient (e.g., lactose), wherein the ingredients are substantially free of water. The method can further comprise packaging the anhydrous or non-hygroscopic solid formulation under low moisture conditions. By using such conditions, the risk of contact with water is reduced and the degradation of the active ingredient can be prevented or substantially reduced.

The invention also provides that a benzimidazole compound of the invention is packaged in a hermetically sealed container such as an ampoule or sachette indicating the quantity of benzimidazole compound. In one embodiment, the benzimidazole compound is supplied as a dry sterilized lyophilized powder or water free concentrate in a hermetically sealed container and can be reconstituted, e.g., with water or saline to the appropriate concentration for administration to a subject. In an alternative embodiment, an benzimidazole compound or derivative thereof is supplied in liquid form in a hermetically sealed container indicating the quantity and concentration of the benzimidazole compound or benzimidazole compound derivative.

4.6. Combination Therapies

In certain embodiments of the present invention, the compounds and compositions of the invention can be used in combination therapy with at least one other therapeutic agent. The compound of the invention and the therapeutic agent can act additively or, more preferably, synergistically. In a preferred embodiment, a compound or a composition comprising a compound of the invention is administered concurrently with the administration of another therapeutic agent that can be part of the same composition as the compound of the invention or a different composition. In another embodiment, a compound or a composition comprising a compound of the invention is administered prior or subsequent to administration of another therapeutic agent.

The present compounds and compositions can be administered together with an anti-inflammatory agent. Useful anti-inflammatory agents include, but are not limited to, non-steroidal anti-inflammatory drugs such as-salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; and other anti-inflammatory agents including, but not limited to, colchicine, allopurinol, probenecid, sulfinpyrazone and benzbromarone.

In other embodiments the compounds and compositions of the invention can be administered with another antiviral agent. Useful antiviral agents include, but are not limited to, nucleoside analogs, such as zidovudine, acyclovir, gangcyclovir, vidarabine, idoxuridine, trifluridine, and ribavirin, as well as foscarnet, amantadine, rimantadine, saquinavir, indinavir, ritonavir, and the alpha-interferons. Such additional antiviral agents which may be used with a compound of the invention include, but are not limited to, those which function on a different target molecule involved in viral replication, e.g., those which act on a different target molecule involved in viral transmission; those which act on a different loci of the same molecule; and those which prevent or reduce the occurrence of viral resistance. One skilled in the art would know of a wide variety of antiviral therapies which exhibit the above modes of activity.

In a preferred embodiment of the invention, the novel antiviral compounds of the present invention are used in combination with therapies known in the art, useful for treating or preventing RSV infection. By example and not by limitation, one or more compounds of the invention can be used advantageously in combination with anti-RSV agents such as, nucleoside analogs such as Ribavarin, monoclonal antibodies such as Synagis® and antisense oligonucleotides or other small molecule inhibitors of RSV.

In order to evaluate potential therapeutic efficacy of the benzimidazole compounds of the invention in combination with the antiviral therapeutics described above, these combinations may be tested for antiviral activity according to methods known in the art.

In other preferred embodiments, the novel antiviral compounds of the present invention are used in combination with supportive care, including administration of humidified oxygen and respiratory assistance.

4.7. Kits

The invention provides a pharmaceutical pack or kit comprising one or more containers filled with benzimidazole compound useful for the treatment, prevention, or amelioration of symptoms associated with RSV infection In other embodiments, the invention provides a pharmaceutical pack or kit comprising one or more containers filled with benzimidazole compound useful for the treatment, prevention, or amelioration of symptoms associated with RSV infection, HPIV infection or influenza.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5. Biological Assays for the Characterization and Demonstration of Antiviral Activity The benzimidazole compounds of the invention can also be assayed for their ability to inhibit or downregulate RSV replication using techniques known to those of skill in the art. For example, RSV replication can be assayed by a plaque assay such as described, e.g., by Johnson et al., 1997, *Journal of Infectious Diseases* 176:1215–1224. The benzimidazole compounds of the invention can also be assayed for their ability to inhibit or downregulate the expression of RSV polypeptides. Techniques known to those of skill in the art, including, but not limited to, Western blot analysis, Northern blot analysis, and room temperature-PCR can be used to measure the expression of RSV polypeptides, Further, the benzimidazole compounds of the invention can be assayed for their ability to prevent the formation of syncytia.

The benzimidazole compounds of the invention are preferably tested in vitro, and then in vivo for the desired therapeutic or prophylactic activity, prior to use in humans. For example, in vitro assays which can be used to determine whether administration of a specific benzimidazole compound or composition of the present invention is indicated, include in vitro cell culture assays in which a subject tissue sample is grown in culture, and exposed to or otherwise administered a benzimidazole compound or composition of the present invention, and the effect of such a benzimidazole compound or composition of the present invention upon the tissue sample is observed. In various specific embodiments, in vitro assays can be carried out with representative cells of cell types involved in a RSV infection (e.g., respiratory epithelial cells), to determine if a benzimidazole compound or composition of the present invention has a desired effect upon such cell types. Preferably, the benzimidazole compounds or compositions of the invention are also tested in in vitro assays and animal model systems prior to administration to humans. In a specific embodiment, cotton rats are administered a benzimidazole compound of the invention or a composition of the invention, challenged with $10^5$ pfu of RSV, and four or more days later the rats are sacrificed and RSV titer is determined. Further, in accordance with this embodiment, the tissues (e.g., the lung tissues) from the sacrificed rats can be examined for histological changes.

In accordance with the invention, clinical trials with human subjects need not be performed in order to demonstrate the prophylactic and/or therapeutic efficacy of benzimidazole compounds of the invention. In vitro and animal model studies using the benzimidazole compounds or fragments thereof can be extrapolated to humans and are sufficient for demonstrating the prophylactic and/or therapeutic utility of said benzimidazole compounds or benzimidazole compound derivatives.

Benzimidazole compounds or compositions of the present invention for use in therapy can be tested for their toxicity in suitable animal model systems, including but not limited to rats, mice, cows, monkeys, and rabbits. For in vivo testing of an benzimidazole compound or composition's toxicity any animal model system known in the art may be used.

Efficacy in treating or preventing viral infection may be demonstrated by detecting the ability of a benzimidazole compound or composition of the invention to inhibit the replication of the virus, to inhibit transmission or prevent the virus from establishing itself in its host, to reduce the incidence of RSV infection, or to prevent, ameliorate or alleviate one or more symptoms associated with RSV infection. The treatment is considered therapeutic if there is, for example, a reduction is viral load, amelioration of one or more symptoms, a reduction in the duration of a RSV infection, or a decrease in mortality and/or morbidity following administration of an benzimidazole compound or composition of the invention.

The ability of the benzimidazole compounds of the invention or fragments to block RSV-induced fusion after viral attachment to the cells is determined in a fusion inhibition assay.

Benzimidazoles may be tested for antiviral activity against RSV by a variety of methods known in the art. A common method is to test for the benzimidazole's effect on Hep2 cells, acutely infected with RSV, ability to fuse and cause syncytial formation on a monolayer of an infected line of cells (Hep2). The lower the observed level of fusion, the greater the antiviral effect of the benzimidazole is determined to be.

5.1. Assays for Membrane Fusion Activity

Assays for cell fusion events are well known to those of skill in the art, and may be used in conjunction with the compounds of the invention to test the compounds' antifusogenic capabilities.

Cell fusion assays are generally performed in vitro and are known in the art to correlate with in vivo activity including in humans. Such an assay may comprise culturing cells which, in the absence of any treatment would undergo an observable level of syncytial formation. For example, uninfected cells may be incubated in the presence of cells chronically infected with a virus that induces cell fusion. Such viruses may include, but are not limited to paramyxoviruses such as influenza virus, HPIV and in particular, RSV.

For the assay, cells are incubated in the presence of a compound to be assayed. For each compound, a range of compound concentrations may be tested. This range should include a control culture wherein no compound has been added.

Standard conditions for culturing cells, well known to those of ordinary skill in the art, are used. After incubation for an appropriate period (24 hours at 37° C, for example) the culture is examined microscopically for the presence of multinucleated giant cells, which are indicative of cell fusion and syncytial formation. Well known stains, such as crystal violet stain, may be used to facilitate the visualization of syncytial formation.

Exemplary cell fusion assays are described, below, in Section 6.

5.2. Assays for Membrane Antiviral Activity

The antiviral activity exhibited by the compounds of the invention may be measured, for example, by easily performed in vitro assays, such as those described below, which can test the compounds' ability to inhibit syncytia formation, or their ability to inhibit infection by cell-free virus. Using these assays, such parameters as the relative antiviral activity of the compounds, exhibit against a given strain of virus and/or the strain specific inhibitory activity of the compound can be determined A cell fusion assay may be utilized to test the compounds' ability to inhibit viral-induced, such as RSV-induced, syncytia formation in vitro. Such an assay may comprise culturing uninfected cells in the presence of cells chronically, infected with a syncytial-inducing virus and a compound to be assayed. For each compound, a range of compound concentrations may be tested. This range should include a control culture wherein no compound has been added. Standard conditions for culturing, well known to those of ordinary skill in the art, are used. After incubation for an appropriate period (24 hours at 37° C., for example) the culture is examined microscopically for the presence of multinucleated giant cells, which are indicative of cell fusion and syncytia formation. Well known stains, such as crystal violet stain, may be used to facilitate syncytial visualization.

Standard methods which are well-known to those of skill in the art may be utilized for assaying non-retroviral activity. See, for example, Pringle et al. (Pringle et al., 1985, J. Medical Virology 17:377–386) for a discussion of respiratory syncytial virus and parainfluenza virus activity assay techniques. Further, see, for example, "Zinsser Microbiology", 1988, Joklik, W. K. et al., eds., Appleton & Lange, Norwalk, Conn., 19th ed., for a general review of such techniques. These references are incorporated by reference herein in their entirety.

Additionally, anti-RSV activity can be assayed in vivo via well known mouse models that are standard models of human injection. For example, RSV can be administered intranasally to mice of various inbred strains. Virus replicates in lungs of all strains, but the highest titers are obtained in P/N, C57L/N and DBA/2N mice. Infection of BALB/c mice produces an asymptomatic bronchiolitis characterized by lymphocytic infiltrates and pulmonary virus titers of $10^4$ to $10^5$ pfu/g of lung tissue (Taylor et al., 1984, Infect. Immun. 43:649–655).

Cotton rat models of RSV are also well known (see, e.g., Johnson et al., 1999, Journal of Infectious Diseases 180: 35–40; Prince et al., 1985, J. Virol. 55:517–520). Virus replicates to high titer in the nose and lungs of the cotton rat but produces few if any signs of inflammation.

5.3. Test Results of Compounds

The assay utilized herein tested the ability of the benzimidazole compounds of the invention to selectively disrupt the ability of Hep2 cell monolayers acutely infected with RSV (i.e., cells which are infected with a multiplicity of infection of greater than 2) to fuse and cause syncytial formation. The lower the observed level of fusion, the greater the antiviral activity of the compound was determined to be.

Uninfected confluent monolayers (seeded at $2.2 \times 10^4$ cells/well) of Hep2 cells were grown in microtiter wells (96-well plates) in EMEM (Eagle Minimum Essential Medium w/o L-glutamine [Bio Whittaker Cat. No. 12-125F] with 3% fetal bovine serum (FBS; which had been heat inactivated for 30 minutes at 56° C., Bio Whittaker Cat. No. 14-501F), antibiotics (penicillin/streptomycin; Bio Whittaker Cat. No. 17-602E) added at 1%, and glutamine added at 1% (complete EMEM). The plates were incubated for 24 hours; and used for antiviral assays and cytotoxicity assays.

To prepare Hep2 cells for addition to uninfected cells, cultures of acutely infected Hep2 cells were washed with DPBS (Dulbecco's Phosphate Buffered Saline w/o calcium or magnesium; Bio Whittaker Cat. No. 17-512F) and cell monolayers were removed with Versene (1:5000; Gibco Life Technologies Cat. No. 15040-017). The cells were spun for 10 minutes and resuspended in 3% FBS. Cell counts were performed using a hemacytometer. Persistent cells were added to the uninfected Hep2 cells.

The antiviral assay was conducted by first removing all medium from the wells containing uninfected Hep2 cells, adding 100 µl complete EMEM, then adding benzimidazole compounds (eight 3-fold dilutions with 20 µM concentration as the highest final concentration) in 50 µl complete EMEM. Approximately 50 syncitial plaque forming units (PFU) of RSV in 50 µl was added per well and the plates were incubated in a $CO_2$ incubator at 37° C. for 48 hours. Each plate contained uninfected control wells and infected untreated control wells for calculation of % inhibition ($EC_{50}$) for each concentration.

After incubation, cells in control wells were checked for fusion centers, medium was removed from the wells followed by addition to each well of either Crystal Violet stain or XTT. With respect to Crystal Violet, approximately 50 µl 0.25% Crystal Violet stain in methanol was added to each well. The wells were rinsed immediately, to remove excess stain, and were allowed to dry. The number of syncytia per well were then counted, using a dissecting microscope.

With respect to XTT (2,3-bis[2-methoxy-4-nitro-5-sulfophenyl]-2H-tetrazolium-5-carboxyanilide inner salt), 50 µl XTT (1 mg/ml in RPMI buffered with 100 mM HEPES, pH 7.2–7.4, plus 5% DMSO) were added to each well. The $OD_{450/690}$ was measured (after blanking against growth medium without cells or reagents, and against reagents) according to standard procedures.

For antiviral assays at 48 hours post infection, cells in control wells were checked for syncytial plaques. Medium was removed from the wells followed by addition of approximately 50 µl Crystal Violet stain (0.25% Crystal Violet, 0.25% Giemsa dissolved in 10% formaldehyde, 70% methanol, and 20% $H_2O$). The wells were incubated at room temperature for 5 minutes, rinsed with $H_2O$ to remove excess stain, and allowed to dry. The number of syncytia per well were counted using a dissecting microscope. The 50% inhibitory concentration ($EC_{50}$) for each compound was calculated from the dose response curve.

Cytotoxicity assays were conducted by first removing all medium from the well containing uninfected Hep2 cells, adding 100 µl complete EMEM, and then adding benzimidazole compounds (eight 3-fold dilutions with 100 µM concentration as the highest final concentration). Complete EMEM (50 µl) was added to each well instead of virus and the plates were incubated in a $CO_2$ incubator at 37° C. for 48 hours.

At 48 hours, the cytotoxicity assays were developed by adding to each well 50 µl of XTT (1 mg/ml in PBS) containing 0.01–0.02 mM of the electron coupling agent phenazine methosulfate (PMS). The plates were incubated for 2–4 hours at 37° C. and then read in a 96-well plate reader at 450 nm. Plotting the % average OD of treated wells compared to the cell control vs. compound concentration generated dose response curves. $CC_{50}$ (50% inhibitory cytotoxic concentration) values for each compound were then calculated from these curves.

5.3.1. Results

The compounds listed in Tables 1–8 have been screened for inhibitory activity against RSV. The results are displayed in columns 3 and 4 of the tables above. For the results shown in Tables 1–8, the selective index (SI) is calculated as $IC_{50}$ (50% cell inhibitor concentration) over the $CC_{50}$ (50% cytotoxicity concentration) and is shown.

6. EXAMPLES

Certain embodiments of the invention are illustrated by the following non-limiting examples.

6.1 Synthesis of Benzimidazole Compounds

6.1.1 Synthesis of 1-(benzimidazol-2-ylmethyl)-2-(chloromethyl)benzimidazole (1)

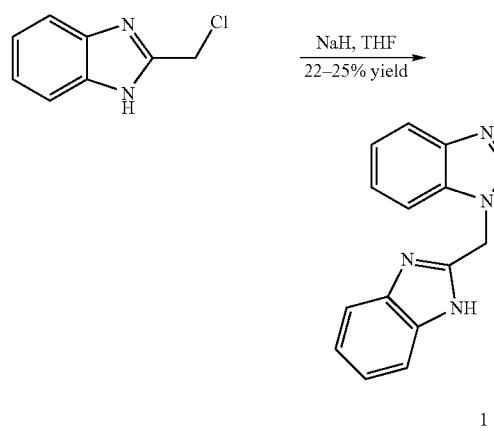

To a three-necked, 12 L flask, flushed with $N_2$, 2-(chloromethyl)benzimidazole (75 g, 0.45 mmol) and THF (10 L) were added, and the slurry was stirred for one hour at room temperature. Using an ice bath, the slurry was cooled to 0° C. and NaH (5.7 g, 95%, 0.23 mmol) was added. The slurry temperature increased to 4.5° C. The reaction mixture was stirred for 3 h and quenched with 150 g of silica gel. The slurry was concentrated to dryness under reduced pressure and purified using column chromatography (loaded with 40% EtOAc/hexanes, the eluting solvent started with 40% EtOAc/hexanes to end with 75% EtOAc/hexanes). 14.8 g of 1-benzimidazolylmethyl-2-(chloromethyl)benzimidazole 1 was obtained.

6.1.2 General Procedure for the Synthesis of 1-(benzimidazol-2-ylmethyl)-2-(N,N-disubstitutedaminomethyl)benzimidazole (2)

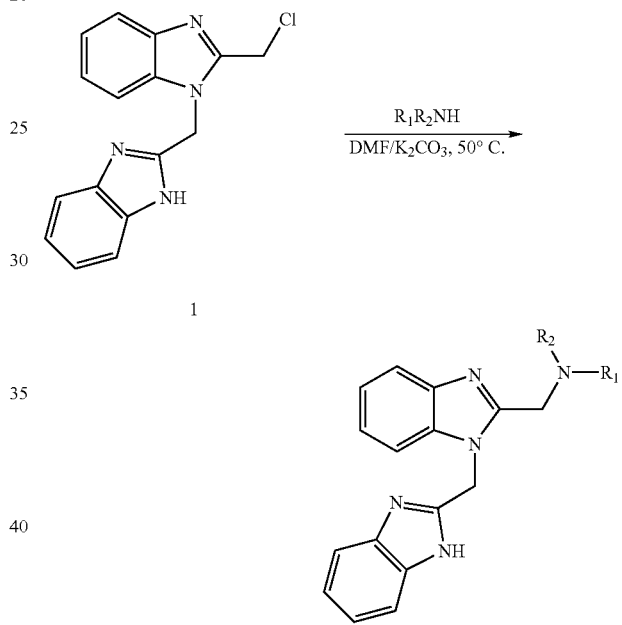

To 1-(benzimidazol-2-ylmethyl)-2-(chloromethyl)benzimidazole 1 (1 eq) was added to excess amine $R_1R_2NH$, and $K_2CO_3$ (5 eq.). The resulting slurry was diluted with DMF and stirred overnight at 50° C. The slurry was concentrated to dryness under reduced pressure, redissolved in MeOH, and filtered. The filtrate was concentrated to dryness under reduced pressure and stirred with 4 M HCl in EtOAc for one hour. The solvents were removed under reduced pressure, and the residue was dried in a vacuum oven at 40° C. overnight to obtain compound 2.

6.1.3 General Procedure for the Synthesis of 2-(N,N-disubstitutedaminomethyl)benzimidazole To a suspension of 2-(chloromethyl)benzimidazole (1 eq) in acetonitrile was added $K_2CO_3$ (1.5 eq.) and amine $HNR_1R_2$ (1.1 eq). The mixture was stirred until no 2-(chloromethyl)benzimidazole was detected using TLC analysis. The mixture was filtered and the solids washed with $CH_2Cl_2$. The combined organic filtrates were concentrated and the residue purified using column chromatography (silica; EtOAc/hexanes or CH$_2$Cl$_2$/MeOH).

6.1.4 General Procedure for the Synthesis of 1-(substitutedarylmethyl)-2-(N,N-disubstitutedaminomethyl)benzimidazole

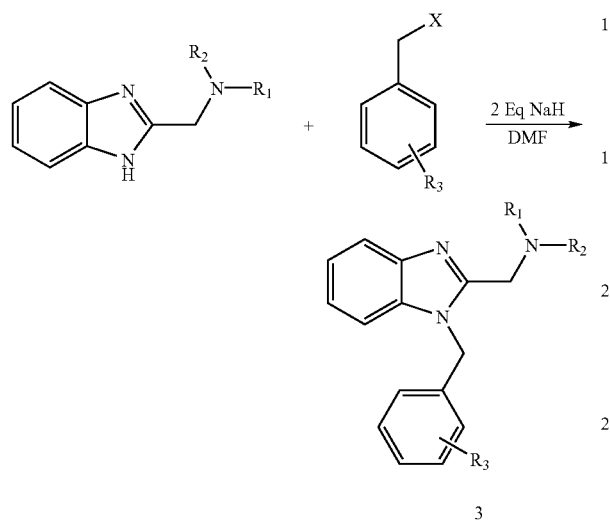

To a solution of 2-(N,N-disubstitutedaminomethyl)benzimidazole (1 eq) in DMF (anhydrous) was added NaH (95% dry, 2 eq) and the mixture was stirred at room temperature for 30 min. Aryl halide (1.18 eq) was added and the mixture was stirred at room temperature until no starting material was detected by TLC analysis. The reaction was quenched with water and extracted with EtOAc. The organic extract was concentrated and the residue purified by column chromatography (silica; EtOAc/hexanes or EtOAc/hexanes/NEt$_3$ or CH$_2$Cl$_2$/MeOH/concentrated NH$_4$OH). If the aryl halide was in the form of the HCl salt, then 3 eq. of NaH was used.

6.1.5 Synthesis of 2-(Chloromethyl)-1H-benzimidazole-5-Carboxylic Acid (4)

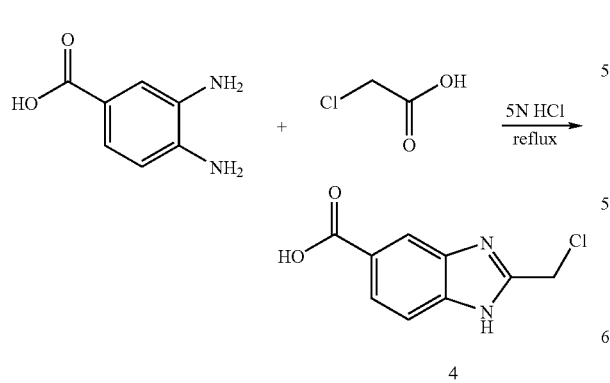

3,4-Diaminobenzoic acid (6.09 g, 40 mmol) and chloroacetic acid (4.35 g, 46 mmol) were refluxed in 5 N HCl (30 ml) for 5 h. The reaction mixture was cooled, the gray precipitate obtained was separated by filtration and subsequently washed with acetone (100 ml) and ether (100 ml) to obtain 6.44 g of product 4 (76%).

6.1.6 Synthesis of Methyl 2-(Chloromethyl)-1H-benzimidazole-5-Carboxylate (5)

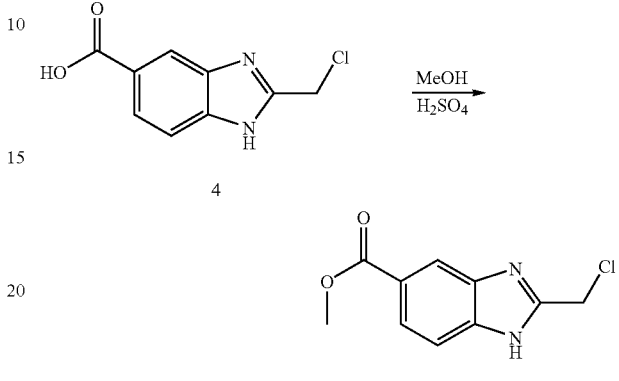

To 2-(Chloromethyl)-1H-benzimidazole-5-carboxylic acid (4) (0.5 g; 2.4 mmole) suspended in anhydrous methanol (20 ml) was added dropwise Sulfuric acid (0.2 ml). The reaction mixture was maintained at reflux for 16 hours. The solvent was evaporated to give the crude oily product, which was purified by column chromatography (silica, 10% methanol: dichloromethane) to obtain 0.4 g (71% yield) of product 5.

6.1.7 Synthesis of Methyl 2-(morpholinoaminomethyl)-1H-benzimidazole-5-Carboxylate (6)

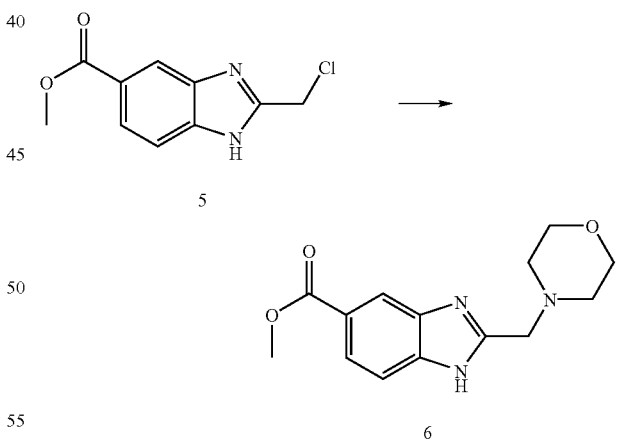

Methyl 2-(chloromethyl)-1H-benzimidazole-5-carboxylate (5) (0.5 g, 2.2 mmole), NaI (30 mg, 0.2 mmole), in 25 ml of anhydrous acetonitrile, add morpholine (0.48 ml, 5.50 mmole) and stir at ambient temperature for 5 hours. The solution was concentrated under reduced pressure and the resulting yellow solid redissolved in dichloromethane (20 ml) and washed with 10 ml of saturated bicarbonate solution. The organics were dried over anhydrous sodium sulfate and then concentrated to yield a fluffy solid (0.5 g, yield 81%) of 6.

6.1.8 Synthesis of 1-Acetyl-2-(chloromethyl)-1H-benzimidazole (7)

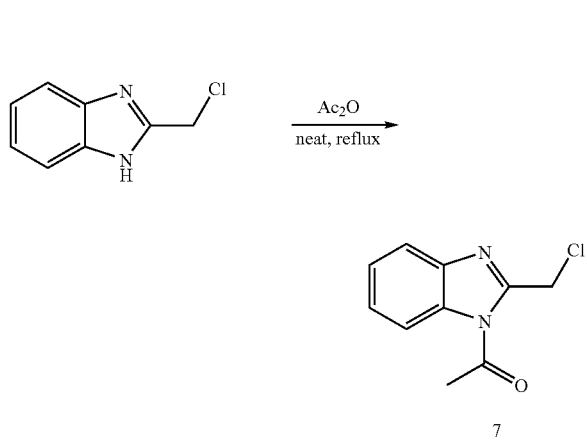

2-(Chloromethyl)-1H-benzimidazole (3.32 g, 0.02 mol) and DMAP (0.2 g) in Ac$_2$O (50 ml) were refluxed for 8 h. The excess Ac$_2$O was evaporated under vacuum and the residue was purified by column chromatography (silica, EtOAc:hexanes 2:1, first fraction) to obtain 2.37 g of product 7 (57%)

6.1.9 Synthesis of tert-Butyl 2-(Chloromethyl)-1H-benzimidazole-1-Carboxylate (8)

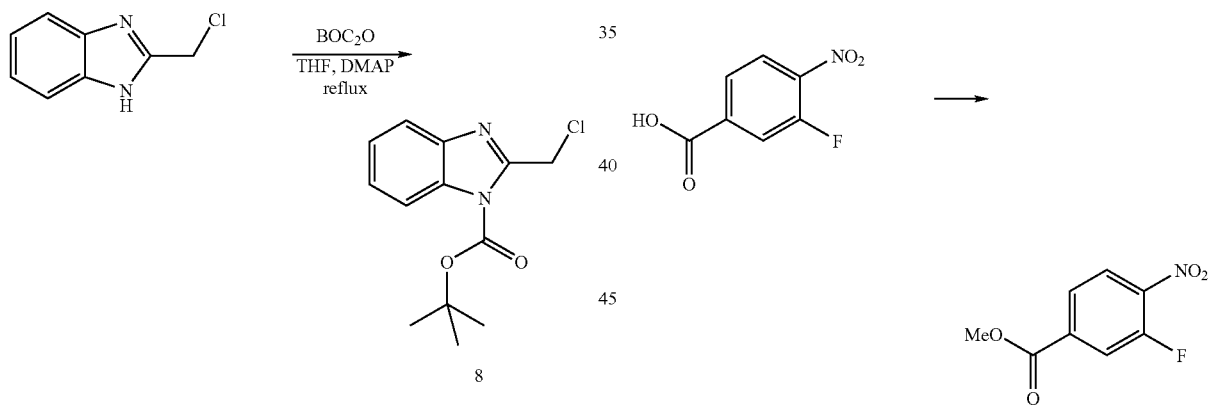

2-(Chloromethyl)-1H-benzimidazole (3.32 g, 0.02 mol), di-tert-butyl dicarbonate (4.4 g, 0.02 mol), and DMAP (0.2 g) in THF (100 ml) were refluxed for 8 h. The solvent was removed under reduced pressure and the residue was purified by column chromatography (silica, EtOAc:hexanes 2:1, first fraction) to obtain 2.13 g of product 8 (90%).

6.1.10 Synthesis of 2-(morpholin-4-ylmethyl)-1-(nitrilemethyl)benzimidazole (9)

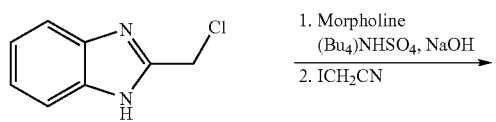

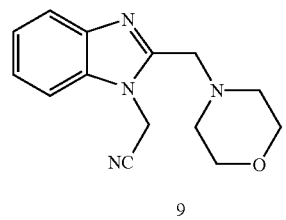

To a slurry of 2-chloromethyl-1H-benzimidazole (50 mg, 0.3 mmol, 1 eq) in 1.5 ml CH$_2$Cl$_2$ was added 1 ml of 2 N NaOH, morpholine (26.1 mg, 0.3 mmol, 1 eq), and 5 mg of (Bu)$_4$NHSO$_4$. The reaction was monitored by TLC analysis, and after 15 minutes, no starting materials were detected. Iodoacetonitrile (50 mg, 0.3 mmol, 1 eq) was added to the reaction mixture, and after 4 h, TLC analysis indicated that no starting material was present. The organic layer was separated and filtered through a pad of silica gel using CH$_2$Cl$_2$ as the eluent. The fractions containing the product 9 were combined and concentrated in vacuo to yield 41 mg (0.16 mmol, 54%).

6.1.11 Synthesis of 1-methylbenzimidazole-2-chloromethyl-6-methylcarboxylate benzimidazole (10)

Synthesis of 3-fluoro-4 nitro benzoic acid methylester

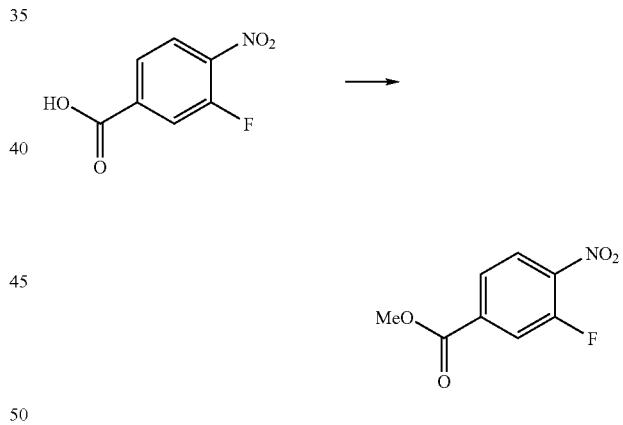

To a 500 ml flask under nitrogen atmosphere was charged 3-fluoro-4-nitro benzoic acid (10 g, 0.054 mol, 1 eq) and 250 ml of Toluene followed by DMF (210 ul, 3.7 mmol, 0.05 eq) and was heated to 70° C. At 40° C. thionyl chloride (8.0 ml, 0.11 mol, 2.0 eq) was added and the reaction was allowed to stir at 70° C. for 16 hours. The reaction was removed from the heat and placed in an ambient temperature bath. 100 ml of anhydrous methanol was added and then concentrated on rotary evaporator under reduced pressure, and bath temp of 45° C. The final volume was reduced to ~70 ml and slowly add hexane 100 ml with stiring to yield a light yellow solid, yield 97%. $^1$H NMR (Solvent CDCl$_3$), Singlet, 3 H, 3.99 ppm, Doublet of Doublets, 2H, 7.95 ppm, Triplet, 1H, 8.15 ppm. Thin Layer Chromatography elution 5% methanol/dichloromethane, Rf=0.9.

Synthesis of 3-aminomethylbenzimidazole-4 nitro benzoic acid methylester

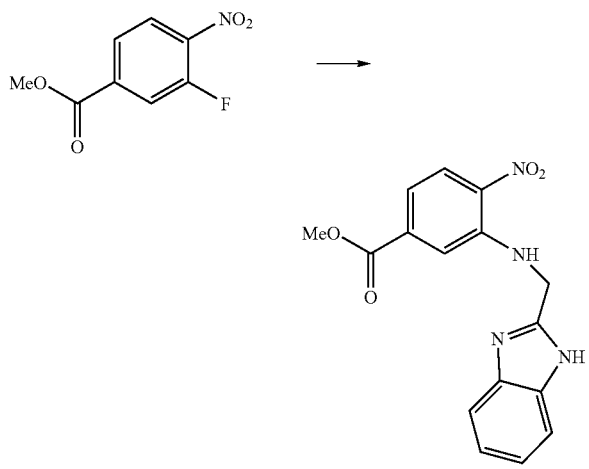

To a flask under nitrogen atmosphere was charged 500 ml of NMP and 3-fluoro-4 nitro benzoic acid methylester (15.64 g, 78.5 mmol, 1 eq) followed by aminomethyl-benzimidazole dihydrochloride (20.16 g, 91.6 mmol, 1.2 eq). To this, Diisopropyl ethylamine (55 ml, 316 mmol, 4 eq) was charged and stirred for 16 hours. The reaction was then poured into 1200 ml of ice water resulting in a yellow/orange solid. The solid was filtered and resuspended in 300 ml of cold water, stirred for 1 hour, filtered and dried to constant weight. Yield 85%, 18.8 g. TLC elution solvent system 5% methanol/95% dichloromethane, Rf=0.6.

Synthesis of 3-aminomethylbenzimidazole-4-aminobenzoic acid methyl ester

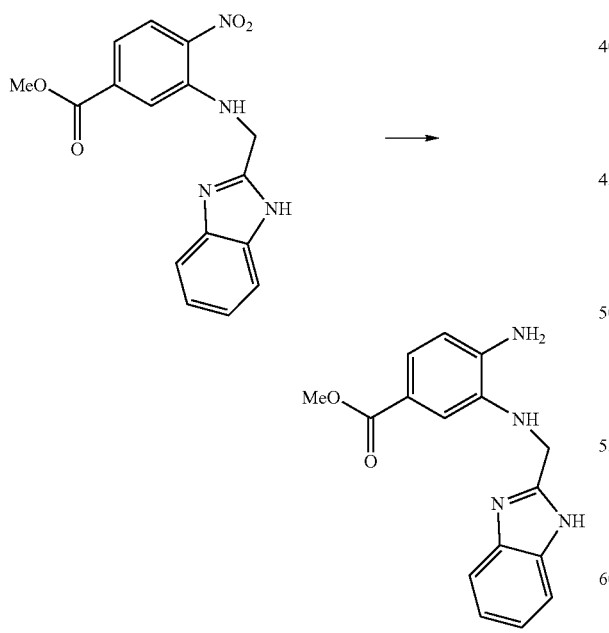

To a parr shaker under nitrogen atmosphere was charged 3-aminomethylbenzimidazole-4 nitro benzoic acid methylester (10 g, 0.037 mol, 1.0 eq) and 180 ml of methanol. To the slurry was charged 1 g of 10% Palladium on carbon This was placed under 55 psi hydrogen atmosphere and shaken for 16 hours. The reaction was removed under nitrogen atmosphere and filtered over a bed of celite under an atmosphere of nitrogen and the celite/Pd/c washed with 500 ml of methanol (degassed with nitrogen) and the combined organics concentrated to an off white solid. Yield 96%.

Synthesis of 1-methylbenzimidazole-2-chloromethyl-6-methylcarboxylate benzimidazole

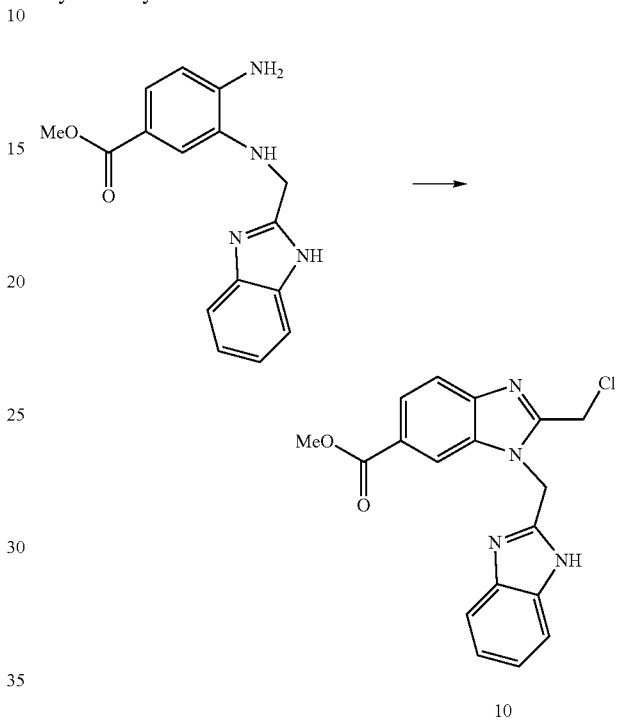

To a flask under nitrogen atmosphere was charged 3-aminomethylbenzimidazole-4-aminobenzoic acid methyl ester (2.0 g, 8.4 mmol, 1.0 eq) and methylchloro ethylimidate hydrochloride (4 g, 25.3 mmol, 3.0 eq) and 200 ml of methanol, heat to 65° C. for 16 hours. The reaction was then concentrated to a semisolid and chromatographed using 5% methanol, 95% dichloromethane. The fractions with product 10 were combined and concentrated to yield a solid. Yield 55%.

6.1.12 Synthesis of 1-(1H-Benzimidazol-2-ylmethyl)-2-morpholin-4-ylmethyl-1H-benzimidazole-6-carboxylic acid methyl ester (11)

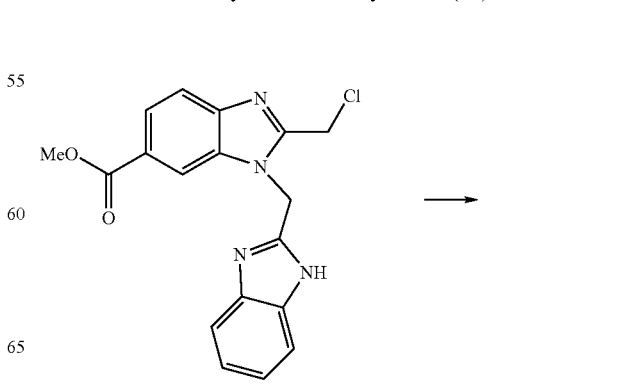

-continued

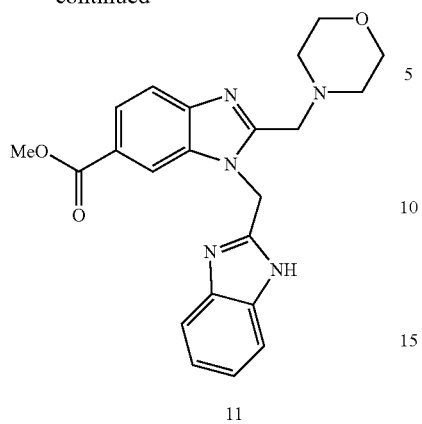

11

To a flask under nitrogen atmosphere was charged 1-methylbenzimidazole-2-chloro methyl-6-methylcarboxylate benzimidazole (2.5 g, 7.1 mMol, 1.0 eq) and 100 ml anhydrous Tetrahydrofuran. Then Sodium Iodide (105 mg, 0.7 mMol, 0.1 eq) and morpholine (2.0 ml, 22.9 mMol, 3.0 eq) were added and the reaction heated to 60° C. for 3 hours. TLC eluent 5% methanol/95% dichloromethane, Rf=0.55. Reaction mixture was cooled to ambient temperature and the resulting white solid filtered. The filtrate was concentrated under reduced pressure and then purified on silica using 5% methanol/95% dichloromethane. Yield 86% of product 11.

6.1.13 General Synthesis of 5-hydroxymethyl-2-(disubstitutedaminomethyl)-bisbenzimidazole (12)

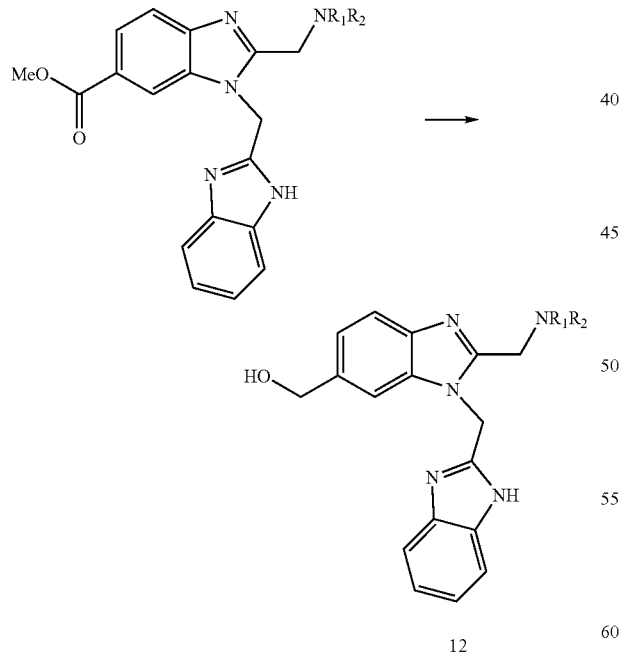

12

To a flask under nitrogen atmosphere was charged Lithium Aluminum Hydride (0.44 g, 11 mmol, 2 eq) and 40 ml of dry ethyl ether. To this was charged, in aliquots, a suspension consisting of 1-methylbenzimidazole-2-methyl dialkylamino-6-methylcarboxylate benzimidazole (2.05 g, 5.05 mmol, 1.0 eq) in 40 ml of anhydrous THF. The reaction was heated to 60° C. for 3 hours. TLC eluent 5% methanol/95% Dichloromethane. Yield 68% of product 12.

6.1.14 General Synthesis of 5-chloromethyl-2-(disubstitutedaminomethyl)-bis-benzimidazole (13)

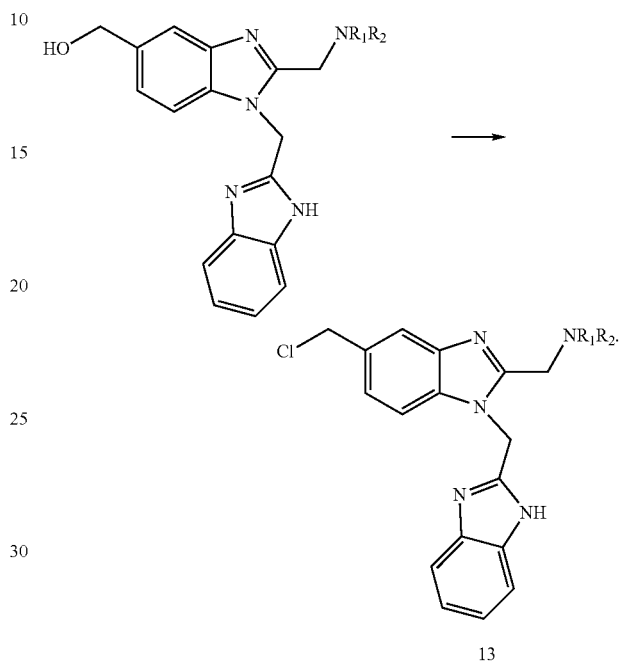

13

To a flask under nitrogen atmosphere was charged 5-hydroxymethyl-2-morpholinomethyl-bisbenzimidazole (1.9 g, 4.95 mmol, 1.0 eq) and 100 ml of anhydrous Tetrahydrofuran. To this was charged Thionyl Chloride (0.9 ml, 12.3 mmol, 2.5 eq) and the reaction heated to 50° C. for 16 hours. The reaction concentrated to a solid under reduced pressure and then triturated with 50 ml of hexane. The solid was purified on silica and eluted using 10% methanol/Dichloromethane. Yield 85% of product 13.

6.1.15 Synthesis of 5-morpholinomethyl-2 morpholinomethyl-bis-benzimidazole (14)

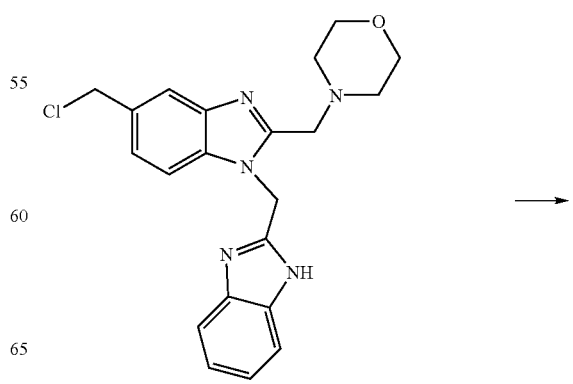

-continued

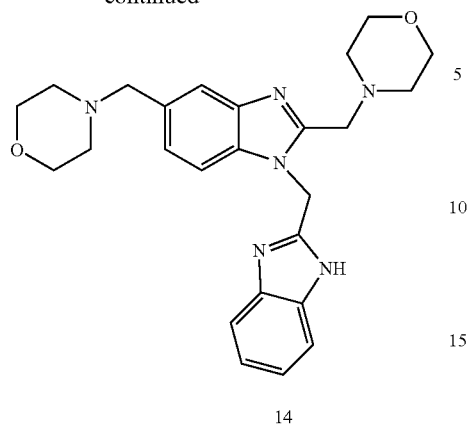

14

To a flask under nitrogen atmosphere was charged 5-chloromethyl-2 morpholinomethyl-bis-benzimidazole (3.0 g, 7.6 mMol, 1.0 eq) and 100 ml anhydrous Tetrahydrofuran. Then add Sodium Iodide (105 mg, 0.71 mMol, 0.1 eq) and morpholine (2.0 ml, 22.9 mMol, 3.0 eq) and the reaction heated to 60° C. for 16 hours. TLC eluent 5% methanol/95% dichloromethane, Rf=0.55. Reaction mixture was cooled to ambient temperature and resulting white solid filtered. The filtrate was concentrated under reduced pressure and then purified on silica using 5% methanol/95% dichloromethane. Yield 86% 5-morpholinomethyl-2 morpholinomethyl-bis-benzimidazole (14).

Equivalents

Those skilled in the art will recognize, or be able to ascertain using no more than routine experimentation, many equivalents to the specific embodiments of the invention described, herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

What is claimed is:

1. A compound of the Formula I:

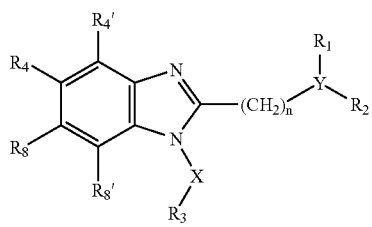

or a pharmaceutically-acceptable prodrug, salt, solvate, hydrate, enantiomer, diastereomer, racemate or mixture of stereoisomer thereof, wherein:

$R_1$ and $R_2$ are joined to form a substituted or unsubstituted ring, said substituted ring is a substituted heterocycloalkyl or a substituted 5, 6, 7 or 8 membered-heteroaryl, wherein, when $R_1$ and $R_2$ form said substituted ring, the substituent is at least one unsubstituted lower alkyl, substituted or unsubstituted lower alkoxy, amide, amine, sulfonamide, ester, hydroxy, halide, substituted or unsubstituted aryl, substituted or unsubstituted cycloalkyl, substituted or unsubstituted heterocycloalkyl, or unsubstituted heteroaryl;

$R_3$ is substituted or unsubstituted 2-benzimidazolyl;

$R_4$, $R_{4'}$, $R_8$, and $R_{8'}$ are each independently hydrogen, halide, saturated or unsaturated straight or branched substituted or unsubstituted alkyl, hydroxy, substituted or unsubstituted alkoxy, substituted or unsubstituted aryl, substituted or unsubstituted arylalkyl, substituted or unsubstituted heterocycloalkyl, substituted or unsubstituted heteroaryl, methyl ester, ethyl ester, $C_1$–$C_2$ amide, carboxylic acid, or sulfonamide;

X is a bond, straight chain or branched substituted or unsubstituted alkyl, -(alkyl)N—, -(alkyl)O—, —C=N—, carbonyl, phosphorus, or sulfur;

Y is nitrogen; and n is an integer from 0 to 4.

2. A compound of the Formula I:

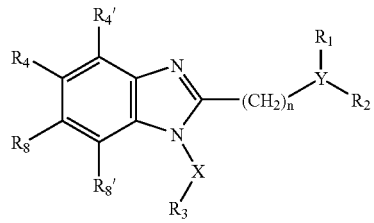

or a pharmaceutically-acceptable prodrug, salt, solvate, hydrate, enantiomer, diastereomer, racemate or mixture of stereoisomer thereof, wherein:

$R_1$ and $R_2$ are joined to form a substituted or unsubstituted ring wherein, when $R_1$ and $R_2$ form a substituted ring, the substituent is at least one unsubstituted lower alkyl, substituted or unsubstituted lower alkoxy, amide, amine, sulfonamide, ester, hydroxy, halide, substituted or unsubstituted aryl, substituted or unsubstituted cycloalkyl, substituted or unsubstituted heterocycloalkyl, or substituted or unsubstituted heteroaryl;

$R_3$ is substituted or unsubstituted 2-benzimidazolyl;

$R_4$, $R_{4'}$, $R_8$, and $R_{8'}$ are each independently hydrogen, halide, saturated or unsaturated straight or branched substituted or unsubstituted alkyl, hydroxy, substituted or unsubstituted alkoxy, substituted or unsubstituted aryl, substituted or unsubstituted arylalkyl, substituted or unsubstituted heterocycloalkyl, substituted or unsubstituted heteroaryl, methyl ester, ethyl ester, $C_1$–$C_2$ amide, carboxylic acid, or sulfonamide;

X is a bond, methylene, or ethylene;

Y is nitrogen; and n is 1.

3. A compound of the Formula I:

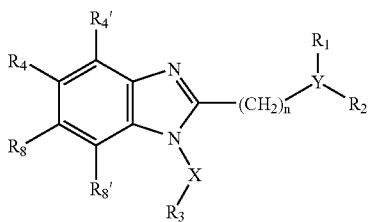

or a pharmaceutically-acceptable prodrug, salt, solvate, hydrate, enantiomer, diastereomer, racemate or mixture of stereoisomer thereof, wherein:

$R_1$ and $R_2$ are joined to form a substituted or unsubstituted ring wherein, when $R_1$ and $R_2$ form a substituted ring, the substituent is at least one unsubstituted lower alkyl, substituted or unsubstituted lower alkoxy, amide, amine, sulfonamide, ester, hydroxy, halide, substituted or unsubstituted aryl, substituted or unsubstituted cycloalkyl, substituted or unsubstituted heterocycloalkyl, or substituted or unsubstituted heteroaryl;

$R_3$ is substituted or unsubstituted 2-benzimidazolyl;

$R_4$, $R_{4'}$, $R_8$, and $R_{8'}$ are each independently hydrogen, halide, saturated or unsaturated straight or branched substituted or unsubstituted alkyl, hydroxy, substituted or unsubstituted alkoxy, substituted or unsubstituted aryl, substituted or unsubstituted arylalkyl, substituted or unsubstituted heterocycloalkyl, substituted or unsubstituted heteroaryl, methyl ester, ethyl ester, $C_1$–$C_2$ amide, carboxylic acid, or sulfonamide;

wherein said substituted or unsubstituted 2-benzimidazolyl is substituted with at least one $C_1$–$C_4$ alkyl, $C_1$–$C_4$ alkoxy, $C_1$–$C_4$ sulfide, $C_1$–$C_4$ sulfonyl, nitro, fluoride, chloride, or bromide;

X is a methylene;

Y is nitrogen; and n is 1.

4. A compound of the Formula I:

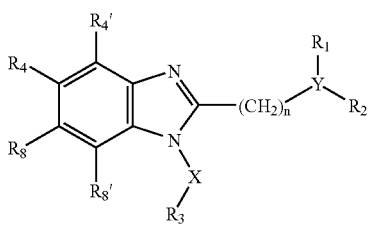

or a pharmaceutically-acceptable salt, solvate, or hydrate, wherein:

$R_1$ and $R_2$ are joined to form a substituted or unsubstituted ring, said substituted ring is a substituted heterocycloalkyl or a substituted 5, 6, 7 or 8 membered-heteroaryl, wherein, when $R_1$ and $R_2$ form said substituted ring, the substituent is at least one unsubstituted lower alkyl, substituted or unsubstituted lower alkoxy, amide, amine, sulfonamide, ester, hydroxy, halide, substituted or unsubstituted aryl, substituted or unsubstituted cycloalkyl, substituted or unsubstituted heterocycloalkyl, or substituted or unsubstituted heteroaryl;

$R_3$ is substituted or unsubstituted 2-benzimidazolyl;

$R_4$, $R_{4'}$, $R_8$, and $R_{8'}$ are each independently hydrogen, halide, saturated or unsaturated straight or branched substituted or unsubstituted alkyl, hydroxy, substituted or unsubstituted alkoxy, substituted or unsubstituted aryl, substituted or unsubstituted arylalkyl, substituted or unsubstituted heterocycloalkyl, substituted or unsubstituted heteroaryl, methyl ester, ethyl ester, $C_1$–$C_2$ amide, carboxylic acid, or sulfonamide;

X is a bond, straight chain or branched substituted or unsubstituted alkyl, -(alkyl)N—, -(alkyl)O—, —C=N—, carbonyl, phosphorus, or sulfur;

Y is nitrogen; and n is an integer from 0 to 4;

wherein said compound is an enantiomer or diastereomer.

5. The compound according to claim 1, wherein $R_{4'}$ and $R_{8'}$ are hydrogen, methyl, methyl ester, ethyl ester, $C_1$–$C_2$ amide, carboxylic acid, methoxy, or sulfonamide.

6. The compound according to claim 1, wherein $R_{4'}$ and $R_{8'}$ are both hydrogen.

7. The compound according to claim 1, wherein $R_4$, $R_{4'}$, $R_8$, and $R_{8'}$ are all hydrogen.

8. A compound of the Formula I:

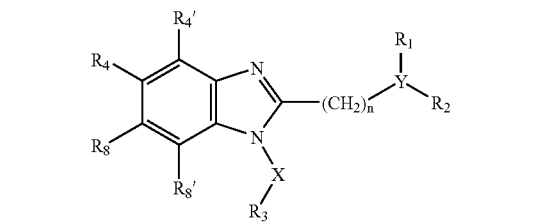

or a pharmaceutically-acceptable prodrug, salt, solvate, hydrate, enantiomer, diastereomer, racemate or mixture of stereoisomer thereof, wherein:

$R_1$ and $R_2$ are joined to form a substituted or unsubstituted ring wherein, when $R_1$ and $R_2$ form a substituted ring, the substituent is at least one unsubstituted lower alkyl, substituted or unsubstituted lower alkoxy, amide, amine, sulfonamide, ester, hydroxy, halide, substituted or unsubstituted aryl, substituted or unsubstituted cycloalkyl, substituted or unsubstituted heterocycloalkyl, or substituted or unsubstituted heteroaryl;

$R_3$ is substituted or unsubstituted 2-benzimidazolyl;

$R_4$, $R_{4'}$, $R_8$, and $R_{8'}$ are each independently hydrogen, halide, saturated or unsaturated straight or branched substituted or unsubstituted alkyl, hydroxy, substituted or unsubstituted alkoxy, substituted or unsubstituted aryl, substituted or unsubstituted arylalkyl, substituted or unsubstituted heterocycloalkyl, substituted or unsubstituted heteroaryl, methyl ester, ethyl ester, $C_1$–$C_2$ amide, carboxylic acid, or sulfonamide;

wherein at least one of $R_4$, $R_{4'}$, $R_8$, and $R_{8'}$ is not hydrogen;

X is a bond, straight chain or branched substituted or unsubstituted alkyl, -(alkyl)N—, -(alkyl)O—, —C=N—, carbonyl, phosphorus, or sulfur;

Y is nitrogen; and n is an integer from 0 to 4.

9. The compound according to claim 8, wherein at least two of $R_4$, $R_{4'}$, $R_8$, and $R_{8'}$ are not hydrogen.

10. The compound according to claim 9, wherein at least three of $R_4$, $R_{4'}$, $R_8$, and $R_{8'}$ are not hydrogen.

11. A compound having the formula:

1-(1H-Benzimidazol-2-ylmethyl)-2-morpholin-4-ylm-ethyl-1H-benzimidazole-5-carboxylic acid methyl ester;

1-(1H-Benzimidazol-2-ylmethyl)-2-morpholin-4-ylm-ethyl-1H-benzimidazole-6-carboxylic acid methyl ester;

{1-[1-(1H-Benzoimidazol-2-ylmethyl)-1H-benzoimidazol-2-ylmethyl]-piperidin-3-yl}-methanol;

{1-[1-(1H-Benzoimidazol-2-ylmethyl)-1H-benzoimidazol-2-ylmethyl]-pyrrolidin-2-yl}-methanol;

2-{1-[1-(1H-benzoimidazol-2-ylmethyl)-1H-benzoimidazol-2-ylmethyl]-piperidin-2-yl}-ethanol;

[1,2,4]Oxadiazol-3-ylmethyl-2-[4-(3-trifluoromethyl-phenyl)-piperazin-1-ylmethyl]-1H-benzoimidazole;

1-[1-(1H-Benzoimidazol-2-ylmethyl)-1H-benzoimidazol-2-ylmethyl]-4-(3-trifluoromethyl-phenyl)piperazine;

1-[1-(1H-Benzoimidazol-2-ylmethyl)-1H-benzoimidazol-2-ylmethyl]-4-(4-trifluoromethyl-phenyl)piperazine;

1-[1-(1H-Benzoimidazol-2-ylmethyl)-1H-benzoimidazol-2-ylmethyl]-4-pyridin-2-ylpiperazine;

(R)-{1-[1-(1H-Benzoimidazol-2-ylmethyl)-1H-benzoimidazol-2-ylmethyl]-pyrrolidin-2-yl}-methanol;

(S)-1-[1-(1H-Benzoimidazol-2-ylmethyl)-1H-benzoimidazol-2-ylmethyl]-pyrrolidine-2-carboxylic acid methyl ester;

(S)-1-[1-(1H-Benzoimidazol-2-ylmethyl)-1H-benzoimidazol-2-ylmethyl]-pyrrolidine-2-carboxylic acid amide;

2-{4-[1-(1H-Benzoimidazol-2-ylmethyl)-1H-benzoimidazol-2-ylmethyl]-piperazin-1-yl}-acetamide;

1-[1-(1H-Benzoimidazol-2-ylmethyl)-1H-benzoimidazol-2-ylmethyl]-piperidine-3-carboxylic acid 1-(1H-benzoimidazol-2-ylmethyl)-1H-benzoimidazol-2-ylmethyl ester; or 1-[1-(1H-Benzoimidazol-2-ylmethyl)-1H-benzoimidazol-2-ylmethyl]-pyrrolidine-2-carboxylic acid 1-(1H-benzoimidazol-2-ylmethyl)-1H-benzoimidazol-2-ylmethyl ester.

12. A compound having the Formula II:

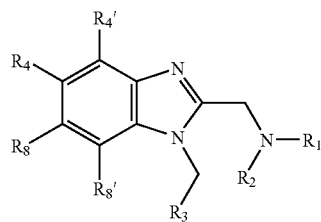

or a pharmaceutically-acceptable prodrug, salt, solvate, hydrate, enantiomer, diastereomer, racemate or mixture of stereoisomer thereof, wherein:

$R_1$ and $R_2$ are joined to form a substituted or unsubstituted ring wherein, when $R_1$ and $R_2$ form a substituted ring, the substituent is at least one unsubstituted lower alkyl, substituted or unsubstituted lower alkoxy, amide, amine, sulfonamide, ester, hydroxy, halide, substituted or unsubstituted aryl, substituted or unsubstituted cycloalkyl, substituted or unsubstituted heterocycloalkyl, or substituted or unsubstituted heteroaryl;

$R_3$ is substituted or unsubstituted 2-benzimidazolyl;

$R_4$, $R_{4'}$, $R_8$, and $R_{8'}$ are each independently hydrogen, halide, saturated or unsaturated straight or branched substituted or unsubstituted alkyl, hydroxy, substituted or unsubstituted alkoxy, substituted or unsubstituted aryl, substituted or unsubstituted arylalkyl, substituted or unsubstituted heterocycloalkyl, substituted or unsubstituted heteroaryl, amine, $C_1$–$C_4$ alkylamine, $C_1$–$C_4$ amide, carboxylic acid, ester, nitro, $C_1$–$C_4$ sulfide, $C_1$–$C_4$ sulfonyl, or sulfonamide.

13. The compound according to claim 12, wherein the substituent of $R_3$, if present, is at least one hydroxy, halide, $C_1$–$C_4$ alkyl, $C_1$–$C_4$ alkoxy, $C_1$–$C_4$ sulfide, $C_1$–$C_4$ sulfonyl, nitro, carboxylic acid, ester, amine, or $C_1$–$C_4$ alkylamine.

14. The compound according to claim 12, wherein $R_4$, $R_{4'}$, $R_8$, and $R_{8'}$ are each independently hydrogen, $C_1$–$C_4$ alkyl, $C_1$–$C_4$ alkoxy, amine, $C_1$–$C_4$ alkylamine, $C_1$–$C_4$ amide, carboxylic acid, ester, halide, hydroxy, nitro, $C_1$–$C_4$ sulfide, $C_1$–$C_4$ sulfonyl, or sulfonamide.

15. The compound according to claim 12, wherein the compound of Formula II is an enantiomer or diastereomer.

16. The compound according to claim 12, wherein $R_4$, $R_{4'}$, $R_8$, and $R_{8'}$ are hydrogen.

17. The compound according to claim 12, wherein at least one of $R_4$, $R_{4'}$, $R_8$, or $R_{8'}$ is not hydrogen.

18. The compound according to claim 12 having formula:

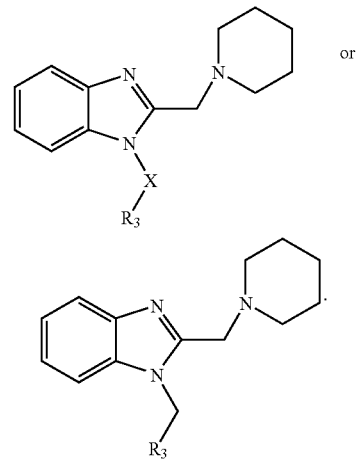

19. A compound of the Formula IV:

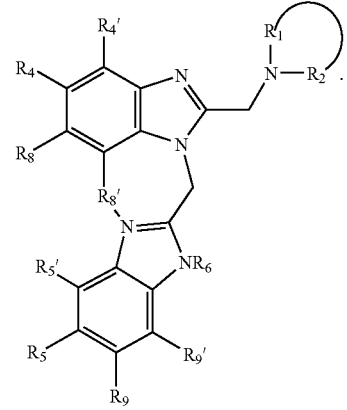

or a pharmaceutically-acceptable prodrug, salt, solvate, hydrate, enantiomer, diastereomer, racemate or mixture of stereoisomer thereof, wherein:
—$R_1$—N—$R_2$— form a saturated or unsaturated substituted or unsubstituted heterocycloalkyl ring, substituted or unsubstituted heteroaryl ring, wherein, if present, the substituent is at least one unsubstituted lower alkyl, substituted or unsubstituted lower alkoxy, amide, amine, sulfonamide, ester, hydroxy, halide, substituted or unsubstituted aryl, substituted or unsubstituted cycloalkyl, substituted or unsubstituted heterocycloalkyl, substituted or unsubstituted heterocycloaryl or substituted or unsubstituted heteroaryl;
$R_4$, $R_{4'}$, $R_5$, $R_{5'}$, $R_8$, $R_{8'}$, $R_9$, and $R_{9'}$ are each independently hydrogen, halide, saturated or unsaturated straight or branched substituted or unsubstituted alkyl, hydroxy, substituted or unsubstituted alkoxy, substituted or unsubstituted cycloalkyl, substituted or unsubstituted aryl, substituted or unsubstituted arylalkyl, substituted or unsubstituted heterocycloalkyl, substituted or unsubstituted heterocycloaryl or substituted or unsubstituted heteroaryl; and
$R_6$ is hydrogen, saturated or unsaturated straight or branched substituted or unsubstituted alkyl, substituted or unsubstituted alkoxy, substituted or unsubstituted alkylamino, substituted or unsubstituted cycloalkyl, substituted or unsubstituted heterocycloalkyl, substituted or unsubstituted aryl, substituted or unsubstituted arylalkyl, substituted or unsubstituted heterocycloaryl or substituted or unsubstituted heteroaryl.

20. The compound according to claim 19, wherein:
—$R_1$—N—$R_2$— form a saturated or unsaturated, substituted or unsubstituted 3 to 7 membered heterocycloalkyl, substituted or unsubstituted 3 to 7 membered heteroaryl, wherein, if present, the substituent is at least one substituted or unsubstituted $C_1$–$C_4$ alkyl, substituted or unsubstituted $C_1$–$C_4$ alkoxy, $C_1$–$C_4$ esters, hydroxy, fluoride, chloride, bromide, substituted or unsubstituted 3 to 8 membered aryl, substituted or unsubstituted 4 to 6 membered cycloalkyl, substituted or unsubstituted 3 to 8 membered heterocycloalkyl, carbonyl, or nitro.

21. The compound according to claim 19, wherein:
$R_4$, $R_{4'}$, $R_5$, $R_{5'}$, $R_6$, $R_8$, $R_{8'}$, $R_9$, and $R_{9'}$ are each independently hydrogen, $C_1$–$C_4$ alkyl, $C_1$–$C_4$ alkoxy, amine, $C_1$–$C_4$ alkylamine, $C_1$–$C_4$ amide, carboxylic acid, ester, halide, hydroxy, nitro, $C_1$–$C_4$ sulfide, $C_1$–$C_4$ sulfonyl, or sulfonamide.

22. The compound according to claim 19, wherein $R_{4'}$, $R_{5'}$, $R_{8'}$, and $R_{9'}$ are hydrogen.

23. The compound according to claim 19, wherein at least one of $R_4$, $R_{4'}$, $R_8$, and $R_{8'}$ is not hydrogen.

24. The compound according to claim 19, wherein $R_5$, $R_{5'}$, $R_9$, and $R_{9'}$ are hydrogen.

25. The compound according to claim 19, wherein at least one of $R_5$, $R_{5'}$, $R_9$, and $R_{9'}$ is not hydrogen.

26. The compound according to claim 19, wherein $R_6$ is hydrogen.

27. The compound according to claim 19, wherein:
—$R_1$—N—$R_2$— form a 5, 6, or 8 membered ring; and
$R_4$, $R_{4'}$, $R_5$, $R_{5'}$, $R_6$, $R_8$, $R_{8'}$, $R_9$, and $R_{9'}$ are each independently are hydrogen $C_1$–$C_2$ alkyl, $C_1$–$C_2$ alkoxy, amine, $C_1$–$C_2$ alkylamine, fluoride, chloride, bromide, hydroxy, nitro, $C_1$–$C_2$ sulfide, or $C_1$–$C_2$ sulfonyl.

28. The compound according to claim 19, wherein the 5, 6, or 8 membered ring formed by —$R_1$—N—$R_2$— is a unsubstituted or substituted pyrrolidinyl, unsubstituted or substituted piperidinyl, unsubstituted or substituted pyrrolyl, unsubstituted or substituted imidazolyl, unsubstituted or substituted unsubstituted or substituted pyridinyl, unsubstituted or substituted pyrimidinyl, unsubstituted or substituted piperazinyl, unsubstituted or substituted quinolinyl, unsubstituted or substituted acridinyl, unsubstituted or substituted thiazole, or unsubstituted or substituted morpholinyl, wherein, if present, the substituent, is at least one methyl, ethyl, ester, methanol, 2-ethanol, or aldehyde.

29. The compound according to claim 19, wherein:
—$R_1$—N—$R_2$— form a cyclic structure: 2,5-dihydropyrrolyl, 3,5-dimethylpyrrolidinyl, 2-hydroxymethylpyrrolidinyl, 2-(2-hydroxyethyl)piperidinyl, N-carbaldehydepiperazinyl, N-(3-trifluoromethylphenyl)piperazinyl, N-(4-hydroxyphenyl)piperazinyl, N-(benzylcarbate)piperazinyl, tetrahydrothiazolyl, N-(4-acetylphenyl)piperazinyl, or cyclooctazanyl.

30. The compound according to claim 19, wherein the compound of Formula IV is an enantiomer or diastereomer.

31. The compound according to claim 19 having Formula XIII:

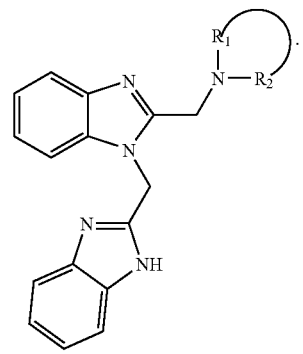

32. The compound according to claim 19 having Formula XIV:

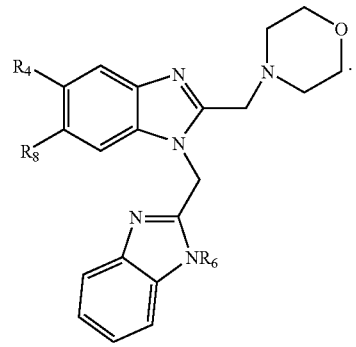

33. A compound of the formula:
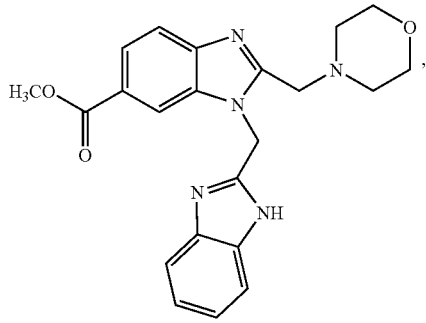
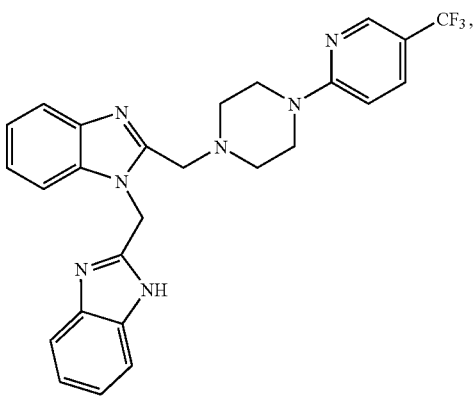
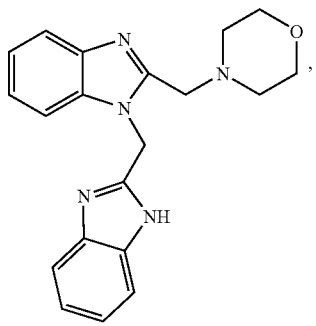
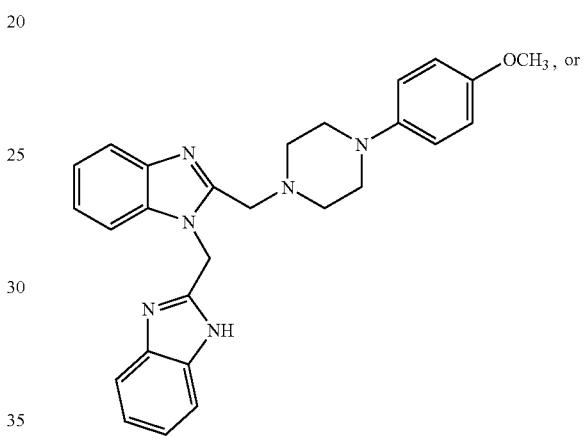
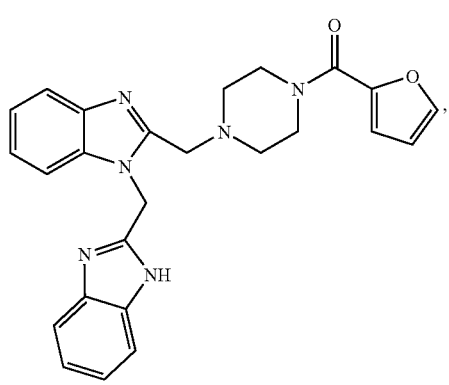
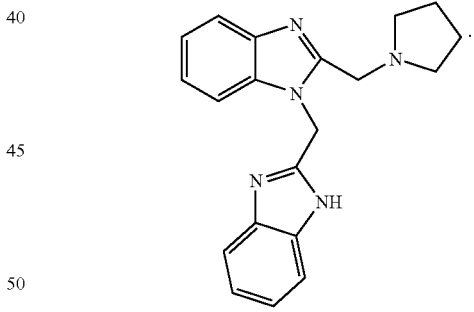
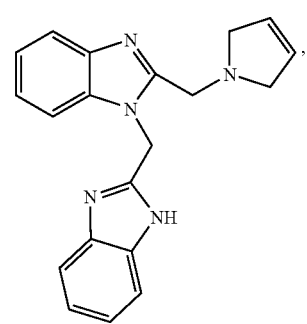
34. A pharmaceutical composition in solid form comprising a compound of the Formula I:
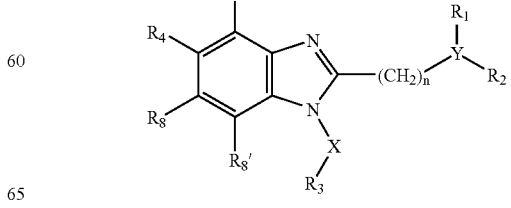

or a pharmaceutically-acceptable prodrug, salt, solvate, hydrate, enantiomer, diastereomer, racemate or mixture of stereoisomer thereof, wherein:

$R_1$ and $R_2$ are joined to form a substituted or unsubstituted ring wherein, when $R_1$ and $R_2$ form a substituted ring, the substituent is at least one unsubstituted lower alkyl, substituted or unsubstituted lower alkoxy, amide, amine, sulfonamide, ester, hydroxy, halide, substituted or unsubstituted aryl, substituted or unsubstituted cycloalkyl, substituted or unsubstituted heterocycloalkyl, or substituted or unsubstituted heteroaryl;

$R_3$ is substituted or unsubstituted 2-benzimidazolyl;

$R_4$, $R_{4'}$, $R_8$, and $R_{8'}$ are each independently hydrogen, halide, saturated or unsaturated straight or branched substituted or unsubstituted alkyl, hydroxy, substituted or unsubstituted alkoxy, substituted or unsubstituted aryl, substituted or unsubstituted arylalkyl, substituted or unsubstituted heterocycloalkyl, substituted or unsubstituted heteroaryl, methyl ester, ethyl ester, $C_1$–$C_2$ amide, carboxylic acid, or sulfonamide;

X is a bond, straight chain or branched substituted or unsubstituted alkyl, -(alkyl)N—, -(alkyl)O—, —C=N—, carbonyl, phosphorus, or sulfur;

Y is nitrogen; and n is an integer from 0 to 4;

a pharmaceutically acceptable carrier.

35. A pharmaceutical composition comprising the compound according to claim 12 and a pharmaceutically acceptable carrier.

36. A pharmaceutical composition comprising the compound according to claim 19 and a pharmaceutically acceptable carrier.

37. The compound of claim 1 which is a pharmaceutically-acceptable salt, solvate, hydrate, enantiomer, diastereomer, racemate or mixture of stereoisomer.

38. The compound of claim 12 which is a pharmaceutically-acceptable salt, solvate, hydrate, enantiomer, diastereomer, racemate or mixture of stereoisomer.

39. The compound of claim 19 which is a pharmaceutically-acceptable salt, solvate, hydrate, enantiomer, diastereomer, racemate or mixture of stereoisomer.

* * * * *